US010667904B2

(12) United States Patent
Marquez et al.

(10) Patent No.: US 10,667,904 B2
(45) Date of Patent: Jun. 2, 2020

(54) VALVE IMPLANT WITH INTEGRATED SENSOR AND TRANSMITTER

(71) Applicant: Edwards Lifesciences Corporation, Irvine, CA (US)

(72) Inventors: Salvador Marquez, Foothill Ranch, CA (US); Da-Yu Chang, Irvine, CA (US); Cindy Woo, Costa Mesa, CA (US); Hao-Chung Yang, Tustin, CA (US); Lynn T. Dang, Huntingdon Beach, CA (US); Javier A. Sanguinetti, Irvine, CA (US); Alexander H. Siemons, Yorba Linda, CA (US); Yaron Keidar, Irvine, CA (US); Virginia Qi Lin, Santa Ana, CA (US); Brian S. Conklin, Orange, CA (US); Donald E. Bobo, Jr., Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 15/452,617

(22) Filed: Mar. 7, 2017

(65) Prior Publication Data
US 2017/0258585 A1 Sep. 14, 2017

Related U.S. Application Data

(60) Provisional application No. 62/417,206, filed on Nov. 3, 2016, provisional application No. 62/305,347, filed on Mar. 8, 2016.

(51) Int. Cl.
*A61F 2/24* (2006.01)
*A61B 5/026* (2006.01)
*A61B 5/00* (2006.01)

(52) U.S. Cl.
CPC .......... *A61F 2/2409* (2013.01); *A61B 5/0031* (2013.01); *A61B 5/026* (2013.01);
(Continued)

(58) Field of Classification Search
CPC ........ A61F 2/24; A61F 2/2412; A61F 2/2418; A61B 5/0031; A61B 5/4851; A61B 2017/0011; A61B 2562/0261
See application file for complete search history.

(56) References Cited

U.S. PATENT DOCUMENTS 3,143,742 A 8/1964 Cromie
3,320,972 A 5/1967 High et al.
(Continued)

FOREIGN PATENT DOCUMENTS

EP 0125393 A1 11/1984
EP 0143246 A2 6/1985
(Continued)

*Primary Examiner* — Christopher D. Prone
(74) *Attorney, Agent, or Firm* — Chang & Hale

(57) ABSTRACT

Sensor-integrated prosthetic valves that can comprise a variety of features, including a plurality of valve leaflets, a frame assembly configured to support the plurality of valve leaflets and define a plurality of commissure supports terminating at an outflow end of the prosthetic valve, a sensor device associated with the frame assembly and configured to generate a sensor signal, for example, a sensor signal indicating deflection of one or more of the plurality of commissure supports, and a transmitter assembly configured to receive the sensor signal from the sensor device and wirelessly transmit a transmission signal that is based at least in part on the sensor signal.

11 Claims, 35 Drawing Sheets

(52) U.S. Cl.
CPC ............ *A61B 5/4851* (2013.01); *A61B 5/686* (2013.01); *A61F 2/2412* (2013.01); *A61F 2/2418* (2013.01); *A61F 2/2445* (2013.01); *A61B 2562/0261* (2013.01); *A61F 2210/0076* (2013.01); *A61F 2230/0069* (2013.01); *A61F 2240/00* (2013.01)

(56) References Cited

U.S. PATENT DOCUMENTS

| | | |
|---|---|---|
| 3,371,352 A | 3/1968 | Siposs et al. |
| 3,546,710 A | 12/1970 | Shumakov et al. |
| 3,574,865 A | 4/1971 | Hamaker |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,566,465 A | 1/1986 | Arhan et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,014 A | 11/1994 | Sauter et al. |
| 5,360,444 A | 11/1994 | Kusuhara |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,487,760 A | 1/1996 | Villafana |
| 5,488,789 A | 2/1996 | Religa et al. |
| 5,489,296 A | 2/1996 | Love et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,801 A | 1/1999 | Lin et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,554 A | 3/2000 | Rosenman et al. |
| 6,042,607 A | 3/2000 | Williamson, IV et al. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,264,611 B1 | 7/2001 | Ishikawa et al. |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,350,282 B1 | 2/2002 | Eberhardt |
| 6,371,983 B1 | 4/2002 | Lane |
| 6,375,620 B1 | 4/2002 | Oser |
| 6,402,780 B2 | 6/2002 | Williamson, IV et al. |
| 6,409,674 B1 | 6/2002 | Brockway et al. |
| 6,425,916 B1 | 7/2002 | Garrison et al. |

(56) References Cited

U.S. PATENT DOCUMENTS

| | | |
|---|---|---|
| 6,440,164 B1 | 8/2002 | DiMatteo et al. |
| 6,442,413 B1 | 8/2002 | Silver |
| 6,454,799 B1 | 9/2002 | Schreck |
| 6,458,153 B1 | 10/2002 | Bailey et al. |
| 6,468,305 B1 | 10/2002 | Otte |
| 6,491,624 B1 | 12/2002 | Lotfi |
| 6,582,462 B1 | 6/2003 | Andersen et al. |
| 6,585,766 B1 | 7/2003 | Kluynh et al. |
| 6,645,143 B2 | 11/2003 | VanTassel et al. |
| 6,652,464 B2 | 11/2003 | Schwartz et al. |
| 6,652,578 B2 | 11/2003 | Bailey et al. |
| 6,675,049 B2 | 1/2004 | Thompson et al. |
| 6,682,559 B2 | 1/2004 | Myers et al. |
| 6,685,739 B2 | 2/2004 | DiMatteo et al. |
| 6,730,118 B2 | 5/2004 | Spenser et al. |
| 6,733,525 B2 | 5/2004 | Yang et al. |
| 6,741,885 B1 | 5/2004 | Park et al. |
| 6,764,508 B1 | 7/2004 | Roehe et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,795,732 B2 | 9/2004 | Stadler et al. |
| 6,805,711 B2 | 10/2004 | Quijano et al. |
| 6,893,459 B1 | 5/2005 | Macoviak |
| 6,893,460 B2 | 5/2005 | Spenser et al. |
| 6,895,265 B2 | 5/2005 | Silver |
| 6,908,481 B2 | 6/2005 | Cribier |
| 6,939,365 B1 | 9/2005 | Fogarty et al. |
| 7,011,681 B2 | 3/2006 | Vesely |
| 7,025,780 B2 | 4/2006 | Gabbay |
| 7,033,322 B2 | 4/2006 | Silver |
| 7,052,466 B2 | 5/2006 | Scheiner et al. |
| 7,070,616 B2 | 7/2006 | Majercak et al. |
| 7,082,330 B2 | 7/2006 | Stadler et al. |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,416,530 B2 | 8/2008 | Turner |
| 7,422,603 B2 | 9/2008 | Lane |
| 7,513,909 B2 | 4/2009 | Lane et al. |
| 7,556,647 B2 | 7/2009 | Drews et al. |
| 7,569,072 B2 | 8/2009 | Berg et al. |
| 7,621,878 B2 | 11/2009 | Ericson et al. |
| 7,916,013 B2 | 3/2011 | Stevenson |
| 7,998,151 B2 | 8/2011 | St. Goar et al. |
| 8,066,650 B2 | 11/2011 | Lee et al. |
| 8,248,232 B2 | 8/2012 | Stevenson et al. |
| 8,253,555 B2 | 8/2012 | Stevenson et al. |
| 8,340,750 B2 | 12/2012 | Prakash et al. |
| 8,401,659 B2 | 3/2013 | Von Arx et al. |
| 8,529,474 B2 | 9/2013 | Gupta et al. |
| 8,622,936 B2 | 1/2014 | Schenberger et al. |
| 9,101,264 B2 | 8/2015 | Acquista |
| 9,101,281 B2 | 8/2015 | Reinert et al. |
| 9,808,201 B2 * | 11/2017 | Braido .................. A61B 5/02 |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0010296 A1 | 1/2004 | Swanson et al. |
| 2004/0019374 A1 | 1/2004 | Hojeibane et al. |
| 2004/0027306 A1 | 2/2004 | Amundson et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |

(56) References Cited

U.S. PATENT DOCUMENTS

| | | |
|---|---|---|
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0241745 A1 | 10/2006 | Solem |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0033543 A1 | 2/2008 | Gurskis et al. |
| 2008/0046040 A1 | 2/2008 | Denker et al. |
| 2008/0119875 A1 | 5/2008 | Ino et al. |
| 2008/0154356 A1 | 6/2008 | Obermiller et al. |
| 2008/0319543 A1 | 12/2008 | Lane |
| 2009/0036903 A1 | 2/2009 | Ino et al. |
| 2009/0192599 A1 | 7/2009 | Lane et al. |
| 2010/0049313 A1 | 2/2010 | Alon et al. |
| 2010/0145438 A1 | 6/2010 | Barone |
| 2010/0256723 A1 | 10/2010 | Murray |
| 2011/0218622 A1* | 9/2011 | Shaolian ............... A61B 17/00 623/2.37 |
| 2012/0123284 A1 | 5/2012 | Kheradvar |
| 2012/0296382 A1 | 11/2012 | Shuros et al. |
| 2013/0144379 A1 | 6/2013 | Najafi et al. |
| 2014/0081154 A1 | 3/2014 | Toth |
| 2014/0107768 A1 | 4/2014 | Venkatasubramanian |
| 2014/0128964 A1 | 5/2014 | Delaloye |
| 2014/0188221 A1 | 7/2014 | Chung et al. |
| 2014/0364707 A1 | 12/2014 | Kintz et al. |
| 2015/0045635 A1 | 2/2015 | Tankiewicz et al. |
| 2016/0045165 A1 | 2/2016 | Braido et al. |
| 2016/0045316 A1 | 2/2016 | Braido et al. |
| 2017/0196509 A1 | 7/2017 | Hunter |

FOREIGN PATENT DOCUMENTS

| | | |
|---|---|---|
| SU | 1116573 A1 | 7/1985 |
| SU | 1697790 A1 | 12/1991 |
| WO | 9213502 A1 | 8/1992 |
| WO | 9742871 A1 | 11/1997 |

* cited by examiner

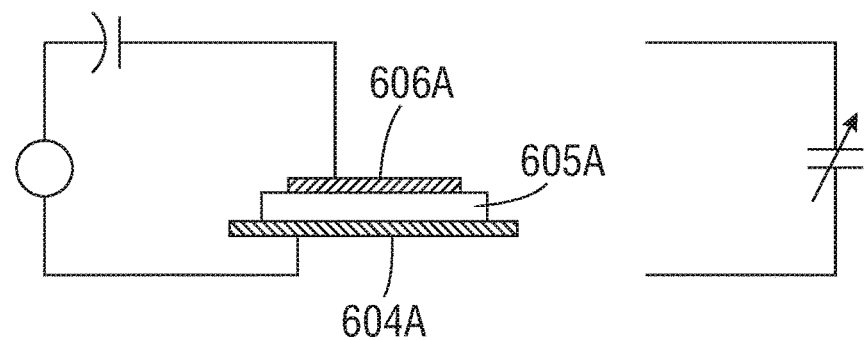
FIG. 6A   FIG. 6B
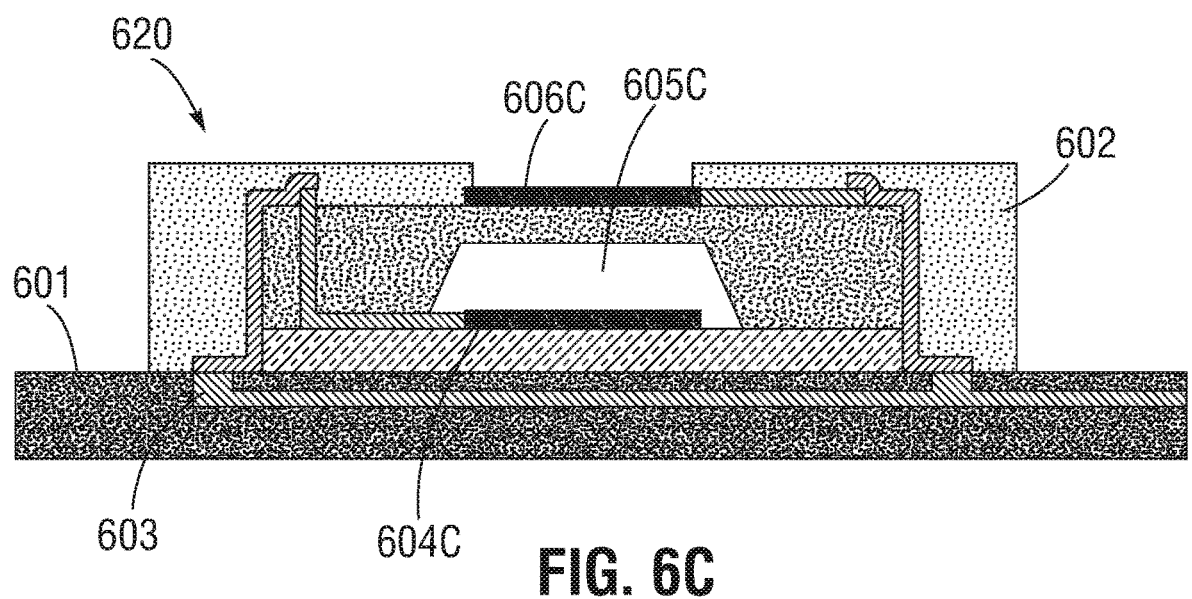
FIG. 6C

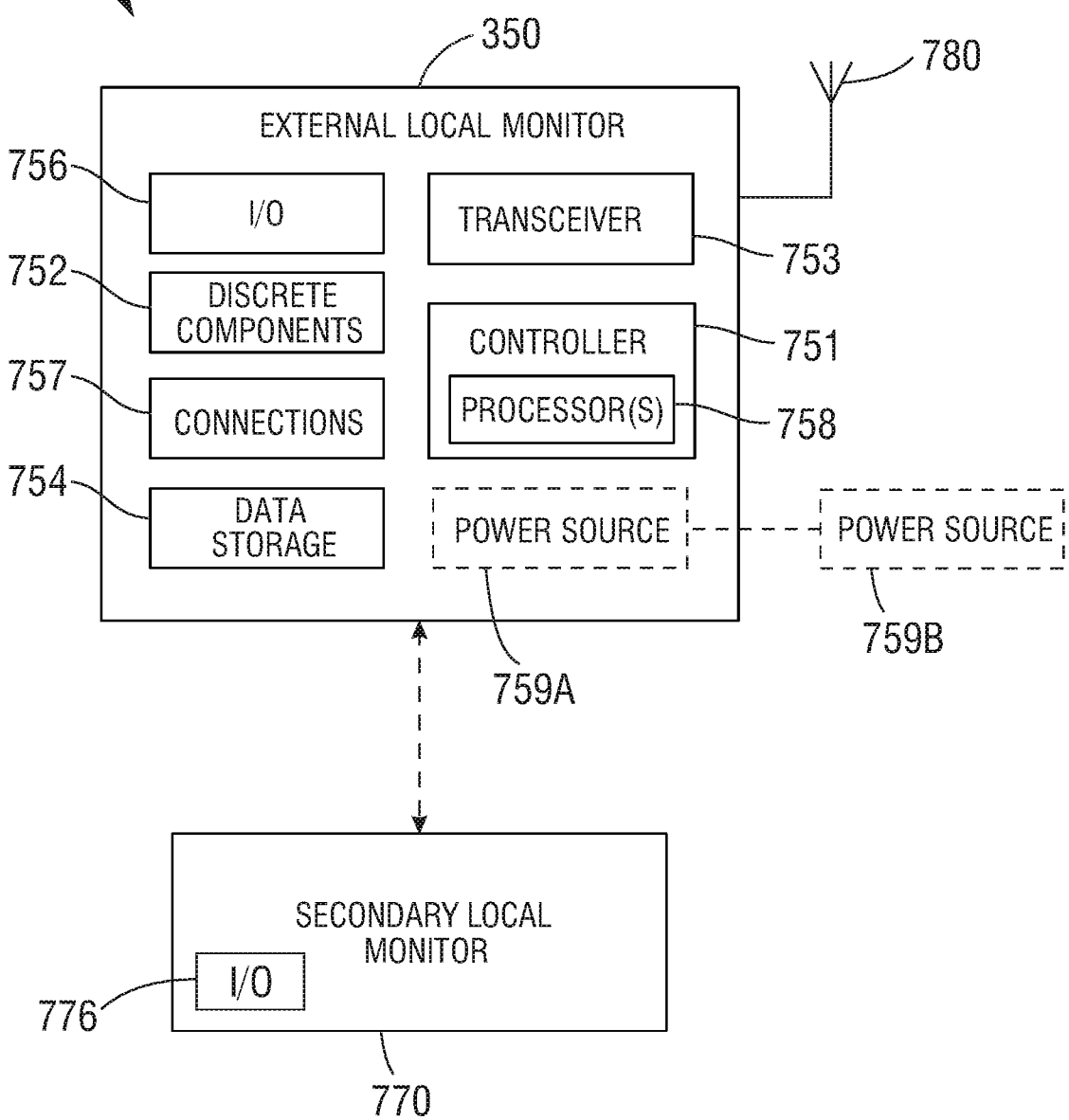

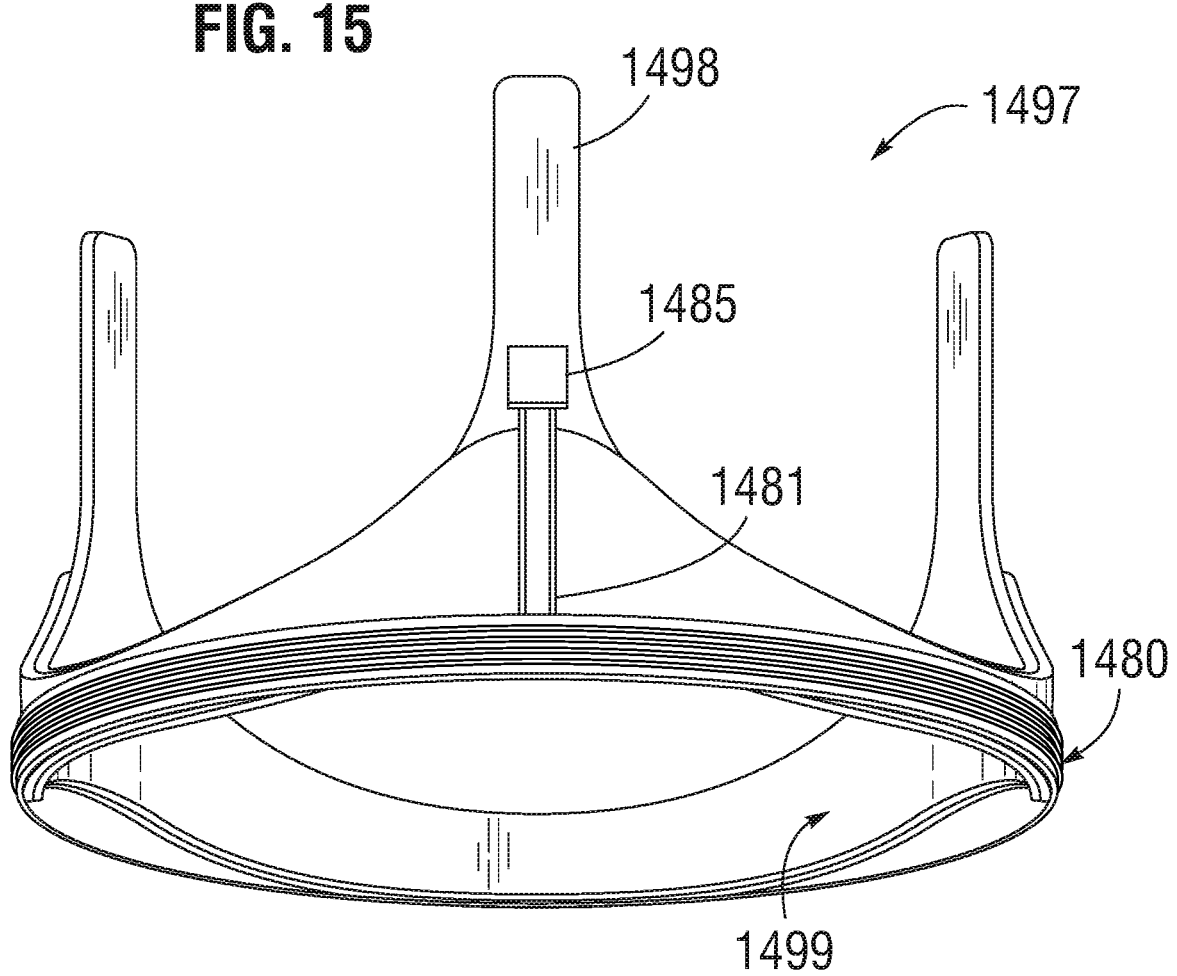

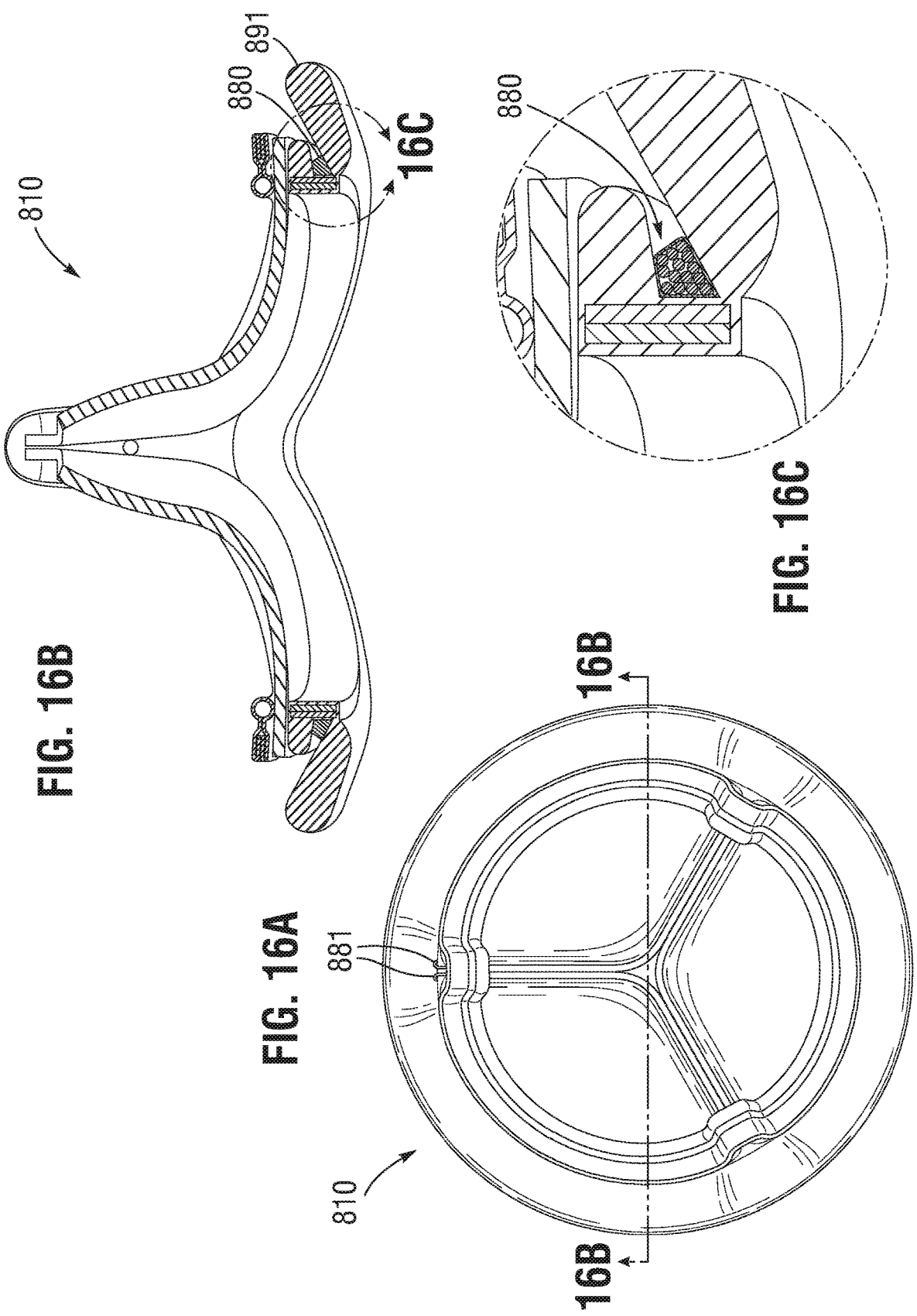

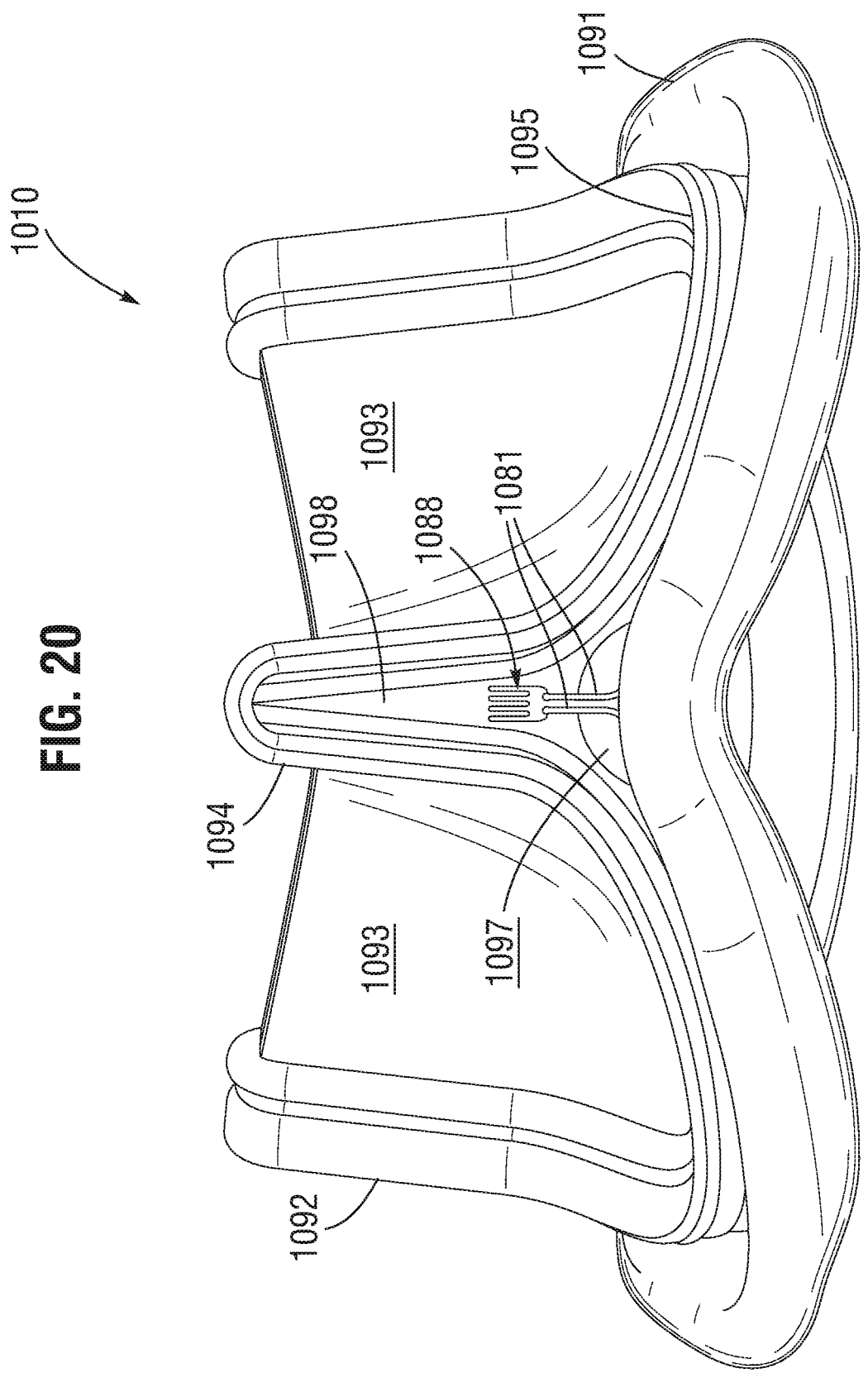

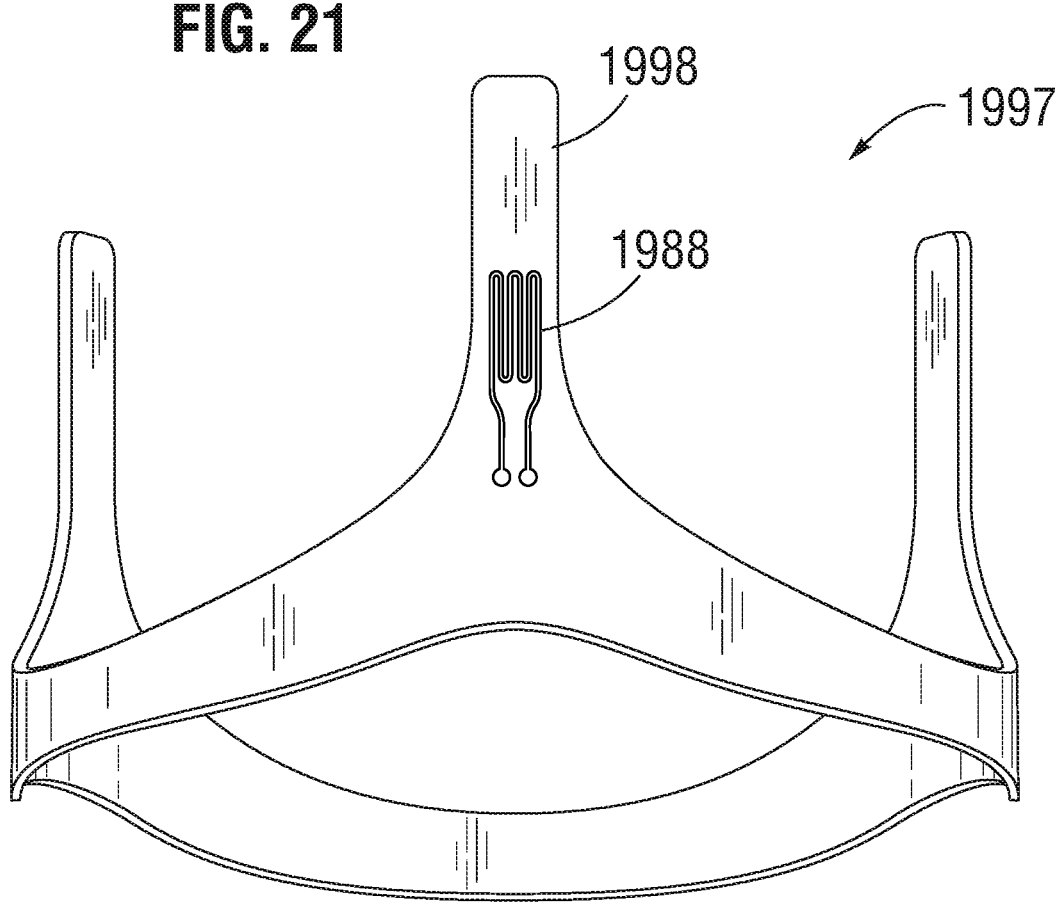

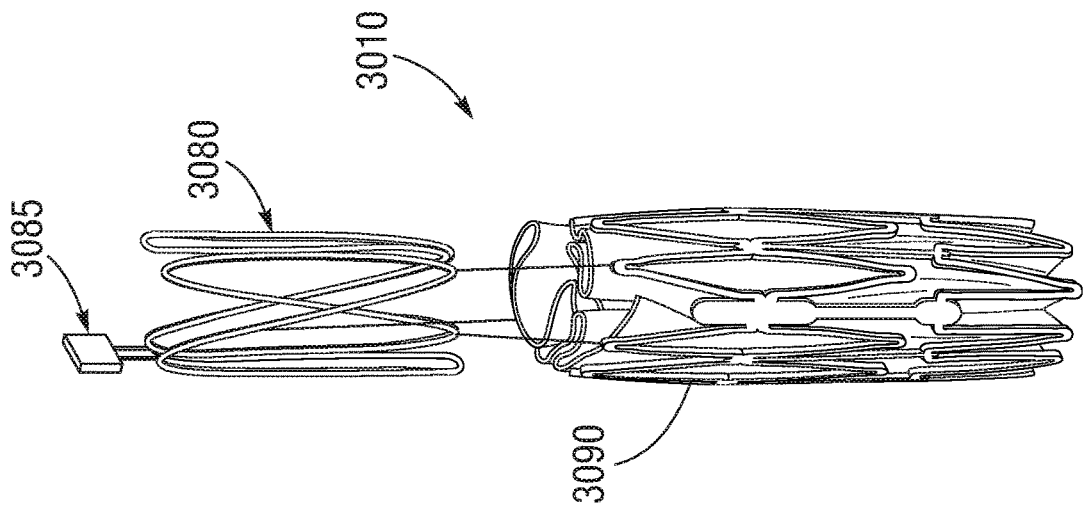
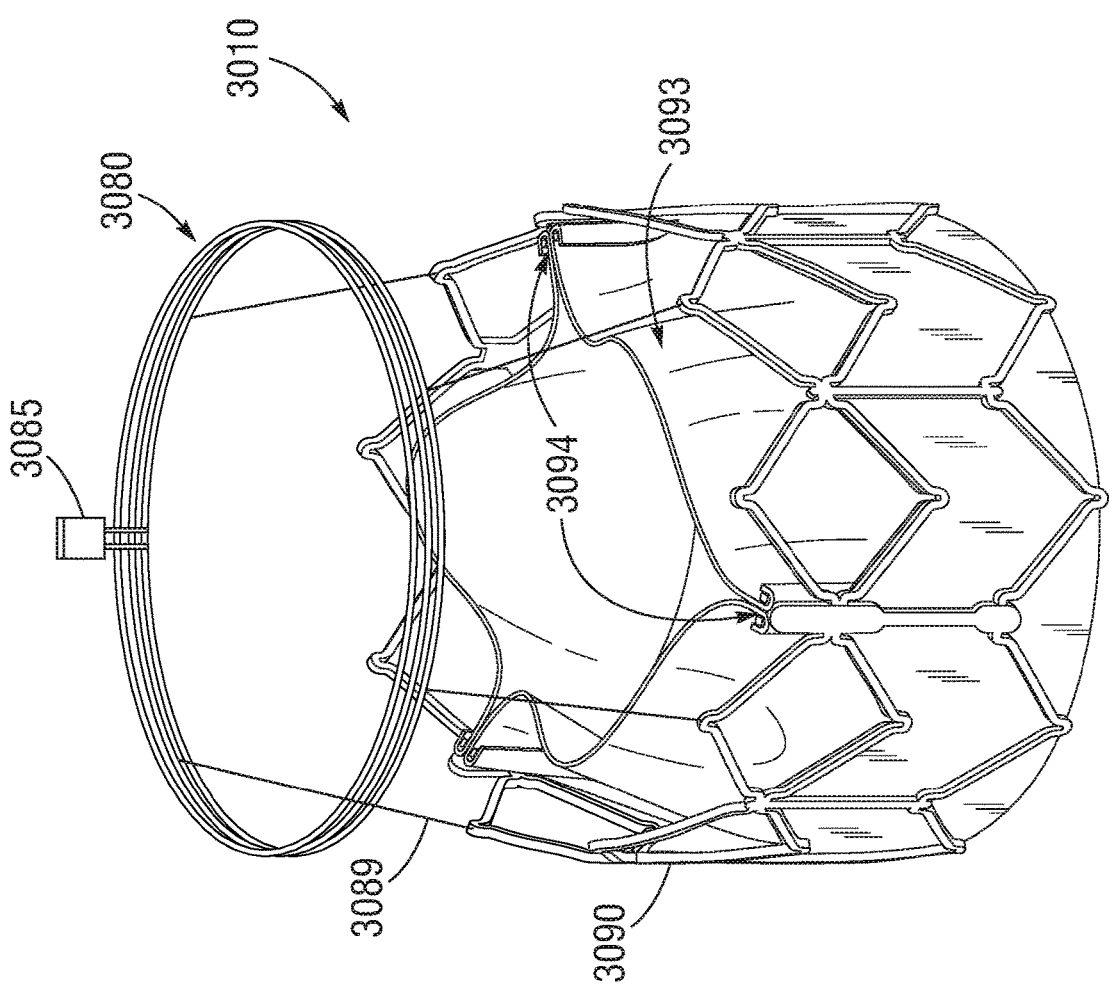

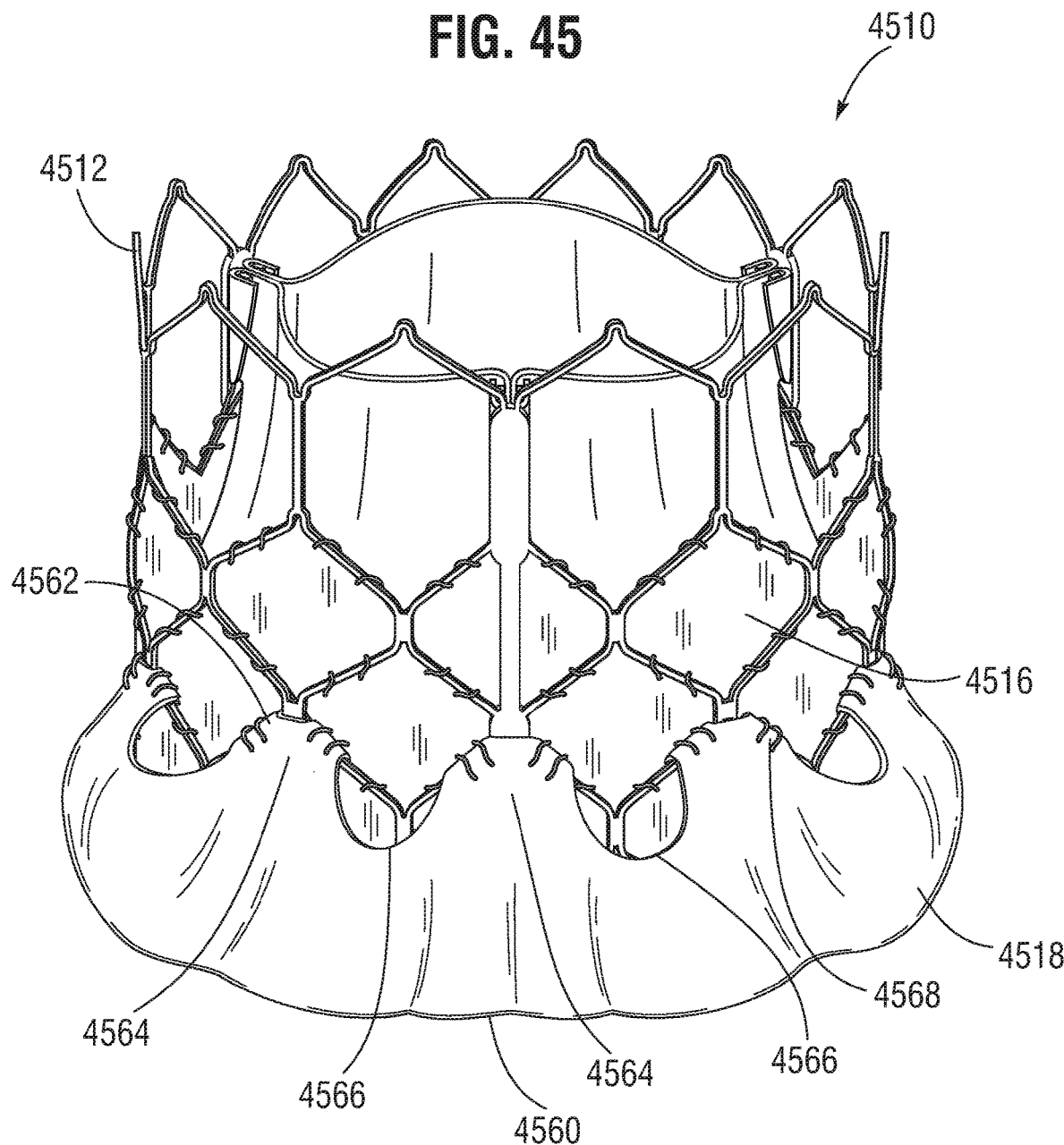

VALVE IMPLANT WITH INTEGRATED SENSOR AND TRANSMITTER

RELATED APPLICATIONS

This application claims priority to U.S. Provisional Application Nos. 62/305,347, filed Mar. 8, 2016 and entitled VALVE IMPLANT WITH INTEGRATED SENSOR AND TRANSMITTER, and 62/417,206, filed Nov. 3, 2016 and entitled VALVE IMPLANT WITH INTEGRATED SENSOR AND TRANSMITTER, the disclosures of which are hereby incorporated by reference in their entirety.

BACKGROUND

Technical Field

The present disclosure generally relates to the field of prosthetic implant devices.

Description of Related Art

Biocompatible implant devices, such as heart valves, may be implanted in patients to treat various conditions. Post-implant malfunction of such implant devices can result in serious health complications.

SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways.

In some implementations, a prosthetic implant (e.g., a prosthetic valve, prosthetic heart valve, annuloplasty ring, stent, graft, etc.) can include one or more sensor devices. For example, a prosthetic valve can comprise a plurality of valve leaflets, a frame assembly configured to support the plurality of valve leaflets and define a plurality of commissure supports (e.g., commissure posts, commissure attachment structures, other support structures, etc.). The commissure supports can terminate at or proximate an outflow end of the prosthetic valve. The prosthetic valve can also comprise a sensor device (e.g., a sensor) or an electrical sensor device (e.g., an electrical sensor) associated with the frame assembly. The sensor device (e.g., electrical sensor device) can be configured to generate a sensor signal indicating deflection of one or more of the plurality of commissure supports (or another portion of the prosthetic valve or frame assembly). The sensor device (e.g., electrical sensor device) can comprise circuitry for converting analog sensor signals to digital sensor signals. The prosthetic valve can also comprise a transmitter assembly configured to receive the sensor signal from the sensor device (e.g., electrical sensor device) and wirelessly transmit a transmission signal, wherein the transmission signal is based at least in part on the sensor signal (e.g., the transmission signal correlates, relates, is proportional, etc. to the sensor signal).

The sensor device (e.g., electrical sensor device) can be a strain gauge. For example, the strain gauge can comprise a conductive material disposed in an etched portion of the frame assembly. The strain gauge can comprise a conductive material printed on the frame assembly.

The sensor device (e.g., electrical sensor device) can comprise a piezoelectric sensor. For example, the piezoelectric sensor can be a component of a sensor microchip including circuitry housed within a protective housing. The piezoelectric sensor can be fixed to base of one of the plurality of commissure supports (e.g., commissure posts, commissure attachment structures, other support structures, etc.). The piezoelectric sensor can be fixed to a distal end portion of one of the plurality of commissure supports. The piezoelectric sensor can comprise a piezoelectric material layer disposed between first and second conductive layers. A biocompatible laminate layer can be configured to at least partially provide a protective barrier for one or more of the piezoelectric material layer, the first conductive layer and the second conductive layer. The piezoelectric sensor can comprise a piezoresistive device. The piezoelectric sensor can be integrated into a stent member of the frame assembly. The stent member can comprise flexible plastic, shape memory material, nitinol, stainless steel, other materials, and/or a combination of one or more of these. The stent member can comprise stacked sheets of piezoelectric material (e.g., 2-15 stacked sheets).

The transmitter assembly can be configured to receive power wirelessly from an external power supply and transmit the transmission signal using the received power. The external power supply can be a variety of power supplies (e.g., any power supply disclosed in this disclosure or otherwise known) and can comprise a wearable strap configured to be worn around an abdomen of a patient in whom the prosthetic valve is implanted. The transmitter assembly can comprise an antenna coil wrapped around a stiffening band of the frame assembly. Optionally, a power generator could also or alternatively be associated with the frame assembly to generate power (e.g., in response to movement, deflection, etc.).

The prosthetic valve can additionally (or as an alternative to one of the electrical sensor device examples above) comprise a flow sensor configured to sense a flow of blood in the blood flow lumen and generate a flow signal based on the flow. The prosthetic valve can further comprise an annular sealing ring, wherein the transmitter assembly comprises a plurality of windings circumferentially wrapped around a core form that runs along a portion of the annular sealing ring. This can be the same as or similar to the core forms and/or plurality of windings described elsewhere herein.

Methods of monitoring a prosthetic implant (e.g., the prosthetic valve described above or any prosthetic implant described elsewhere in this disclosure) that is inside a patient (e.g., implanted in a heart or other location within a patient) and/or methods of monitoring a patient that has the/a prosthetic implant can comprise a variety of steps. For example, the method(s) can comprise measuring a deflection of one or more portions or supports of the prosthetic implant or a frame assembly of the prosthetic implant (e.g., in a prosthetic valve the same as or similar to that above, the method can comprise measuring a deflection of one or more of a plurality of commissure supports of the/a prosthetic valve). This can be done, for example, using a sensor device or an electrical sensor device (e.g., the same as or similar to the sensor device/electrical sensor device described above or sensor devices described elsewhere in this disclosure) associated with a frame assembly of the prosthetic implant, e.g., associated with a plurality of commissure support posts that may be included in or be part of the frame assembly. The method(s) can include wirelessly coupling a transmitter assembly of the prosthetic implant to an external receiver through biological tissue of the patient. The method(s) can also include wirelessly transmitting data indicating the deflection to the external receiver using the transmitter assembly.

Methods involving using the prosthetic implant (e.g., the prosthetic valve described above and/or other prosthetic implants/valves described elsewhere herein) can comprise receiving power at the prosthetic implant wirelessly from an external power supply, wherein wirelessly transmitting the data can be performed at least in part using the received power. The power can be received using a piezoelectric device of the electrical sensor device. Receiving the power can comprise receiving an ultrasound signal using the piezoelectric device. Receiving the power can also comprise receiving a wireless power signal from a wearable strap worn around an abdomen of the patient. The piezoelectric sensor device can comprise a piezoresistive device. The piezoelectric sensor can be integrated into the frame assembly, a support (e.g., one of the commissure supports), or other portion. For example, one of a plurality of commissure supports or other support can comprise stacked sheets of piezoelectric material. The piezoelectric sensor can be the same as or similar to the piezo electric sensor described above or those described elsewhere in this disclosure.

A prosthetic implant (e.g., which may be the same as or similar to the prosthetic valves/implants discussed above or elsewhere in this disclosure) can comprise a power generator. The prosthetic implant can include a frame assembly. If the prosthetic implant is a prosthetic valve (e.g., prosthetic heart valve), the prosthetic valve can comprise a plurality of valve leaflets and a frame assembly configured to support the plurality of valve leaflets and define a plurality of commissure supports (e.g., commissure posts, commissure attachment structures, other support structures, etc.). The commissure supports can terminate at or proximate an outflow end of the prosthetic valve. The power generator can be connected to, integrated with, and/or otherwise associated with the frame assembly of the prosthetic implant. The power generator can be configured to generate electrical power in response to deflection of one or more portion or support of the prosthetic implant (e.g., in response to deflection of one or more of the plurality of commissure supports). The prosthetic implant/valve can also comprise a transmitter assembly configured to wirelessly transmit a transmission signal using the generated power from the power generator.

The transmitter assembly/assemblies described above or elsewhere herein can include an electrically conductive coil. The transmitter assembly/assemblies can be further configured to perform wireless transmission using the coil. One, some, or all of the plurality of commissure supports (e.g., commissure posts, commissure attachment structures, other support structures, etc.) of a prosthetic valve or other support/portions of a prosthetic implant can be configured to deflect in response to the formation of fluid vortices in a fluid channel in which the prosthetic implant/valve is disposed. Optionally, the power generator can be disposed on, disposed in, connected/attached to, or otherwise associated with one or more of the commissure supports or other supports/portions. The power generator can comprise a piezoelectric capacitive device. The power generator can comprise a piezoelectric material layer disposed between first and second conductive plates, and a biocompatible laminate layer at least partially providing a protective barrier for one or more of the piezoelectric material layer, the first conductive plate and the second conductive plate.

The frame assemblies used with any of the prosthetic implants/valves herein can comprise a flexible stent post. The flexible stent post can be configured to provide at least partial support for one of the plurality of commissure supports. The power generator can be disposed on, disposed in, connected/attached to, integrated with, or otherwise associated with the stent post. The flexible stent post can comprise a protective covering housing a piezoelectric device therein. The prosthetic implant/valve can comprise a cloth layer that at least partially covers the power generator.

The prosthetic valves described above or elsewhere in this disclosure can be a transcatheter heart valve assembly or transcatheter heart valve. A transcatheter heart valve assembly can comprise a transcatheter heart valve. The transcatheter heart valve(s) can comprise a support frame that is radially collapsible for delivery in a catheter and expandable for deployment in an aorta of a patient. The support frame can comprise an interior surface and an exterior surface and a valve structure (e.g., a valve leaflet assembly, etc.) that is radially collapsible. The valve structure can comprise a plurality of valve leaflets secured to a plurality of respective commissure portions. The valve structure can be disposed within the support frame and fixed to the interior surface of the support frame. The transcatheter heart valve assembly or transcatheter heart valve can further comprise a sensor device (e.g., the same as or similar to sensor devices described above or elsewhere in this disclosure). The sensor device can be configured to sense a physical or physiological parameter and provide a sensor signal based on the sensed physical or physiological parameter. The transcatheter heart valve assembly or transcatheter heart valve can also include a transmitter assembly (e.g., the same as or similar to transmitter assemblies described above or elsewhere in this disclosure) electrically coupled to the sensor device. The transmitter assembly can be configured to receive the sensor signal from the sensor device and wirelessly transmit a transmission signal, wherein the transmission signal is based at least in part on the sensor signal (e.g., correlates, relates, is proportional, etc. to the sensor signal). The transmitter assembly can be tethered to the transcatheter heart valve assembly or to the transcatheter heart valve. For example, the transmitter assembly can be tethered to the support frame of the transcatheter heart valve. The transmitter assembly can comprise an antenna coil that is collapsible for catheter delivery. The transmitter assembly can be configured to wirelessly receive power from a power transmitter external to the patient.

The/a prosthetic implant (e.g., the same as or similar to the prosthetic implants/valves described above or elsewhere in this disclosure) can comprise a sensor device (e.g., the same as or similar to sensor devices described above or elsewhere in this disclosure) and a transmitter assembly (e.g., the same as or similar to transmitter assemblies described above or elsewhere in this disclosure). The prosthetic implant can include a frame assembly. Where the prosthetic implant is a prosthetic valve, the prosthetic valve can comprise a plurality of valve leaflets and a frame assembly configured to support the plurality of valve leaflets. The frame assembly of the prosthetic valve can comprise and define a plurality of commissure supports (e.g., commissure posts, commissure attachment structures, other support structures, etc.) that can be designed/shaped to terminate at or proximate an outflow end of the prosthetic valve. The prosthetic implant/valve can comprise an annular sealing ring disposed at an inflow end of the prosthetic implant/valve. The sensor device can be configured to sense a physical/physiological parameter and provide a sensor signal. The transmitter assembly can comprise a conductive coil having a plurality of windings. The transmitter assembly can be configured to receive the sensor signal from the sensor device and wirelessly transmit a transmission signal, wherein the transmission signal is based at least in part on the sensor signal (e.g., the transmission signal correlates, relates, is proportional, etc. to the sensor signal). The transmitter assembly can be disposed proximate the annular sealing ring or at another location on the prosthetic implant/valve.

The transmitter assembly can comprise a core form. The core form can be configured in a variety of ways. For example, the core form can be wrapped circumferentially around the prosthetic valve proximate to the sealing ring. The plurality of windings of the conductive coil can be circumferentially wrapped around the core form. Optionally, the plurality of windings can be axially wrapped around the core form. The core form can run along a portion of the annular sealing ring, and the plurality of windings can be circumferentially wrapped around the core form. The core form can be co-axial with an axis of the annular sealing ring. The core form can have an axial cross-sectional shape having three sides. The plurality of windings can lie in a plane facing radially outward with respect to the annular sealing ring. The core form can be disposed within the plurality of windings. The core form can be a magnetic core, an air core, another type of core, or a combination some or all of these. The core form and plurality of windings can be the same as or similar to other core forms and/or windings described elsewhere in this disclosure.

The/a prosthetic implant (e.g., the same as or similar to the prosthetic implants/valves described above or elsewhere in this disclosure) can comprise one or more electrodes. The prosthetic implant can comprise a frame assembly. Where the prosthetic implant is a prosthetic valve, the prosthetic valve can comprise a plurality of valve leaflets and a frame assembly configured to support the plurality of valve leaflets, and one or more electrodes. The frame assembly of the prosthetic valve can comprise and define a plurality of commissure supports (e.g., commissure posts, commissure attachment structures, other support structures, etc.) that can be designed/shaped to terminate at or proximate an outflow end of the prosthetic valve. The prosthetic implant/valve can comprise a first electrode that can be associated with the frame assembly and can be configured to detect an electrical impulse. The prosthetic implant/valve can also comprise a second electrode that can also be associated with the frame assembly and can be configured to detect the electrical impulse. The second electrode can be electrically coupled to the first electrode. The prosthetic implant/valve can also include additional electrodes which can be similar to the first electrode and/or the second electrode and that can also be electrically coupled. The prosthetic implant/valve can also include an amplifier configured to amplify a voltage difference between the first and second electrodes (and/or additional electrodes) and provide an amplified signal. The prosthetic implant/valve can also include transmitter assembly (e.g., the same as or similar to the transmitter assemblies described above or elsewhere herein) that can be configured to receive the amplified signal and wirelessly transmit a transmission signal, wherein the transmission signal is based at least in part on the amplified signal (e.g., the transmission signal correlates, relates, is proportional, etc. to the amplified signal).

The/a prosthetic implant (e.g., the same as or similar to the prosthetic implants/valves described above or elsewhere in this disclosure) can comprise a flow sensor (e.g., a blood flow sensor). Where the prosthetic implant is a prosthetic valve, the prosthetic valve can comprise a plurality of valve leaflets and a frame assembly configured to support the plurality of valve leaflets. The frame assembly of the prosthetic valve can comprise and define a plurality of commissure supports (e.g., commissure posts, commissure attachment structures, other support structures, etc.) that can be designed/shaped to terminate at or proximate an outflow end of the prosthetic valve. Optionally, the prosthetic implant/valve can comprise an annular sealing ring disposed at an inflow end of the prosthetic implant/valve. The prosthetic implant/valve can include or define a blood flow lumen (e.g., a frame, outer wall, the annular sealing ring, etc. can form, circumscribe, define, etc. a blood flow lumen). The flow sensor can be configured to sense a flow of blood in the blood flow lumen and generate a flow signal based on the flow.

The prosthetic implant/valve can further comprise a transmitter assembly that can be the same as or similar to the transmitter assemblies described above or elsewhere in this disclosure. The transmitter assembly can be configured to receive the flow signal and wirelessly transmit a transmission signal, wherein the transmission signal is based at least in part on the flow signal (e.g., the transmission signal correlates, relates, is proportional, etc. to the flow signal). The transmitter assembly can include an amplifier (e.g., with can be the same as or similar to the amplifiers described above or elsewhere herein) configured to amplify the flow signal. The transmitter assembly can include at least one filter configured to filter the flow signal. The prosthetic implant/valve can further comprise a second flow sensor, additional flow sensors, and/or other types of sensors.

The flow sensors described herein can be physically (e.g., directly) attached to a frame assembly and/or an annular sealing ring. For example, the flow sensors can be physically (e.g., directly) attached to a portion of an inner surface of the annular sealing ring in the blood flow lumen. The portion of the inner surface of the annular sealing ring where the flow sensor(s) is attached can be near a convergence point of two of the plurality of valve leaflets. The portion of the inner surface of the annular sealing ring where the flow sensor(s) is attached can also be at an intermediate region of one of the plurality of valve leaflets. Optionally, the flow sensor(s) can be physically (e.g., directly) attached to one or more of the plurality of valve leaflets of the prosthetic valve. The flow sensor can be physically (e.g., directly) attached to a portion of the one of the plurality of valve leaflets in proximity to a region of convergence of the one of the plurality of valve leaflets and another of the plurality of valve leaflets.

The/a prosthetic implant (e.g., the same as or similar to the prosthetic implants/valves described above or elsewhere in this disclosure) can comprise a flow sensor or sensors (e.g., the same as or similar to other flow sensors described above or elsewhere herein). Where the prosthetic implant is a prosthetic valve, the prosthetic valve can comprise a plurality of valve leaflets. The prosthetic implant/valve can include or define a blood flow lumen. Optionally, the prosthetic implant/valve can comprise an annular sealing ring disposed at an inflow end of the prosthetic implant/valve, and the annular sealing ring can form or define the blood flow lumen or a portion thereof. The flow sensor(s) can be configured to sense a flow of blood at an outflow side of the prosthetic implant/valve indicative of blood flow (e.g., of coronary blood flow). The flow sensor(s) can be physically (e.g., directly) attached to an outer surface of the annular sealing ring on an outflow side thereof or to another location (e.g., on the frame assembly). The flow sensor(s) can also be physically (e.g., directly) attached to one or more commissure supports of a frame assembly on an outflow side of the prosthetic valve.

The/a prosthetic implant (e.g., the same as or similar to the prosthetic implants/valves described above or elsewhere in this disclosure) can comprise an annular sealing ring disposed at an inflow end of the prosthetic implant/valve and a sensor device (e.g., the same as or similar to sensor devices described above or elsewhere herein). The prosthetic implant can comprise a frame assembly. Where the prosthetic implant is a prosthetic valve, the prosthetic valve can comprise a plurality of valve leaflets and a frame assembly configured to support the plurality of valve leaflets. The frame assembly of the prosthetic valve can comprise and define a plurality of commissure supports (e.g., commissure posts, commissure attachment structures, other support structures, etc.) that can be designed/shaped to terminate at or proximate an outflow end of the prosthetic valve. The sealing ring can have a circumferential channel formed therein. The sensor device can be configured to sense a physical or physiological parameter and provide a sensor signal. The prosthetic implant/valve can also include a transmitter assembly (e.g., the same as or similar to transmitter assemblies described above or elsewhere herein). The transmitter assembly can be configured to receive the sensor signal from the sensor device and wirelessly transmit a transmission signal, wherein the transmission signal is based at least in part on the sensor signal (e.g., the transmission signal correlates, relates, is proportional, etc. to the sensor signal). The transmitter assembly can include a ring-shaped electrically conductive coil embedded in the circumferential channel of the sealing ring. The electrically conductive coil can be configured to wirelessly transmit the transmission signal. The sensor device can be self-powered, such as through energy harvesting means and/or battery power.

A patient monitoring system can comprise a prosthetic implant/valve (e.g., the same as or similar to the prosthetic implants/valves described above or elsewhere in this disclosure). The prosthetic implant/valve can be an implant device and can be configured to be implanted in a patient and can comprise a sensor device (e.g., the same as or similar to sensor devices described above or elsewhere herein). Where the prosthetic implant is a prosthetic valve, the prosthetic valve can include a plurality of valve leaflets and a frame assembly configured to support the plurality of valve leaflets. The frame assembly of the prosthetic valve can comprise and define a plurality of commissure supports (e.g., commissure posts, commissure attachment structures, other support structures, etc.) that can be designed/shaped to terminate at or proximate an outflow end of the prosthetic valve. The sensor device can be a strain gauge device. In the prosthetic valve, the strain gauge device can be connected to (e.g., directly connected to), formed in or on, or otherwise associated with one (e.g., a first commissure support) of the plurality of commissure supports or another component of the prosthetic valve. The strain gauge device can be configured to provide a sensor signal indicating a deflection of the one (e.g., the first commissure support) of the plurality of commissure supports or other component of the prosthetic valve implant. In other prosthetic implants that do not include commissure supports, other supports or portions of a frame assembly can be used in a similar was to detect deflection. The prosthetic implant/valve can include a wireless transmitter assembly (e.g., the same as or similar to the transmitter assemblies described above or elsewhere herein). The transmitter assembly can have an antenna. The transmitter assembly can be configured to receive the sensor signal and wirelessly transmit a transmission signal, wherein the transmission signal is based at least in part on the sensor signal (e.g., the transmission signal correlates, relates, is proportional, etc. to the sensor signal). The patient monitoring system can further comprise a receiver device configured to wirelessly couple with the transmitter assembly or the antenna of the transmitter assembly of the prosthetic implant/valve. The receiver device can be configured to receive the transmission signal (e.g., receive the signal wirelessly) while the prosthetic implant/valve is implanted in a patient and the receiver device is located external to the patient.

Methods of monitoring a prosthetic implant/valve (e.g., the same as or similar to the prosthetic implants/valves described above or elsewhere in this disclosure) and/or monitoring a patient that has a prosthetic implant/valve can comprise wirelessly coupling an external receiver device to the/a prosthetic implant/valve implanted in the patient, measuring a physical/physiological parameter associated with the patient using a sensor device of the prosthetic implant/valve, and wirelessly transmitting a signal based on the measurement of the physical/physiological parameter using a transmitter assembly. In certain embodiments, the transmitter assembly includes a ring-shaped electrically conductive coil embedded in a sealing ring of the prosthetic implant/valve. In certain embodiments the method comprises powering the sensor device using energy harvesting means or battery power.

Methods of monitoring a prosthetic implant/valve (e.g., the same as or similar to the prosthetic implants/valves described above or elsewhere in this disclosure) and/or monitoring a patient that has a prosthetic valve implant can comprise wirelessly coupling an external receiver device to the/a prosthetic/implant valve implanted in the patient, measuring deflection or strain of one or more commissure supports or other portion(s)/component(s) of the prosthetic implant/valve using a strain gauge associated with the one or more commissure supports or other portion(s)/component(s) of the prosthetic valve implant device, wirelessly transmitting commissure deflection information based at least in part on the measured deflection to the external receiver device using a wireless transmitter assembly of the prosthetic implant/valve, and using the deflection information (e.g., commissure deflection information) to determine diagnostic information related to functioning of the prosthetic implant/valve. The diagnostic information can be related to one or more of: heart rate, systolic duration, diastolic duration, valve closing pressure, isovolumetric contraction, rate of change in pressure, blood flow, heart chamber pressure, cardiac vessel pressure, blood pressure, and other parameters.

A prosthetic implant/valve (e.g., the same as or similar to prosthetic implants/valves described above or elsewhere herein) can comprise a plurality of valve leaflets, a frame assembly configured to support the plurality of valve leaflets, an annular ring structure attached to the frame assembly and disposed at an inflow end of the prosthetic implant/valve, and/or a subset of these. The frame assembly of the prosthetic implant/valve can comprise and define a plurality of commissure supports (e.g., commissure posts, commissure attachment structures, other support structures, etc.) that can be designed/shaped to terminate at or proximate an outflow end of the prosthetic implant/valve. The sealing ring can have a circumferential channel formed therein, an electronic circuit, and a coil associated with a circumferential portion of the annular ring structure. The coil can be configured to receive electromagnetic energy, power the electric circuit and send and receive wireless data. Furthermore, the electronic circuit can be configured to sense one or more of a physiological parameter of a patient associated with the prosthetic implant/valve and a mechanical or functional parameter of the implant/valve. The electronic circuit can be further configured to communicate the sensed parameter (e.g., the physiological, mechanical, or functional parameter) to an external receiver unit.

A prosthetic annuloplasty ring can include features the same as or similar to those described with respect to prosthetic implants/valves described above or elsewhere herein. The prosthetic annuloplasty ring can comprise a ring structure (e.g., an annular sealing ring structure), and one or more electrodes (and/or another type of sensor device). For example, the prosthetic annuloplasty ring can comprise a first electrode that can be associated with the annular sealing ring structure and can be configured to detect an electrical impulse. The prosthetic annuloplasty ring can also comprise a second electrode that can be associated with the annular sealing ring structure and can be configured to detect the electrical impulse. The second electrode can be electrically coupled to the first electrode. The prosthetic annuloplasty ring can also include additional electrodes which can be similar to the first electrode and/or the second electrode and that can also be electrically coupled. The prosthetic annuloplasty ring can also include an amplifier configured to amplify a voltage difference between the first and second electrodes (and/or additional electrodes) and provide an amplified signal. The prosthetic annuloplasty ring can also include transmitter assembly (e.g., the same as or similar to the transmitter assemblies described above or elsewhere herein) that can be configured to receive the amplified signal and wirelessly transmit a transmission signal, wherein the transmission signal is based at least in part on the amplified signal (e.g., the transmission signal correlates, relates, is proportional, etc. to the amplified signal).

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIGS. 6A-6C, provide schematic and cross-sectional views, respectively, of capacitive sensors in accordance with one or more embodiments.

FIG. 7 is a block diagram illustrating an external local monitor system according to one or more embodiments.

FIG. 15 illustrates a stent member assembly according to one or more embodiments.

FIG. 16A provides a top view of a heart valve assembly according to one or more embodiments disclosed herein.

FIG. 16B is a cross-sectional view of the heart valve assembly of FIG. 16A according to one or more embodiments.

FIG. 16C shows an enlarged view of a portion of the cross-section of FIG. 16B according to one or more embodiments.

FIG. 20 provides a side view of a heart valve with an integrated commissure deflection sensor according to one or more embodiments.

FIG. 21 provides a perspective view of a stent member for an implant device according to one or more embodiments.

FIG. 37 provides a perspective view of a transcatheter heart valve and sensor assembly according to one or more embodiments.

FIG. 38 provides a perspective view of the transcatheter heart valve and sensor assembly of FIG. 37 in a compressed state according to one or more embodiments.

FIG. 45 illustrates an embodiment of a sensor-integrated valve implant device according to one or more embodiments.

DETAILED DESCRIPTION

Figure 1:
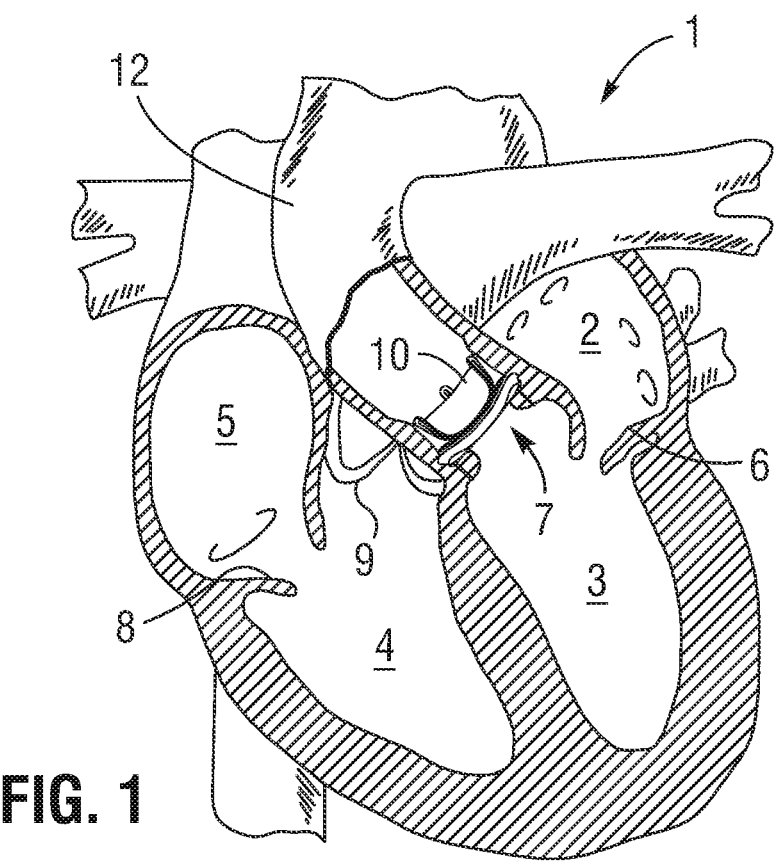
FIG. 1 provides a cross-sectional view of a heart having a surgical prosthetic heart valve implanted therein according to one or more embodiments.

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process can be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as may also be taught or suggested herein. Features described with respect to one exemplary embodiment may be incorporated into other embodiments disclosed herein even if not specifically described with respect to the embodiment.

Overview

In humans and other vertebrate animals, the heart generally comprises a muscular organ having four pumping chambers, wherein the flow thereof is at least partially controlled by various heart valves, namely, the aortic, mitral (or bicuspid), tricuspid, and pulmonary valves. The valves can be configured to open and close in response to a pressure gradient present during various stages of the cardiac cycle (e.g., relaxation and contraction) to at least partially control the flow of blood to a respective region of the heart and/or to blood vessels (e.g., pulmonary trunk, aorta, etc.).

Heart valves may generally comprise a relatively dense fibrous ring, referred to herein as the annulus, as well as a plurality of leaflets or cusps attached to the annulus. Some valves can further comprise a collection of chordae tendineae and papillary muscles securing the leaflets. Generally, the size of the leaflets or cusps may be such that when the heart contracts the resulting increased blood pressure produced within the corresponding heart chamber forces the leaflets to at least partially open to allow flow from the heart chamber. As the pressure in the heart chamber subsides, the pressure in the subsequent chamber or blood vessel may become dominant, and press back against the leaflets. As a result, the leaflets/cusps may come in apposition to each other, thereby closing the flow passage.

Heart valve disease represents a condition in which one or more of the valves of the heart fail to function properly. Diseased heart valves can be categorized as stenotic, wherein the valve does not open sufficiently to allow adequate forward flow of blood through the valve, and/or incompetent, wherein the valve does not close completely, causing excessive backward flow of blood through the valve when the valve is closed. In certain conditions, valve disease can be severely debilitating and even fatal if left untreated.

Various surgical techniques can be used to replace or repair a diseased or damaged valve, including securing a prosthetic cardiac implant to the annulus of the diseased or damaged valve. Prosthetic cardiac implants can include mechanical prosthetic heart valves, valved conduits, annuloplasty rings, stents, grafts, etc. In a valve replacement operation, damaged leaflets can be excised and the annulus sculpted to receive a replacement valve.

Prosthetic heart valves can be composed of various synthetic and/or biologically-derived materials/tissues. Prosthetic heart valves can be implanted independently in one of the orifices or annuluses of the heart, or can be otherwise coupled to a flow conduit which extends in line with the valve. For example, valved conduits can be designed for reconstruction of portions of the flow passage above and below the aortic valve, such as the ascending aorta, in addition to replacing the function of the valve itself. Introduction of the sensors into the patient system can be through surgical or minimally-invasive means.

Patients who receive heart valve implants may suffer from post-operation complications. For example, a patient may be particularly susceptible to complications within thirty or sixty days following an implant operation. However, during such periods of time, the patient may no longer be in a hospital or extended care facility/system, and therefore complications that arise may require reentry into the care facility/system, potentially adding significant cost to the overall patient treatment. Furthermore, increased health risks may result from the patient delaying return to the hospital due to failure to recognize the complications until they manifest through perceivable symptoms that the patient interprets as requiring hospital care.

Disclosed herein are systems, devices and methods for post-operatively monitoring prosthetic heart valve implant recipients, including possibly in an environment outside of the relevant hospital or care facility. Certain embodiments disclosed herein provide a heart valve device/system including integrated sensing capability for sensing one or more conditions of the heart valve and/or heart of a patient. The heart valve can be configured to wirelessly communicate such sensed parameters (e.g., critical patient issues) from the sensor system in the valve to a local or remote wireless receiver device, which can be carried by the patient in some embodiments. The receiver can be configured to communicate information associated with the received sensor information to a care provider system, such as to a remote hospital or care facility monitoring system. Sensor-integrated implant devices in accordance with principles disclosed herein can include surgical valves (e.g., aortic or mitral), transcatheter heart valves (THVs), annuloplasty rings (e.g., mitral, tricuspid), pacemakers (e.g., in connection with electrical leads), or the like, or can alternatively be applicable to stand-alone sensor devices that are not integrated with a valve or other implant device.

Physiological parameters that can be tracked by sensor-enabled heart valve implants can include arrhythmia, blood pressure, cardiac output (e.g., as measured by an echo sensor, induction, ballistocardiogram, or the like), and/or other parameter(s). Furthermore, implant devices disclosed herein can incorporate any desired or practical types of sensors, such as strain gauges, pressure sensors, optical sensors, audio sensor, position sensors, acceleration sensors, or other type(s) of sensor. Integrated implant sensors can advantageously be configured to generate electrical signals that can be wirelessly transmitted to a receiver device (e.g., box) disposed outside the patient's body. In certain embodiments, the receiver device is configured to forward information based at least in part on the signals to a remote care giver system/entity.

In certain embodiments, sensor devices associated with implant devices may sense pressure and/or electrical activity. For example, pressure can provide information regarding how well the implant is functioning, as well as possibly information regarding hydration. Electrical activity sensor(s) can provide information used to detect arrhythmia or other condition. Pressure sensors integrated in devices in accordance with the present disclosure can include micro-electromechanical (MEMS) devices (e.g., accelerometer), which can be integrated in the implant frame, for example. In certain embodiments, two or more sensors can be utilized. As an example, a plurality of sensors can be used to measure differential pressure between the inflow and outflow ends of a valve implant, which can provide information indicating regurgitation.

Sensors and/or transmitters integrated in implant devices according to embodiments of the present disclosure may only need to operate for a limited monitoring period of time (e.g., 90 to 120 days), and can therefore be powerable using a battery, such as a lithium ion or magnesium-based battery. For example, a battery can use a piece of magnesium as a cathode in at least partial contact with body fluid(s) (e.g., blood), which may degrade as it generates electrical power. In certain embodiments, an external power source configured to provide power through induction, radio frequency (RF) transmission, or other type of wireless power transmission can be used. In certain embodiments, an internal rechargeable battery or capacitor (e.g., supercapacitor) can be used for limited power storage between charging. Such a power transmitter can be integrated with an external data receiver. In certain embodiments, a portion of the frame of the implant/sensor device can be used as an antenna for power transmission. Additionally or alternatively, the patient's body movement can be used to generate power, such as by using one or more piezoelectric MEMS devices (e.g., strain gauge, accelerometer).

Certain embodiments of implantable sensor devices comprise energy harvesting feature(s) for generating power for sensor operation and/or data transmission from environmental conditions. For example, an implantable sensor device, such as a prosthetic heart valve having a sensor associated therewith, can comprise or be associated with a piezoelectric sensor or device, or other passive power generator, wherein the piezoelectric sensor/device is configured to generate an electrical signal in response to fluid pressure or other external stimulus. The piezoelectric sensor can advantageously be integrated with one or more structural features of a prosthetic valve implant, such as a commissure post or associated feature. The power generated by the sensor may be sufficient to power the functionality of the implant-integrated physiological sensor, or may serve to supplement another power source, which can be internal or external.

In certain embodiments, implant-integrated sensor devices can be configured to run substantially continuously. Alternatively, the sensor(s) can run only for predetermined intervals, which may provide power savings compared to continuous operation. In certain embodiments, controller logic can be integrated with the implant/sensor for determining timing and/or duration of operation based on measured conditions. In certain embodiments, the sensor(s) can operate only when wirelessly coupled with an external data/power communication device. In embodiments in which the sensor(s) collect data even when the device is not coupled to an external device, it may be necessary or desirable for the implant/sensor to include data storage, such as flash memory, memristor(s), or other low-power memory, for storing collected data in interim periods of time.

Certain embodiments operate in connection with an external power/data transfer device, which can advantageously be small enough to be carried with by the patient (e.g., continuously), such as by using a chest strap, or the like. In certain embodiments, the external device comprises a patch or band with one or more antennae for input/output (I/O) and/or power; remaining circuitry may be contained in a separate box or device. In certain embodiments, the external device can comprise an arm-strap fitted device, a chest-strap fitted device, or a device that can fit in the patient's pocket. Bluetooth, near-field communication (NFC), or other low-power technology or protocol can be used to connect the external device and/or implant/sensor to a smartphone or other computing device to transmit data to a hospital or other data aggregator. In certain embodiments, the external device can comprise a mat designed to be located at or near a bed; the mat can collect data and transmit the data while the patient is sleeping, for example.

Certain embodiments disclosed herein provide a laminated piezoelectric-polymer electricity generator integrated onto prosthetic heart valves for harvesting energy from blood flow-induced vibrations and movement of support frames to power electronic implantable medical devices, such as blood-pressure sensors, blood glucose meters, pacemakers, and the like.

Prosthetic Implants

Embodiments of implant/valve monitoring devices and systems disclosed herein can be applicable with respect to any type of implant/valve (e.g., any type of heart valve, bio-compatible implant, annuloplasty ring, stent, graft, etc.), whether implanted using surgical or transcatheter means. While much of the disclosure focuses on examples of prosthetic valves or prosthetic heart valves, the principles, concepts, and features can be applied to other prosthetic implants of a variety of types and be use in a variety of methods involving prosthetic valves or other prosthetic implants.

FIG. 1 provides a schematic drawing of a surgical prosthetic heart valve 10 implanted in a heart 1 according to one or more embodiments. Although the illustrated valve 10 is an aortic valve implant, it should be understood that the various features and embodiments disclosed herein relating go implant devices having sensor and/or transmission functionality can be applicable to any type of implant device, including but not limited to, mitral valves, tricuspid valves, pulmonary valves, implants of the inferior or superior vena cava or pulmonic trunk, venus valves, etc. In certain embodiments, the heart valve 10 can include one or more sensors (not shown) for measuring/sensing one or more physiological parameters, as described herein. The heart valve 10 can further include means for wirelessly transmitting signals associated with the sensor response to an external receiver device, wherein such means can include a wireless transmitter or transceiver, for example.

The heart valve 10 can function to allow fluid flow in one direction, such as out of the heart with respect to an aortic heart valve, while inhibiting fluid flow in the opposite direction. The heart 1 includes four chambers, namely the left atrium 2, the left ventricle 3, the right ventricle 4, and the right atrium 5. The heart 1 further includes four valves for aiding the circulation of blood therein, including the tricuspid valve 8, which separates the right atrium 5 from the right ventricle 4. The tricuspid valve 8 may generally have three cusps or leaflets and may generally close during ventricular contraction (i.e., systole) and open during ventricular expansion (i.e., diastole). The pulmonary valve 9 separates the right ventricle 4 from the pulmonary artery, and can be configured to open during systole so that blood can be pumped towards the lungs, and close during diastole to prevent blood from leaking back into the heart from the pulmonary artery. The pulmonary valve 9 has three cusps/leaflets, each one resembling a crescent. The mitral valve 6 has two cusps/leaflets and separates the left atrium 2 from the left ventricle 3. The mitral valve 6 is configured to open during diastole so that blood in the left atrium 2 can flow into the left ventricle 3, and close during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

Figure 2:
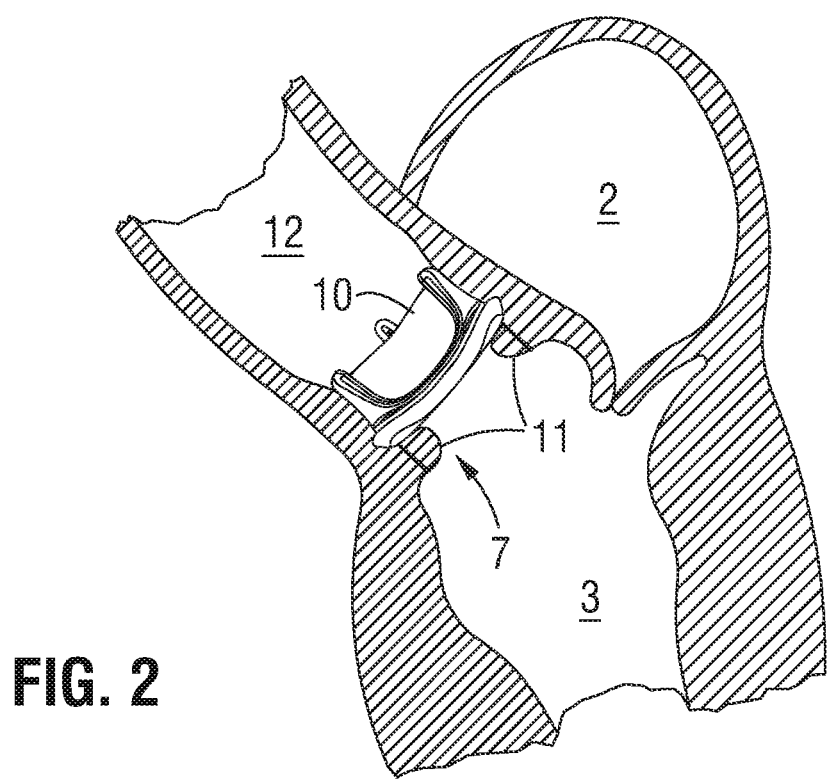
FIG. 2 provides an enlarged view of the aortic valve shown in FIG. 1.

The heart valve 10 represents an exemplary surgical prosthetic heart valve, which is shown implanted in the aortic valve 7. However, it should be understood that heart valves as disclosed herein can be any type of heart valve (e.g., aortic valve, mitral valve, tricuspid valve, and/or pulmonary valve) and the description can apply to other types of prosthetic implants as well. FIG. 2 provides an enlarged view of the aortic valve 7 shown in FIG. 1. The aortic valve 7 includes an aortic annulus 11, which comprises a fibrous ring extending inward as a ledge into the flow orifice, and can be seen with the prosthetic heart valve 10 disposed thereon (e.g., sutured thereto). Prior to valve replacement, the native leaflets may extend inward from the annulus 11 and come together in the flow orifice to permit flow in the outflow direction (e.g., the upward direction in FIG. 2) and prevent backflow or regurgitation toward the inflow direction (e.g., the downward direction in FIG. 2).

In a surgical cardiac implant procedure, the aorta can be incised and, in a valve replacement operation, the defective valve can be removed leaving the desired placement site that may include the valve annulus. Sutures may be passed through fibrous tissue of the annulus or desired placement site to form an array of sutures. Free ends of the sutures can be individually threaded through a suture-permeable sealing edge of the prosthetic heart valve. Transcatheter cardiac implant procedures can involve delivering a prosthetic valve percutaneously, and the valve may be able to transition from a collapsed configuration during delivery to an expanded configuration when it is implanted. Similar techniques can be used with other prosthetic implants, e.g., in other locations.

Patient Monitoring

The efficacy of an implanted prosthetic heart valve can be measured based on the measurements of pressure, fluid flow through the valve, and/or other mechanisms that can provide indications of cardio output and/or heart function in general. Acute monitoring of heart/valve performance can be performed in a variety of ways, such as through the use of echo-based technologies (e.g., ultrasound, etc.) to measure the speed of fluid flow through the valve, which can be used to derive other calculations, such as pressure gradient, and the like. Imaging technologies (e.g., CT scan or X-ray) can provide information related to the opening/closing of heart valves, which can be used to determine blood volumes, etc.

When an individual has experienced compromised heart function over a period of time, transition to a new prosthetic heart valve may be somewhat prolonged. Therefore, although acute heart/valve monitoring may be performed during and immediately after surgery, continued monitoring of heart/valve function over a prolonged period of time post-surgery can be necessary or desirable. In addition, implant patients are often prescribed various medication dosages to assist in the recovery process. However, improper dosages can manifest in heart/valve complications that should be resolved as soon as possible.

Therefore, for at least these reasons, post-operative monitoring (e.g., continuous monitoring) over a period of time, such as for 15 days, 30 days, 45 days, 60 days, 90 days, or some other period post operation, may be desirable. For example, continued monitoring can provide the opportunity to intervene in the patient's recovery, such as by changing medication/dosage, before symptoms of malfunction manifest, and therefore earlier detection and response can be possible. Possible complications from heart valve implant surgery can include decreased ejection fraction, undesirable changes in pressure or pressure regulation malfunction, irregular heart rhythm (e.g., caused by surgical incisions), as well as other conditions. Certain embodiments provide a heart valve configured with one or more sensors for monitoring parameters related to such conditions, as well as a mechanism for communicating such information to one or more external systems and/or subsystems.

Wireless Monitoring System

As described in detail above, patients who receive heart valve implants can experience relatively late complications (e.g., between 30-60 days, or within 90 days of surgery). At such point in the recovery process, a patient may have left the hospital or extended care system, and therefore arising complications can require reentry of the patient into the care system, potentially adding significant cost to the overall patient treatment. Disclosed herein are patient monitoring devices and systems, such as including a prosthetic heart valve with integrated sensor and wireless communication technology, that allow for the communication of critical patient issues from an implanted device to one or more external devices/systems that can be utilized by care givers and/or patients in the treatment of a patient. For example, a replacement heart valve device can incorporate one or more relatively small sensors, which can be incorporated with the valve or other implant, or otherwise associated therewith.

Figure 3:
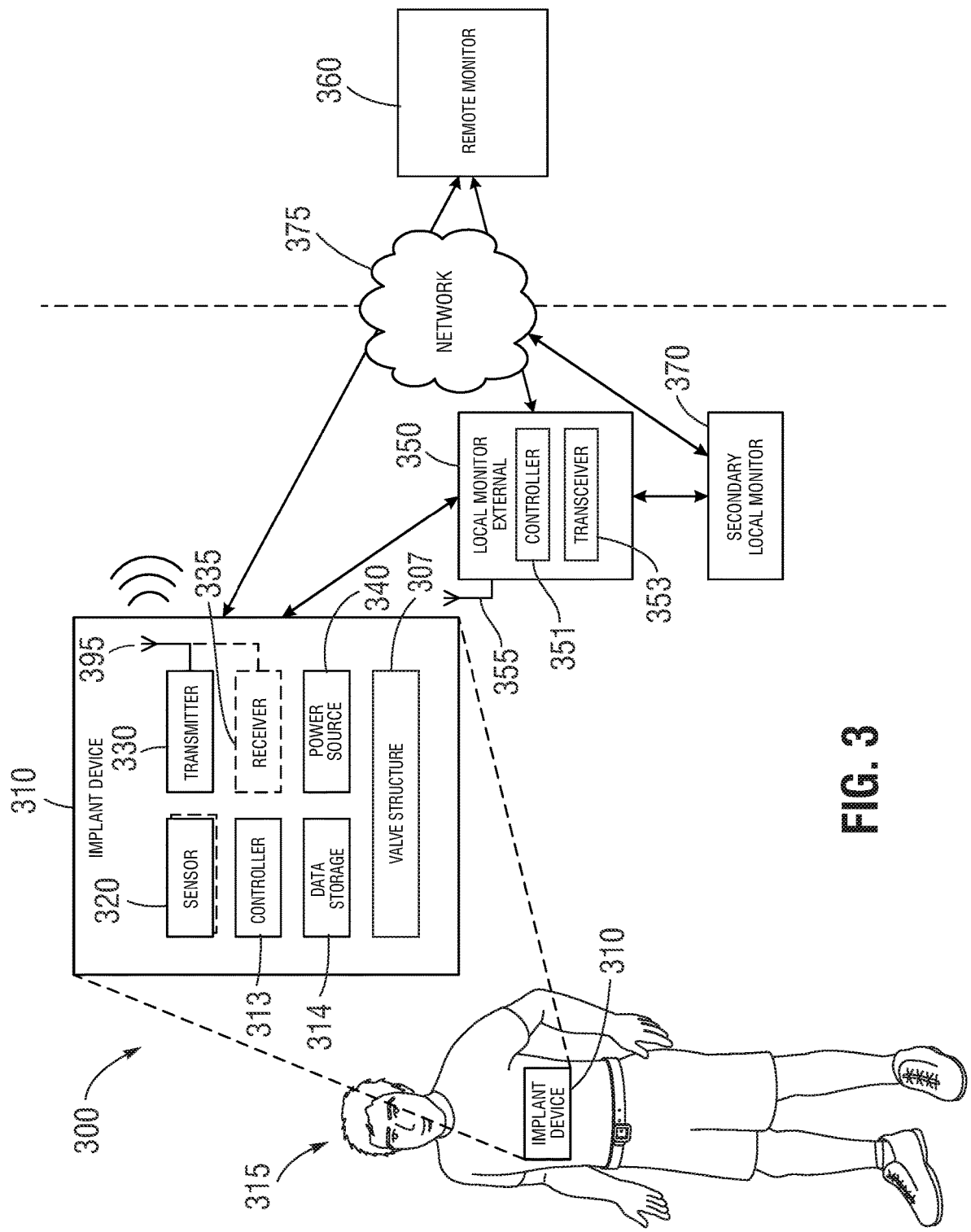
FIG. 3 illustrates a system for monitoring the on-going health of an implant patient according to one or more embodiments.

FIG. 3 shows a system 300 for monitoring the on-going health of a patient 315 according to one or more embodiments. The patient 315 can have an implant device 310 implanted in, for example, the heart (not shown), or associated physiology, of the patient. For example, the implant device 310 can be a prosthetic heart valve, such as an aortic heart valve, as described in detail herein. The implant device 310 can include one or more sensor devices 320, such as one or more microelectromechanical system (MEMS) devices, such as MEMS pressure sensors, or the like.

In certain embodiments, the monitoring system 300 can comprise at least two sub-systems, including an implantable internal sub-system that includes a replacement heart valve integrated with one or more physiological parameter sensors (e.g., MEMS pressure sensor(s)), as well as one or more microcontroller(s), discrete electronic component(s), and power and/or data transmitter(s) (e.g., antennae coil). The monitoring system 300 can further include an external (e.g., non-implantable) sub-system that includes matching external receiver (e.g., coil) electrically and/or communicatively coupled to a patient/physician controller or monitor device. In certain embodiments, both the internal and external sub-systems include a corresponding coil antennae for wireless communication and/or power delivery through patient tissue disposed therebetween.

The implant device 310 can be any type of implant device. For example, the implant device 310 can be a heart valve, such as a Magna Mitral Ease valve, produced by Edwards Lifesciences. In certain embodiments, the implant device 310 provides a passive implant that functions as replacement heart valve, wherein the valve is integrated with capability for monitoring certain local cardiac functions and/or metrics.

Certain details of the implant device 310 are illustrated in the enlarged block 310 shown. The implant device 310 can comprise valve structural features or components 307 as described herein. For example, the valve structure 307 can include one or more leaflets, frames, bands, rings, and/or the like, such as may be consistent with a prosthetic aortic valve device as described herein. In certain embodiments, one or more of the other components of the implant device 310 can be integrated with the physical structure 307 of the implant device 310. For example, one or more antennas, transmission lines, coils, wires, or the like can be integrated with a rigid structure of the implant device, such as a sealing ring or frame of the device 310.

Although certain components are illustrated in FIG. 3 as part of the implant device 310, it should be understood that the implant device 310 may only comprise a subset of the illustrated components/modules, and can comprise additional components/modules not illustrated. The implant device 310 includes one or more sensors 320, which can be configured to provide a response indicative of one or more physiological parameters of the patient 315, such as one or more parameters associated with the function/integration of the implant device and the associated organ/member of the patient 315 (e.g., heart). The sensor(s) 320 can comprise any suitable or desirable sensor(s) for providing signals relating to physiological parameters or conditions associated with the implant device 310. In view of the integrated sensor(s) 320, the implant device 310 can advantageously provide sensor capability without the necessity of a separate, stand-alone device that requires a separate procedure to implant.

In certain embodiments, the sensor(s) 320 comprises a pressure sensor, such as a pulmonary artery pressure (PAP) measurement device. The sensor(s) 320 can additionally or alternatively comprise one or more optical sensors, piezoelectric sensors, electromagnetic sensors, strain sensors/gauges, accelerometers, gyroscopes, and/or other types of sensors, which can be positioned in the patient 315 to sense one or more parameters relevant to the function of the implant device. Sensor signals can be used to track arrhythmia, blood pressure, cardiac output (e.g., as measured by an echo sensor), induction or ballistocardiogram. In an embodiment, the sensor(s) 320 comprise a MEMS pressure sensor, which can be either capacitive or piezoresistive in nature, wherein the sensor is coupled with an application-specific integrated circuit (ASIC) microcontroller. The sensor(s) 320 can be attached to a polyimide flexible circuit substrate, and can be further accompanied with one or more discrete electronic components, such as tuning capacitors or the like. In certain embodiments, the sensor(s) 320 comprise one or more electrodes for detecting electrical impulses originating in the heart.

In certain embodiments, the sensor(s) 320 can be configured to generate electrical signals that can be wirelessly transmitted to a box/device outside the patient's body, such as the illustrated local monitor device/system 350. In order to perform such wireless data transmission, the implant device 310 can include radio frequency (RF) transmission circuitry, such as a transmitter 330 including an antenna 395. The antenna 395 can comprise an internal antenna coil implanted within the patient. The transmitter 330 can comprise any type of transducer configured to radiate or transmit an electromagnetic signal, such as a conductive wire, coil, plate, or the like. With respect to embodiments comprising pressure sensor(s), the voltage change due to the changes in the pressure sensitive element(s) (e.g., capacitance) can be at least somewhat attenuated due to variability in inductive coupling between the implant device 310 and a coupled external antenna 355. Such signal attenuation can at least partially limit the placement of the sensor(s) 320 to locations associated with relatively less intense or frequent physiological movement.

The wireless signals generated by the implant device 310 can be received by the local external monitor device or subsystem 350, which can include a transceiver module 353 configured to receive the wireless signal transmissions from the implant device 310, which is disposed at least partially within the patient 315. The external local monitor 350 can receive the wireless signal transmissions and/or provide wireless power using an external antenna 355, such as a coil. The transceiver 353 can include RF front-end circuitry configured to receive and amplify the signals from the sensor(s) 320, wherein such circuitry can include one or more filters (e.g., band-pass filters), amplifiers (e.g., low-noise amplifiers), analog-to-digital converters (ADC) and/or digital control interface circuitry, phase-locked loop (PLL) circuitry, signal mixers, or the like. The transceiver 353 can further be configured to transmit signals over a network 375 to a remote monitor subsystem or device 360. The RF circuitry of the transceiver 353 can further include one or more of digital-to-analog converter (DAS) circuitry, power amplifier(s), low-pass filters, antenna switch modules, antennas or the like for treatment/processing of transmitted signals over the network 375 and/or for receiving signals from the implant device 310. In certain embodiments, the local monitor 350 includes controller circuitry for performing processing of the signals received from the implant device and/or controlling operation of the RF circuitry. The local monitor 350 can be configured to communicate with the network 375 according to a known network protocol, such as Ethernet, Wi-Fi, or the like. In certain embodiments, the local monitor 350 is a smartphone, laptop computer, or other mobile computing device, or any other type of computing device.

The implant device 310 can include controller circuitry 313, which can comprise, for example, one or more chips or dies configured to perform some amount of processing on signals generated and/or transmitted using the device 310. However, due to size, cost, and/or other constraints, the implant device 310 may not include independent processing capability in some embodiments.

In certain embodiments, the implant device includes a data storage module 314, which can comprise some amount of volatile and/or non-volatile data storage. For example, the data storage 314 can comprise solid-state memory utilizing an array of floating-gate transistors, or the like. The controller circuitry 313 can utilize the data storage module 314 for storing sensed data collected over a period of time, wherein the stored data can be transmitted periodically to the local monitor 350 or other external subsystem. In certain embodiments, the implant device 310 does not include any data storage. As described above, the implant device 310 is configured with transmitter circuitry 330 for the purpose of wirelessly transmitting data generated by the sensor(s) 320, or other data associated therewith. The implant device 310 can further comprise receiver circuitry 335, for receiving input from one or more external subsystems, such as from the local monitor 350, or from a remote monitor 360 over, for example, the network 375. For example, the implant device 310 can receive signals that at least partially control the operation of the implant device 310, such as by activating/deactivating one or more components or sensors, or otherwise affecting operation or performance of the implant device 310.

The one or more components of the implant device 310 can be powered by one or more power sources 340. Due to size, cost and/or electrical complexity concerns, it may be desirable for the power source 340 to be relatively minimalistic in nature. For example, high-power driving voltages and/or currents in the implant device 310 can adversely affect or interfere with operation of the implant device and/or heart or other body part associated with the implant device. In certain embodiments, the power source 340 is at least partially passive in nature, such that power can be received from an external source wirelessly by passive circuitry of the implant device 310, such as through the use of short-range, or near-field wireless power transmission, or other electromagnetic coupling mechanism. For example, the local monitor 350 can serve as an initiator that actively generates an RF field that can provide power to the implant device 310, thereby allowing the power circuitry of the implant device to take a relatively simple form factor. In certain embodiments, the power source 340 can be configured to harvest energy from environmental sources, such as fluid flow, motion, or the like. Additionally or alternatively, the power source 340 can comprise a battery, which can advantageously be configured to provide enough power as needed over the monitoring period (e.g., 30, 60, or 90 days, or other period of time).

The local monitor device 350 can serve as an intermediate communication device between the implant device 310 and the remote monitor 360. The local monitor device 350 can be a dedicated external unit designed to communicate with the implant device 310. For example, the local monitor device 350 can be a wearable communication device, or other device that can be readily disposed in proximity to the patient 315 and implant device 310. The local monitor device 350 can be configured to continuously, periodically or sporadically interrogate the implant device 310 in order to extract or request sensor-based information therefrom. In certain embodiments, the local monitor 350 comprises a user interface, wherein a user can utilize the interface to view sensor data, request sensor data, or otherwise interact with the local monitor device 350 and/or implant device 310.

The system 300 can include a secondary local monitor 370, which can be, for example, a desktop computer or other computing device configured to provide a monitoring station or interface for viewing and/or interacting with the monitor data. In an embodiment, the local monitor 350 can be a wearable device or other device or system configured to be disposed in close physical proximity to the patient and/or implant device 310, wherein the local monitor 350 is primarily designed to receive/transmit signals to and/or from the implant device 310 and provide such signals to the secondary local monitor 370 for viewing, processing, and/or manipulation thereof.

The remote monitor subsystem 360 can be any type of computing device or collection of computing devices configured to receive, process and/or present monitor data received over the network 375 from the local monitor device 350, secondary local monitor 370, or implant device 310. For example, the remote monitor subsystem 360 can advantageously be operated and/or controlled by a healthcare entity, such as a hospital, doctor, or other care entity associated with the patient 315. Although certain embodiments disclosed herein describe communication with the remote monitor subsystem 360 from the implant device indirectly through the local monitor device 350, in certain embodiments, the implant device 310 can comprise a transmitter capable of communicating over the network 375 with the remote monitor subsystem 360 without the necessity of relaying information through the local monitor device 350.

Implantable Sensor

Figure 4:
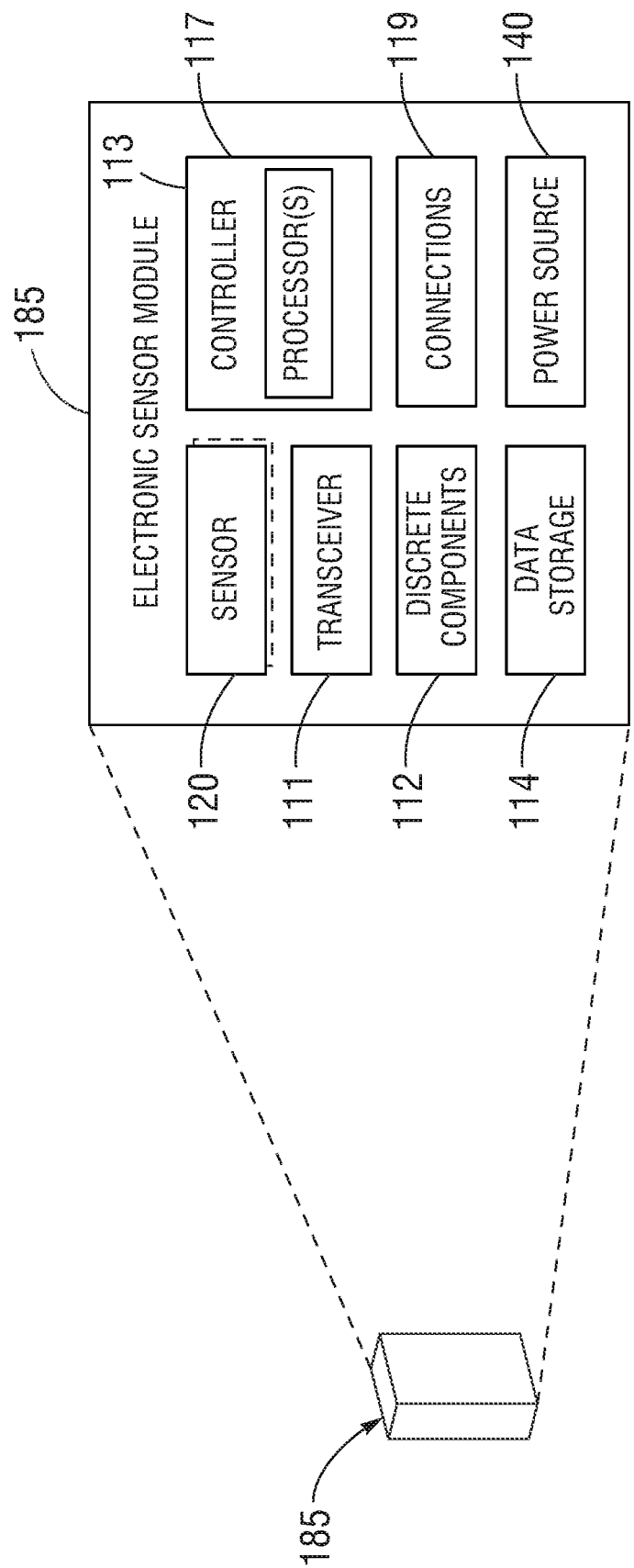
FIG. 4 is a block diagram representing an implantable sensor device according to one or more embodiments.

FIG. 4 is a diagram of an implantable sensor device according to one or more embodiments disclosed herein. The sensor device 185 can take the form of a microchip (e.g., Application-Specific Integrated Circuit (ASIC)) having one or more electrical devices or components housed within an exterior housing, which can be rectangular or have any other shape. In certain embodiments, the sensor device 185 can comprise a MEMS pressure sensor that is configured to be exposed to blood flow proximal to a valve implant and sense pressure variations associated with the change in flow velocity. For example, according to Bernoulli's principle, an increase in the speed of a fluid can occur simultaneously with a decrease in pressure. Therefore, for a MEMS pressure sensor device, the varying fluid pressure of the blood flow in contact therewith can cause the membrane/diaphragm element of the pressure chamber/cavity of the MEMS pressure sensor to deflect by some amount. In some embodiments, the sensor module 185, and/or one or more components thereof, can be coated with a biocompatible protective coating, such as a silver ion coating, or the like. However, certain coatings may interfere with radio-frequency transmission signals and/or electrical circuitry, and may therefore be undesirable in some implementations.

Figure 5A:
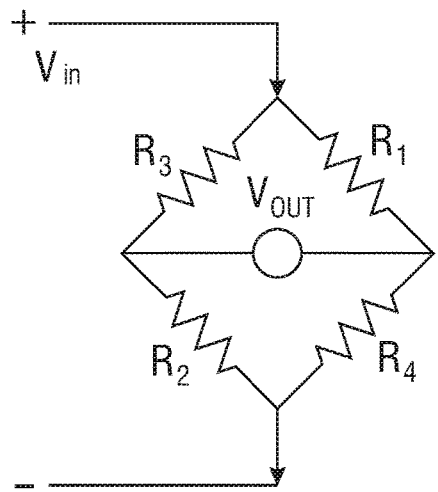
FIGS. 5A-5C provide schematic, plan, and cross-sectional views, respectively, of resistive sensor devices in accordance with one or more embodiments.
Figure 5B:
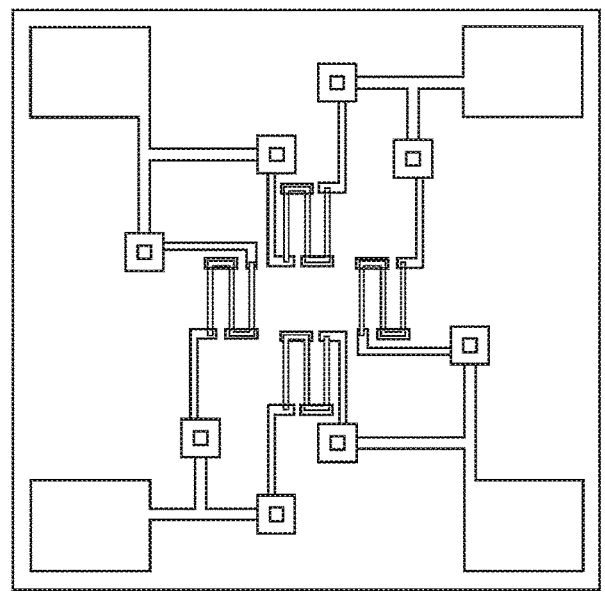
Figure 5C:
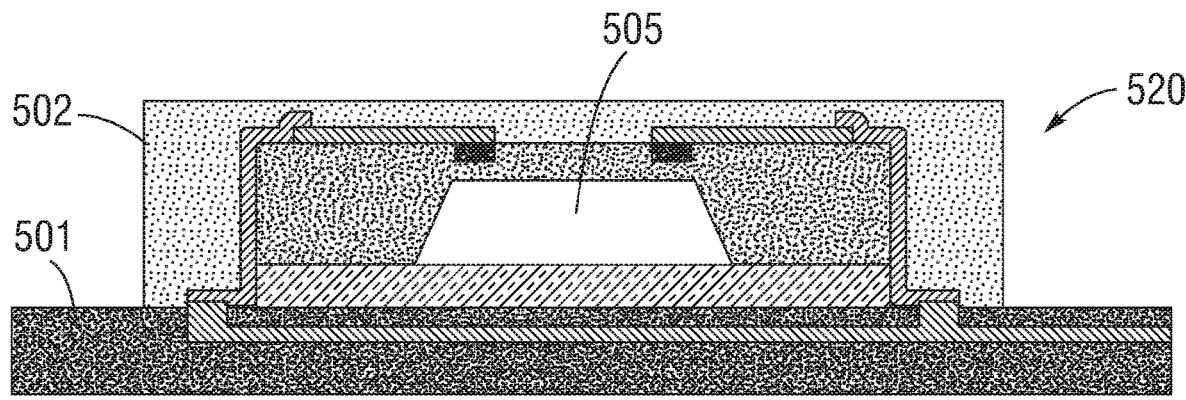

FIGS. 5A-5C provide schematic, plan, and cross-sectional views of resistive sensors, respectively, in accordance with one or more embodiments disclosed herein. For piezoresistive-type sensors, pressure-induced deflection can induce changes in the resistance in the piezoresistive element(s) and thus a voltage change. In certain embodiments, the piezoelectric elements can be created at least in part through ion-implantation of bromine (Br). Compared to certain capacitive sensors, piezoresistive sensors in accordance with certain embodiments disclosed herein can provide a relatively smaller physical footprint and/or provide a relatively more linear input-output relationship.

FIGS. 6A-6C, provide schematic and cross-sectional views of capacitive sensors, respectively, in accordance with one or more embodiments disclosed herein. For capacitive-type sensors, the deflection can induce changes in the dielectric distance between parallel conductive capacitor plates and thus a voltage change. The capacitive sensor 620 can be manufactured using a substrate 601 (e.g., silicon wafer) for structural support for fabrication and handling. In certain embodiments, biomedical-grade silicone elastomer or other biocompatible medium 602 can be used to encapsulate the electrically active elements of the device 620, and can be deposited using spin coating or other application process. One or more additional layers (not shown) can additionally be used/deposited to provide additional protection from moisture, debris or the like. Metallization 603 for the device 620 can comprise gold (Au) or other electrically-conductive materials, such as titanium, platinum, copper, or the like. The metallization can provide a first electrically conductive layer 604, followed by the addition of a layer of piezoelectric material 605. A second electrically conductive layer 606 can be applied on top of the piezoelectric material 605. In certain embodiments, monocrystalline and/or polycrystalline silicon, or other substrate material, can be formed between the piezoelectric material 605 and the second conductive plate 606. The metal-piezoelectric-metal layer structure can provide the pressure sensor functionality.

For either resistive or capacitive sensors, the chamber of the sensor device can be filled with inert gas (e.g., argon (Ar), xenon (Xe), etc.) or compressible dielectric material (e.g., low-durometer polymers, such as silicone, etc.). With further reference to FIG. 4, in certain embodiments, the sensor device 185 and/or controller 113 associated therewith can be fabricated at least in part using complementary metal-oxide-semiconductor (CMOS) photolithography processes. Suitable substrate materials for the sensor can include silicon dioxide ($SiO_2$), silicon nitride (e.g., $Si_3N_4$), sapphire, glass, polyimide, or the like. Suitable materials for metallization and/or interconnect wire bonding can include platinum (Pt), platinum iridium (Pt/Ir), gold (Au), or the like.

The sensor device/module 185 can include a covering or housing providing biocompatibility and/or increased protection of internal sensor elements/circuitry and/or discrete component(s). For example, the housing/cover can comprise one or more of silicone, parylene, fluorocarbons (e.g., FEP, FTPE, etc.), hydrophilic or hydrophobic coatings, or ceramic coatings such as alumina, zirconia, DLC, ultrananocrystaline diamond, or combinations thereof, which can be applied as coatings or physical structural components.

The controller 113 and/or transceiver 111 can receive the sensor signal from the sensor 120 and perform preliminary signal processing and/or digitization. For example, the sensor(s) 120 can provide a voltage differential analog signal (e.g., generated by a MEMS pressure sensor or electrode). The sensor module 185 can further comprise one or more other discrete electrical components 112, such as tuning capacitors or the like, and/or one or more amplifiers (e.g., low-noise amplifier(s)). The substrate (e.g., polyimide) holding the sensor(s), control circuitry, discrete components, and/or other component(s) of the module 185 can be further attached to certain physical structural components of the implant device, such as a stent portion of a valve implant along either the inner surface of the orifice, or the outer surface of the valve.

The electronic sensor module 185 can be coupled to an antenna (not shown), such as a coiled antenna, which can be connected to, for example, the substrate and attached to the sewing ring portion of the valve near the inflow aspect of the valve. Suitable material for the coil antennae can be gold (Au), platinum (Pt), platinum iridium (Pt/Ir), or the like. Such materials can provide relatively soft/ductile coil wiring. In certain embodiments, a composite wire with a core made of more rigid material, such as nickel-cobalt alloy (e.g., MP35N alloy, Fort Wayne Metals), cobalt-chromium alloy (e.g., Elgiloy alloy, Elgiloy Specialty Metals), or nitinol.

The components of the sensor module 185, such as the sensor(s) 120, controller 113, transceiver 111, discrete component(s) 112, and/or data storage 114 can be powered by a power source 140, which can comprise an inductively-powered internal coil antennae configured to receive radio frequency (RF) energy from an external source (e.g., the external local monitor 350 of FIG. 3). In certain embodiments, RF induction can be used to provide a means of bi-directional data communication between the controller 113 of the sensor module 185 that is coupled with the physiological parameter sensor(s) and an external controller of an external local monitor device/system. Discrete electrical component(s) 112, such as, for example, tuning capacitors or the like, can be utilized to assist in achieving resonance in resonant circuits (e.g., L/C circuits) disposed in the transmission path between the sensor(s) 120 and the monitor device/system. For example, in a simplistic representation, the resonant frequency of an L/C circuit may be equivalent to: $f=1/(2\pi\sqrt{LC})$.

External Data and/or Power Communication Device/System

Monitoring systems disclosed herein can utilize inductively-coupled transmitters and/or receivers to provide and/or receive data, power, or both, in communication with an implanted valve having an integrated physiological parameter sensor. In certain embodiments, digital signals can be transmitted from the internal sensor(s) module using radio-frequency (RF) induction, which can provide for signal transfer that is relatively less susceptible to external interference than certain analog solutions may provide.

FIG. 7 is a block diagram illustrating an external local monitor system 700, which can be configured to receive sensor data inductively from an implanted device/module (not shown). In addition, the external monitor 350 can further be configured to receive and/or process certain metadata, such as device ID or the like, which can also be provided over the data coupling from the implanted module.

The external monitor 350 can comprise a controller 751 and/or transceiver 753, which can be communicatively coupled to the implanted sensor module using an antenna 780. In certain embodiments, the antenna 780 can comprise an external coil antenna that is matched and/or tuned to be inductively paired with a corresponding internal coil antennae associated with the internal implant sensor module.

Figure 8:
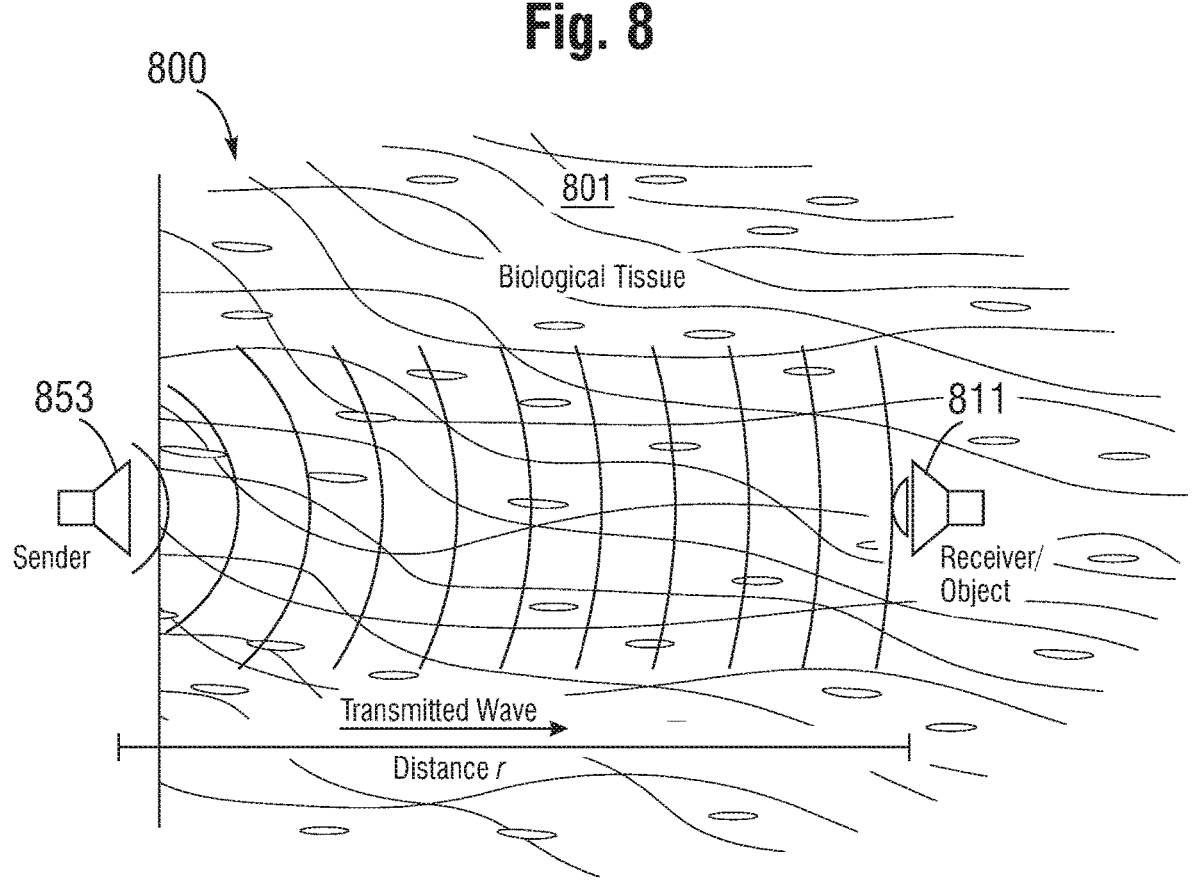
FIG. 8 illustrates a power and/or data communication system according to one or more embodiments.

FIG. 8 illustrates a power and/or data communication system 800 according to one or more embodiments. The system 800 can be configured to provide wireless ultrasound power charging and/or data communication between an external transmitter module 853 and a receiver module 811, which can be associated with an implant device in accordance with the present disclosure and disposed internal to a patient's body, such as in the patient's heart or associated vasculature. Therefore, a certain distance r of biological medium, including tissue, separates the receiver 811 from the transmitter 853. Because ultrasound communication utilizes mechanical sound waves, in some implementations, the ultrasound transmitter 853 can be configured to generate signals that propagate through the biological medium separating the transmitter 853 and the receiver 811 more efficiently than certain radio-frequency (RF) electromagnetic waves. Therefore, in certain embodiments, power charging using ultrasound transmission in accordance with the system of FIG. 8 can be more efficient than certain RF power charging implementations. In certain embodiments, the system 800 can be implemented to transmit ultrasound data signals to the receiver 811. Furthermore, in certain embodiments, the receiver 811 can be configured with ultrasound transmission functionality for transmitting data signals (e.g., sensor reading data) to the transmitter 853 or other external module. The ultrasound power and/or data communication system 800 can be particularly useful for embodiments utilizing piezoelectric sensor devices in accordance with embodiments disclosed herein.

Figure 9:
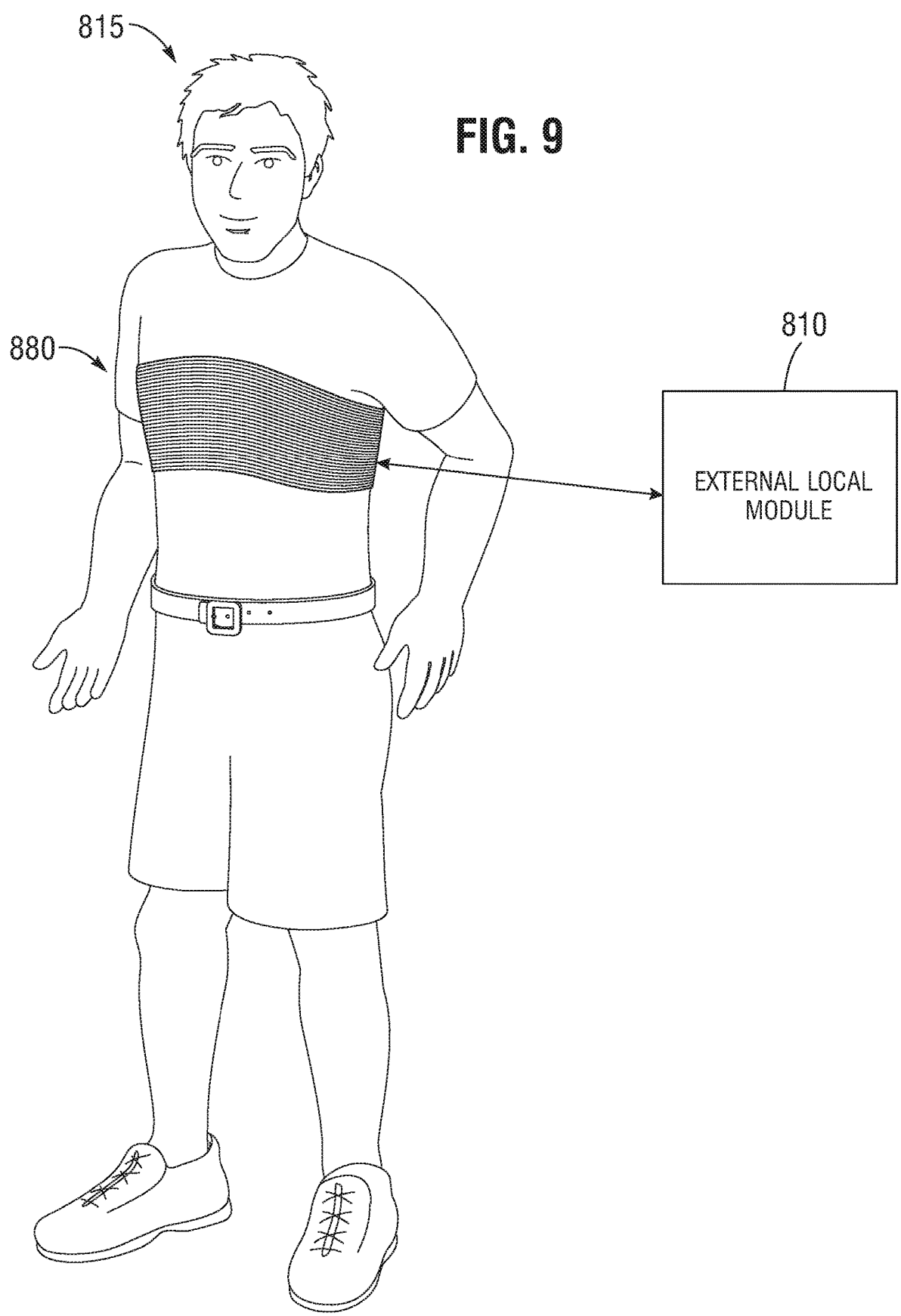
FIG. 9 illustrates an embodiment of an external coil device that can be used for coupling with an implanted sensor module according to one or more embodiments.

FIG. 9 illustrates an embodiment of an external coil device that can be used for coupling with an implanted sensor module according to one or more embodiments. The coil device 880 can be configured to be worn on or around the chest and/or torso area of a patient 815, such as underneath the user's armpit, as shown. Such a configuration can allow the external coil device 880 to be relatively close to co-planar with a corresponding internal coil device, which can provide desired efficiency with respect to power delivery and/or data communication.

With further reference to FIG. 7, the external local monitor 350 can comprise an integrated power source 759A, such as a battery or other power storage device or element. Alternatively, or additionally, the external local monitor 350 can be configured to receive power from an external source 759B, such as a plug-in power source. Use of battery power by the external local monitor 350 can advantageously allow for extended and/or near-continuous monitoring, as well as portability. For example, in certain embodiments, the external local monitor 350 can be carried by the patient, such as on a belt or other wearable article, allowing the patient to carry on daily activities with reduced inconvenience.

The controller 751 can be configured to initialize, calibrate, and/or program the internal implant sensor module. For example, the controller 751 can be configured to program sensor resolution, and/or adjust data acquisition intervals. During the monitoring period, the controller 751 can be programmed to monitor the implant sensor module (e.g., pressure conditions) at a fixed interval, or substantially continuously, and store the monitored data aboard the external monitor 350, such as in the data storage 754, and/or transfer the data to a secondary local monitor 770 for storage and/or use thereby. For example, the secondary local monitor 770 can me a computer to which sensor data can be downloaded once received by the external local monitor 350. The secondary local monitor 770 can be configured to implement more in-depth analysis of the sensor dada, possibly in conjunction with cardiopulmonary data acquired from other sources. In certain embodiments, the secondary local monitor 770 can provide input/output (I/O) capability for interaction with the patient or health care provider. For example, the secondary local monitor can comprise a tablet, laptop, desktop, smartphone, or wearable computing device, which can include a visual display as well as user input means, such as a keyboard, touchscreen, or the like. The external local monitor 350 can be coupled to the secondary local monitor 770 over a wired or wireless connection.

Sensor and Wireless Transmission Enabled Implant

Figure 10:
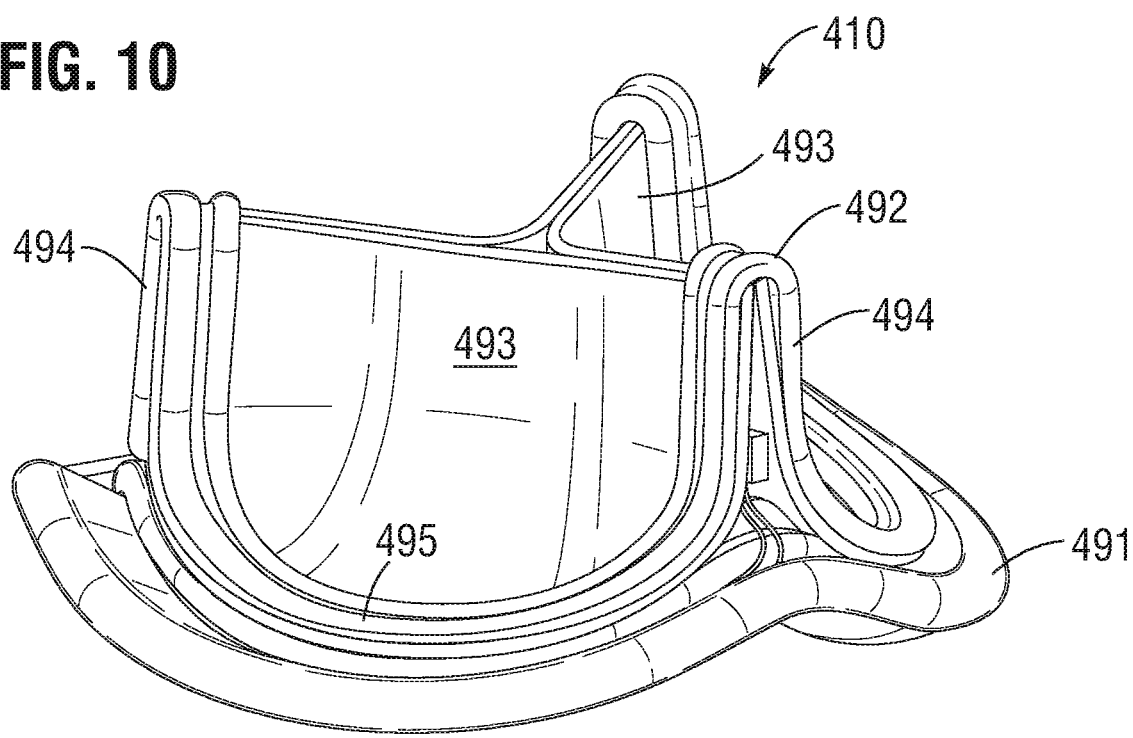
FIG. 10 provides a perspective view of the prosthetic heart valve comprising sensor and/or wireless transmission functionality for post-operative patient monitoring in accordance with one or more embodiments.

FIG. 10 is a perspective view of the prosthetic heart valve 410 comprising sensor and/or wireless transmission functionality for post-operative patient monitoring in accordance with one or more embodiments. The heart valve 410 can include a peripheral sealing ring structure 491 configured to provide support for nesting the heart valve 410 in a heart valve cavity and/or resting upon, or attached to, an annulus or other structure of the heart. The valve 410 further includes a frame member 492, such as a metal frame, which can provide support for a plurality of flexible leaflets 493 and defines three upstanding commissure posts 494, wherein the leaflets 493 are supported between the commissure posts 494. The sealing ring 491 can attach around the periphery of the frame member 494 at the inflow end of the valve, with the commissure posts 494 projecting in the outflow direction.

The leaflets 493 can be formed from separate flaps of tissue, such as xenograft tissue (e.g., bovine pericardium), or all three leaflets can be derived from a single xenograft valve (e.g., a porcine valve). The leaflets 493 can be secured and supported both by the commissure posts 494, as well as along arcuate cusps 495 of the frame member between the commissure posts.

Figure 11:
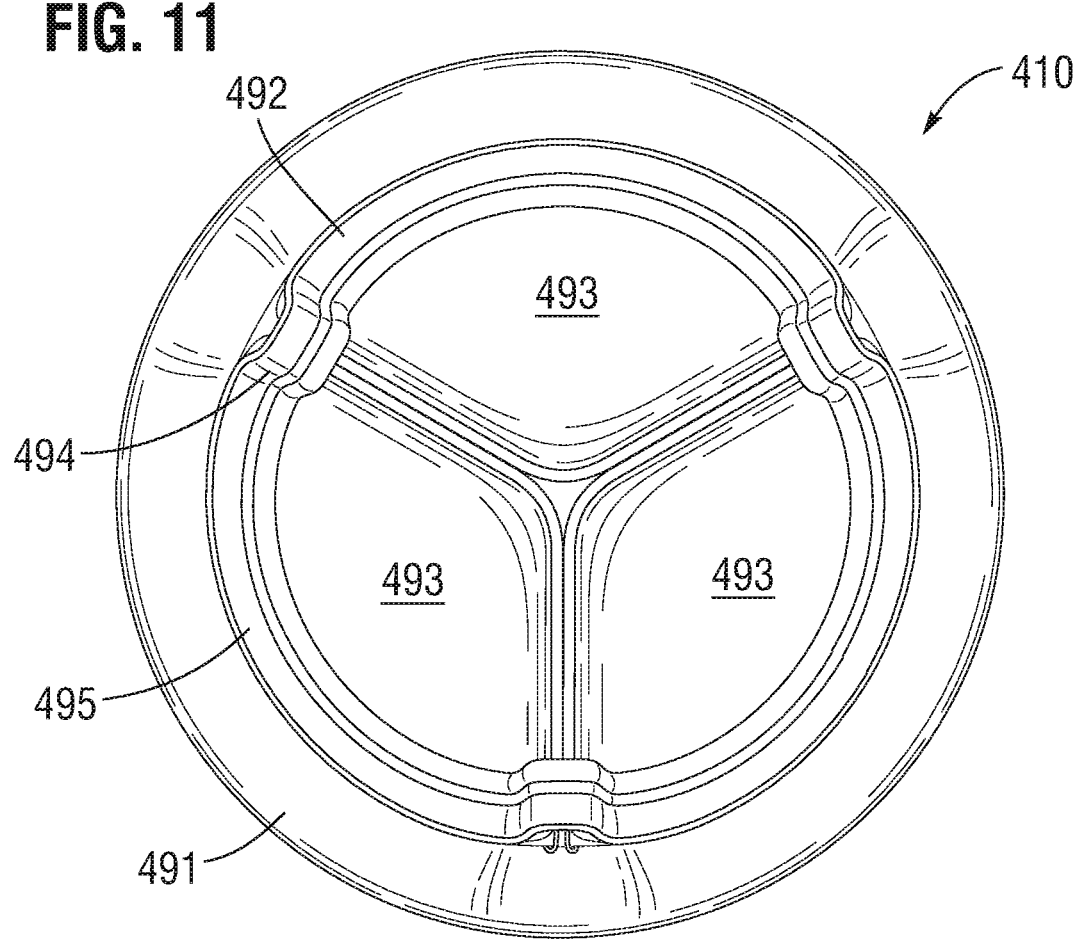
FIG. 11 provides a top view of the prosthetic heart valve shown in FIG. 10.

FIG. 11 is a top view of the prosthetic heart valve 410 shown in FIG. 10. The heart valve 410 is illustrated in a closed position in which fluid flow the valve is inhibited; when in an at least partially-open state, fluid (e.g., blood) can flow in one direction through an inner channel of the valve that is formed when the leaflets 493 separate.

The frame member 492 can be generally rigid and/or expansion-resistant in order to substantially maintain a particular shape (e.g., generally round from a top perspective, as shown in FIG. 11) and diameter of the valve orifice and also to maintain the valve leaflets 493 in proper alignment in order for the valve to properly close and open. Although a substantially round embodiment is depicted in FIG. 11, other shapes are also within the scope of the invention, depending on the particular application (e.g., the particular native valve to be replaced, etc.). In certain embodiments, the frame member 492 has some degree of flexibility.

Figure 12:
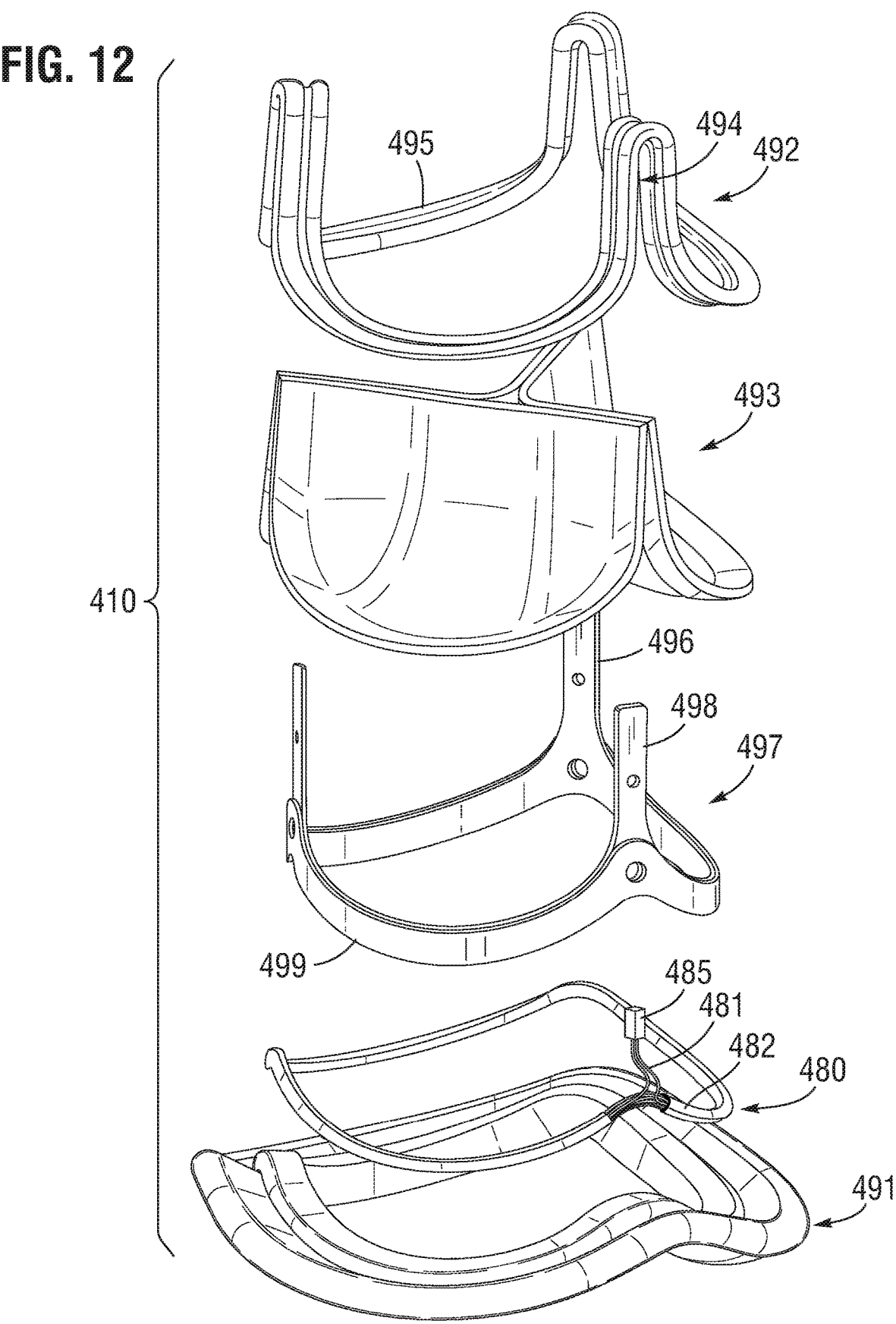
FIG. 12 provides an exploded perspective view of the prosthetic heart valve of FIG. 10 according to one or more embodiments.

FIG. 12 is an exploded perspective view of the prosthetic heart valve 410 of FIG. 10 according to one or more embodiments. The valve assembly 410 includes a frame member 492, which can comprise a metal/wireform frame structure. In certain embodiments, the frame member 492 can be at least partially covered with fabric or other material. The frame 492 can define narrow arcuate upwardly-projecting commissure regions 494 in-between downwardly-projecting arcuate cusps 495.

The frame 492 can be at least partially secured or attached to a leaflet assembly 493. The leaflets 493 can be made at least in part of biologically-derived tissues that provide flexibility and structure for occluding fluid flow through the valve 410 as described above. The leaflets 493 extend inward from the surrounding frame 492 into a flow orifice defined thereby. In certain embodiments, there are three bio-prosthetic leaflets that curve toward the outflow direction and "coapt" in the middle of the valve orifice to facilitate one-way flow through the valve.

The valve assembly 410 further includes a stent member 497 designed to fit above the sealing ring 491. In certain embodiments, the stent member 497 includes a plastic band 496 (e.g., polyester, polyethylene terephthalate (PET), or biaxially-oriented PTE, for example, Mylar PET, DuPont Teijin Films), wherein the leaflets 493 can be sewn or otherwise attached to the plastic band. The stent member 497 can further include a rigid stiffening band 499, which can be comprised of, for example, metal or other rigid material. The plastic band 496 includes a commissure support portion 498, which can fit at least partially within the upwardly-projecting commissure regions 494 of the frame member 492. In certain embodiments, one or more of the commissure support portions 498 of the plastic band 496 can have a strain gauge or other sensor device(s) associated therewith. For example, a strain gauge can be attached to the support portion 498 or etched or integrated therein. The strain gauge or other sensor(s) can be used to provide data that can be useful for patient/device diagnosis as described herein.

Sensor data collected by one or more sensor(s) (e.g., strain gauge(s)) associated with the valve assembly 410 can be transmitted to an external receiver (not shown) using a transmitter assembly 480. The transmitter assembly 480 can include a conductive coil 481 electrically coupled to an electronic sensor or circuit 485, wherein the coil can be configured to provide power to the sensor/circuit 485, transmit electromagnetic signals to an external receiver, and/or receive power/data therefrom. For example, the coil 481 can operate as an antenna for receiving wireless power and/or for transmitting electromagnetic signals. In certain embodiments, the transmitter assembly 480 can be embedded in, or integrated with, the valve assembly 410. For example, the transmitter assembly 480 can be nested within a recess, channel, or cavity of the sealing ring 491 or other component or structure of the valve assembly 410. By embedding the coil 481 in an outer portion of the heart valve 410, the assembly 480 can allow for a hoop-shaped antenna having a relatively large diameter, which can provide certain electromagnetic signal transfer benefits.

With further reference to FIG. 12, in certain embodiments, the sealing ring 491 of the heart valve assembly 410 can be configured to at least partially stabilize the annulus and to support the functional changes that occur during the cardiac cycle, such as by maintaining coaptation and valve integrity to prevent reverse flow while permitting good hemodynamics during forward flow. The sealing ring 491 can comprise an inner at least partially rigid substrate (e.g., metal such as stainless or titanium, or a flexible material such as silicone rubber or PET (e.g., DACRON PET) cordage), and can be at least partially covered with a biocompatible fabric or cloth to allow the ring to be sutured to the heart tissue. The sealing ring 491 can be stiff or flexible, can be split or continuous, and can have a variety of shapes, including circular, D-shaped, kidney-shaped, or C-shaped. In certain embodiments, when implanted, suture fasteners (not shown) can be distributed around the sealing ring 491 that bind the sealing ring to the attachment tissue of the patient. The heart valve 410 can include various visualization markers (not shown; e.g., radiopaque markers), which can aid in proper placement of the heart valve.

Figure 13:
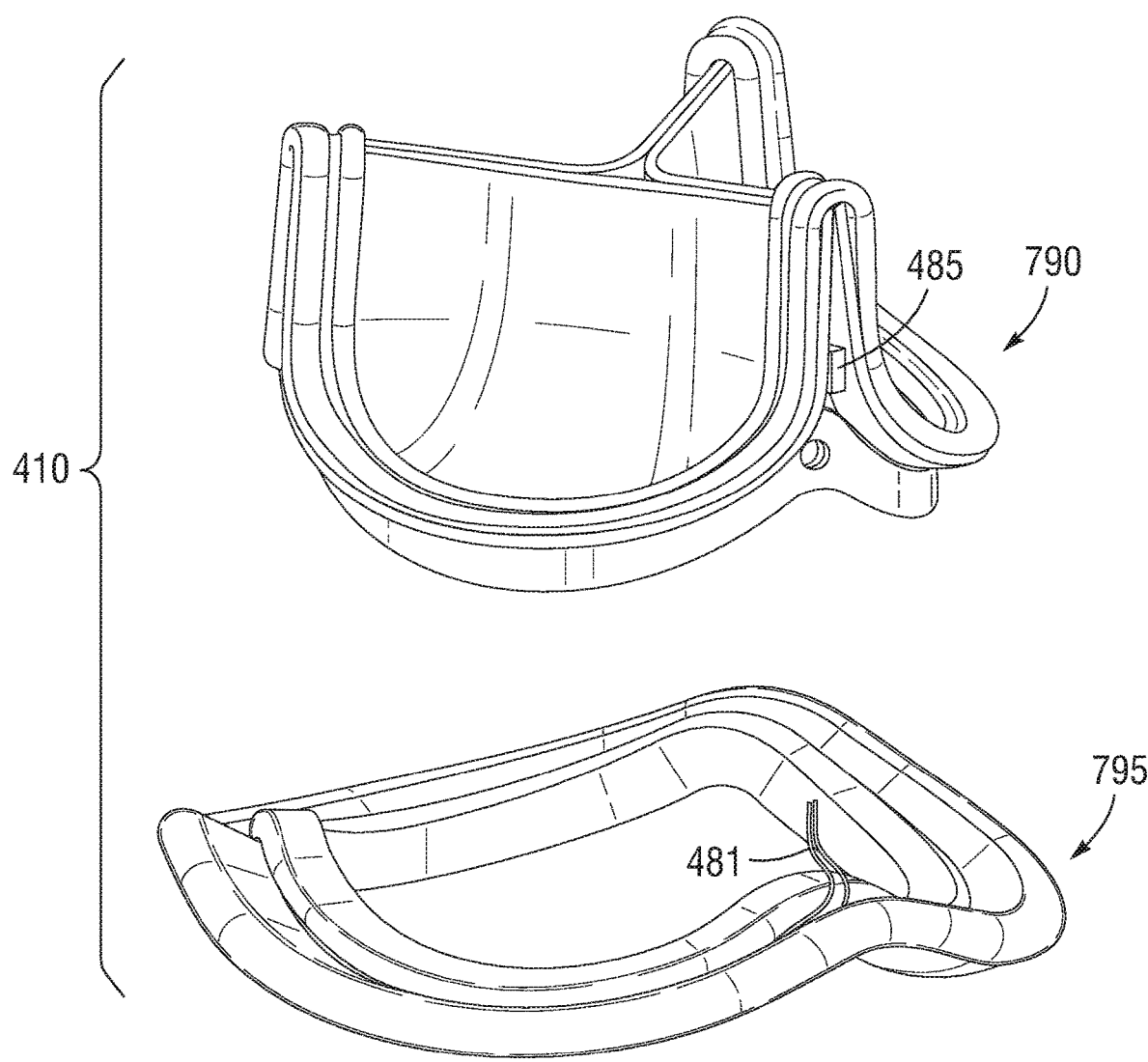
FIG. 13 provides another partially-exploded view of the prosthetic heart valve of FIG. 10 according to one or more embodiments.

Assembling the various illustrated components shown in FIG. 12 can result in an assembled heart valve similar to that shown in FIGS. 10 and 11 and described above. FIG. 13 provides another partially-exploded view of the prosthetic heart valve 410 of FIG. 10 according to one or more embodiments. The diagram of FIG. 13 shows a combined frame, leaflet and stent assembly 790, wherein the assembly 790 includes one or more sensors and/or electrical circuitry, such as the illustrated electronic sensor module 485. The diagram of FIG. 13 further shows a combined sealing ring and transmitter assembly 795 including, for example, an embedded/nested transmitter coil that can be coupled to one or more sensors or electronics via wires 481 of the coil.

Figure 14A:
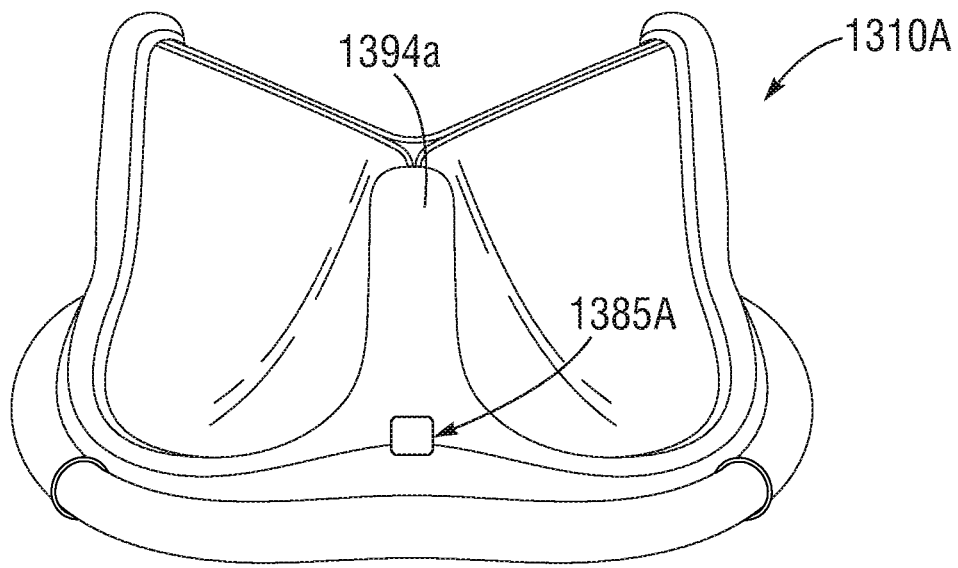
FIGS. 14A and 14B illustrate implant devices having electronic sensor devices associated therewith according to one or more embodiments.
Figure 14B:
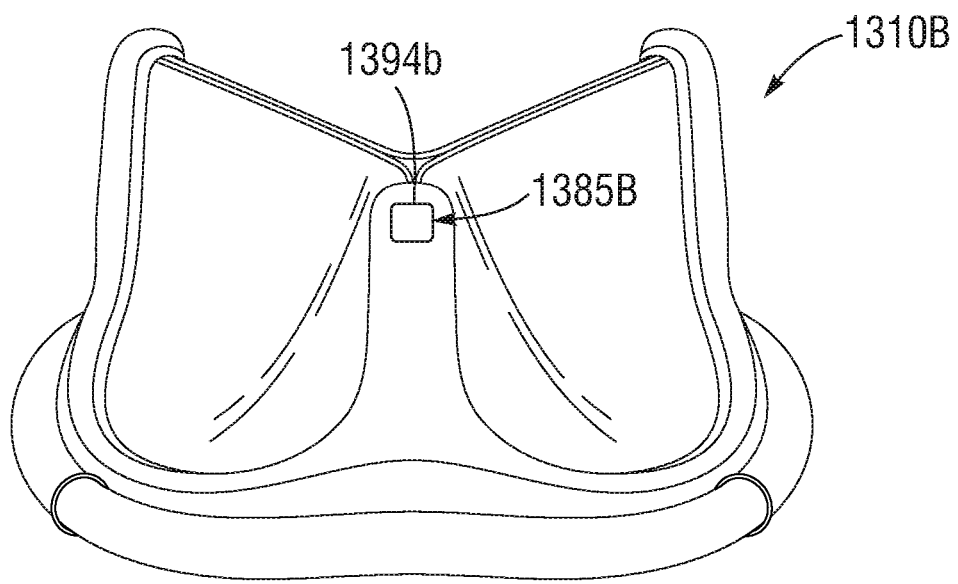

FIGS. 14A and 14B illustrate implant devices having electronic sensor devices associated therewith according to one or more embodiments. Implant sensor devices (e.g., microchips, MEMS sensors), as disclosed herein can be integrated with, or associated with, any desirable structural feature or component of a prosthetic implant device, such as anywhere along a stent portion of a valve implant. FIG. 14A shows an implant device 1310A having a sensor device 1385A (e.g., integrated MEMS sensor) mounted on an outflow side of the valve 1310A, towards the bottom region of a stent portion of the valve 1310A. As an alternative, FIG. 14B shows an implant device 1310B having a sensor device 1385B mounted on a commissure post portion of the implant device 1310B. In embodiments in which the sensor device is mounted on the commissure post, the sensor device can incorporate a MEMS accelerometer, which can provide data indicating commissure movement. Other types of sensors that may be utilized can include piezoelectric sensors or piezo-resonant sensors.

Data/Power Transmitter

As described above, sensor data and/or power for operating an implanted sensor device/module can be transferred between an implanted sensor device and an external monitor using wireless transmission according any suitable or desirable method or mechanism. FIG. 15 illustrates a stent member (e.g., polymer stent) 1497 having a sensor device 1485 associated therewith, wherein the sensor device 1485 is coupled electrically to a coil antenna 1480 via one or more connections 1481. In certain embodiments, the sensor 1485 and/or antenna 1480 are at least partially integrated into the stent member 1497. For example, an inner portion 1499 of the stent member 1497 can be made of a polymer material, wherein the integrated sensor(s), circuit(s), and/or coil(s) can be further at least partially integrated with, or embedded, into the stent member 1497, either collectively or individually.

With implantable sensor devices, such as those integrated with prosthetic heart valves or the like, a certain amount of power for operating such sensors may be required. However, due to cost, comfort, convenience, and other factors, it may be desirable to power the implanted sensor, and transmit sensor signals from the implanted sensor, wirelessly in a non-invasive manner. Disclosed herein are various systems, devices, and methods for providing power from a power source to an implanted sensor device wirelessly. In certain embodiments, the principles of near-field technology can be implemented by utilizing a microwire coil, which can be connected in series with the implanted sensor and incorporated with, for example, the frame or other structural component of the prosthetic heart valve. An external antenna can be used by a patient, or even worn by or placed on the patient, to introduce a magnetic field for coupling with the internal coil 1480 to passively power the sensor 1485 and/or corresponding circuitry to allow for wireless data acquisition. Therefore, incorporating the coil 1480 in series with the sensor 1485 can allow for a relatively simple method of powering the device 1485 and non-invasive measurements.

FIG. 16A shows a heart valve assembly 810 according to one or more embodiments disclosed herein. The heart valve assembly 810 can include sensor and/or wireless transmission functionality for post-operative monitoring as described herein. For example, the heart valve assembly 810 can include one or more sensors (not visible in the view of FIG. 16A) coupled to a transmitter assembly (not visible in the view of FIG. 16A), which can be embedded in the structure of the heart valve, via one or more electrical contacts/connections 881.

A cross-sectional view of the heart valve assembly 810 of FIG. 16A is shown in FIG. 16B. The view of FIG. 16B shows a conductive coil 880 of a transmitter assembly embedded/nested in a channel of a sealing ring structure 891. The coil 880 can wrap around at least part of the circumference, or other dimension, of a portion of the valve assembly 810, such as the seal ring 891. The coil can be used as a power coil antenna, and can be configured to receive electrical energy from an external power source without discrete electrical conductor(s) (e.g., wires) coupling the coil 880 to the power source. Such wireless power transfer can be effected using any practical or desirable power transmission technology, and can generally implement power transfer through the use of time-varying electric, magnetic, or electromagnetic fields. In certain embodiments, a wireless transmitter connected to an external power source (not shown) conveys electro/magnetic field energy across a space between the power source and the antenna coil 880 (e.g., through certain biological tissue of the patient), wherein the coil assembly 880 (e.g., in combination with certain circuitry/electronics) is configured to converted the field energy back to an electrical current that can be utilized by one or more sensors and/or circuits of the valve assembly 810.

In certain embodiments, received power can be stored in a power storage device of the valve assembly 810, such as a capacitor, battery, etc. The received power can be used to power wireless data transmissions from the transmission subassembly (which includes the coil 880) to an external receiver, which can be integrated with the power source device/system.

The circumferential area/region of the sealing ring 891, or other component of the valve assembly 810, can advantageously provide a relatively long path for the coil 880 with a relatively large antenna aperture (i.e., diameter), thereby providing a relatively greater transmission range of the antenna; antenna read/transmit range can have a substantially linear relationship with antenna aperture in certain embodiments. Greater antenna range may be beneficial in embodiments disclosed herein in view of the space that will necessarily be present between the valve and the exterior of the patient's body, as well as the general convenience provided through relatively less strict distance/range requirements. In certain embodiments, the coil 880 can have a diameter/aperture that is greater than 10 mm in diameter. For example, the coil 880 can have a diameter of between 15-35 mm. In certain embodiments, the coil 880 has a diameter between approximately 19-33 mm. In certain embodiments, the coil has a diameter of approximately 40 mm, or greater. In certain embodiments, the coil 880 has a diameter between 35-40 mm. In certain embodiments, the coil 880 has a diameter of approximately 14 mm, or less. Due to the at least partial rigidity of the sealing ring 891, the coil antenna 880 can advantageously be maintained in a shape to maintain a relatively wide aperture.

In certain embodiments, the transmission assembly can be configured to communicate power and/or data according to inductive coupling, resonant inductive coupling (e.g., RFID), capacitive coupling, or the like. For example, the transmission assembly can be configured to transmit information relating to sensed biological or device parameter(s), as well as data identifying one or more of the valve (e.g., make, model, identification number, serial number) and/or the patient (e.g., name, identification number, patient identifier).

FIG. 16C shows an enlarged view of the cross-section of the coil 880 shown in FIG. 16B. The coil 880 can comprise a plurality of turns of wire or other conductor, as shown, or can have a single turn. In certain embodiments, the coil 880 can include a core form (not shown; e.g., magnetic core or air core) around which the coil can be at least partially wound.

Figure 17:
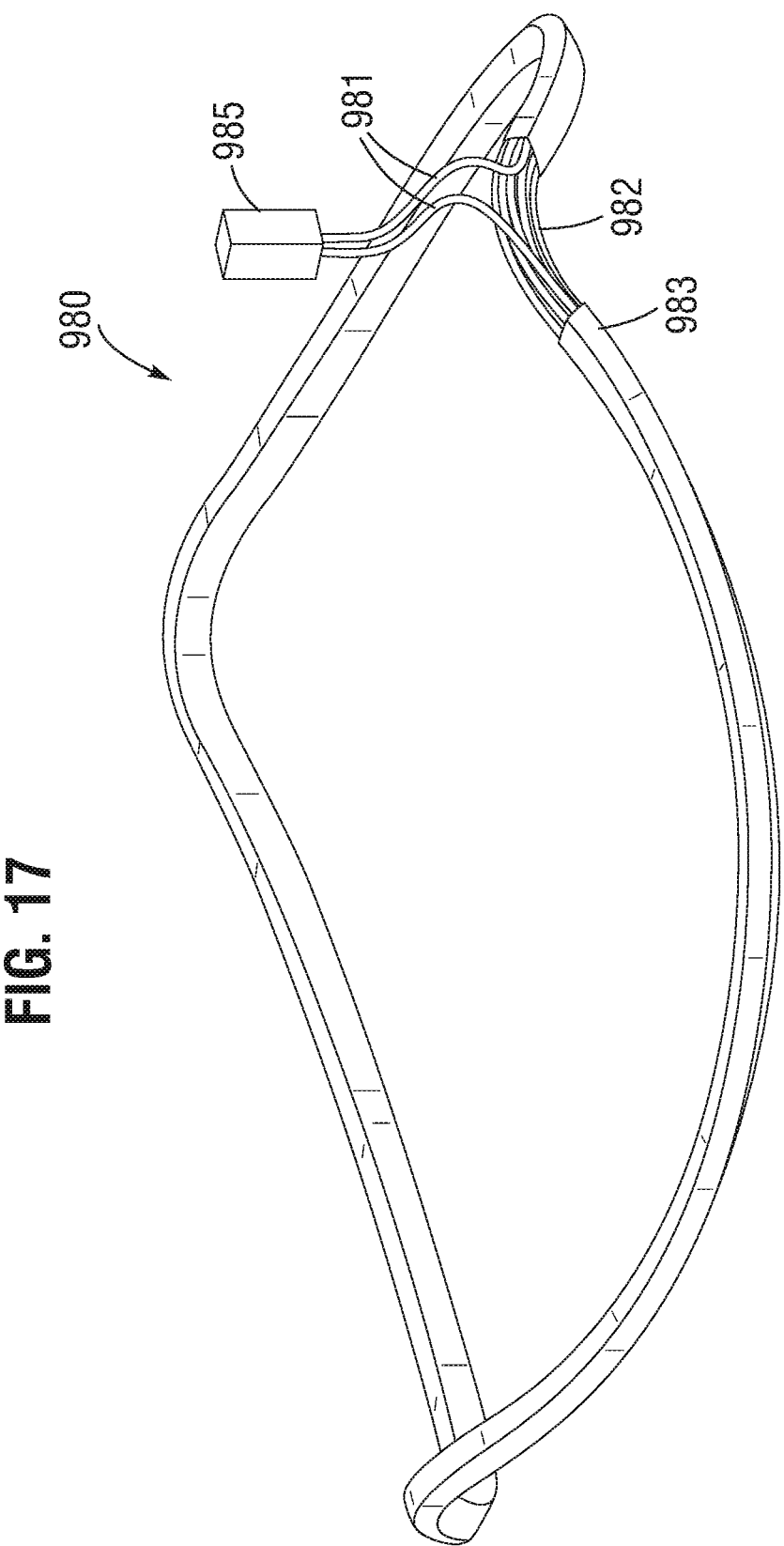
FIG. 17 shows a transmitter assembly according to one or more embodiments.

FIG. 17 shows a transmitter assembly 980 according to one or more embodiments. The transmitter assembly 980 can have a shape that generally conforms to the shape of a portion of a heart valve assembly in which the transmitter assembly 980 can be configured to be embedded. As described in detail above, the transmitter assembly 980 can comprise a coil 982 that can comprise one or more conductive wires wrapped around a circumferential path of the assembly 980. In certain embodiments, the coil 982 is at least partially covered with a sheath or covering 983, which can provide electrical, thermal, and/or physical isolation between the coil 982 and external components or structures of the valve with which the assembly 980 is associated.

The coil 982 can be electrically coupled via one or more leads 981 to one or more electrical components, such as a sensor or circuit module 985. The transmitter assembly 980 can be further coupled to one or more additional sensors or components (not shown) of the associate valve assembly. As described in detail above, the transmitter 980 can be assembled to receive power wirelessly and/or transmit sensor and/or other data wirelessly using the coil 982 as an antenna.

In certain embodiments, the circuitry 985 can be configured to perform some amount of signal processing for signal transmission, such as signal filtering, amplification, mixing, and/or the like. In certain embodiments, the circuitry 985 includes one or more processors, data storage devices, data communication busses, and/or the like.

Antenna coils for data and/or power transfer between sensor-integrated implant devices and external monitor devices/systems can have any desirable or suitable configuration. Near-field communication can involve the use of two parallel-aligned coil loops that are magnetically coupled, one being the transmitter and the other being an antenna with current running through to introduce a magnetic field. To be able to surpass attenuation from the surrounding tissue and fluid within the patient anatomy when the sensor device is implanted in a patient, it may be desirable for the current through the antenna to be run at relatively lower frequencies, which may generally require the use of relatively larger diameter coils. In certain embodiments, the antenna coil may be wrapped at least partially around a core form or volume (e.g., magnetic iron/ferrite core or air core) to help improve coupling. For use in implant devices, it may be desirable or necessary for a ferrite-wrapped coil to be hermetically sealed in a biocompatible casing to prevent exposure to the surrounding tissue(s).

Optimizing the near-field communication between internal and external coils can allow for passively powering the integrated circuit sensor system in the implant prosthesis (e.g., heart valve), which can reduce or negate the need for internal battery power incorporated in the implant. FIGS. 18A-18F show embodiments of implant devices having antenna coils for data and/or power transfer associated therewith. FIGS. 19A-19D provide cross-sectional views of antenna structures of the implant devices of FIGS. 18A-18D, respectively. The embodiments of FIGS. 18A-18F represent certain example configurations of data/power coils, and it should be understood that other variations not specifically illustrated can be implemented within the scope of the present disclosure.

Figure 18A:
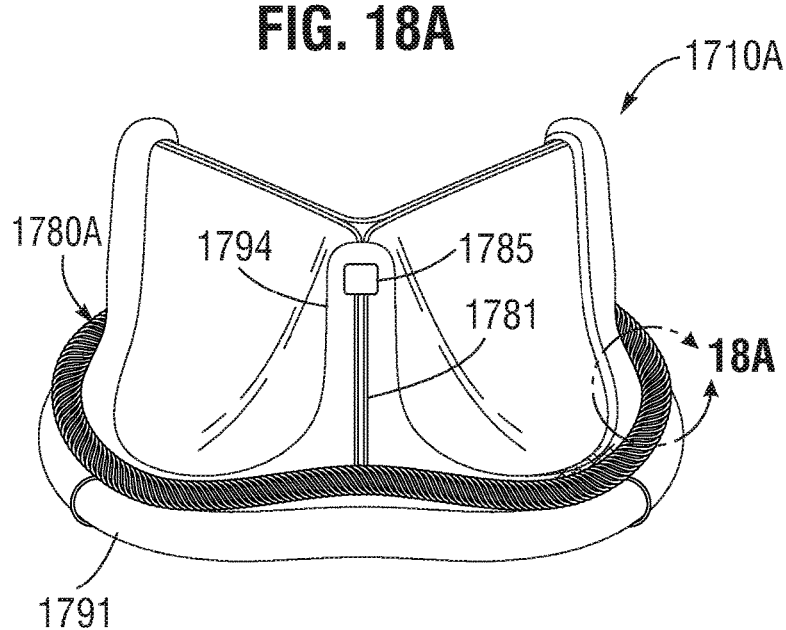
FIGS. 18A-18F show various embodiments of implant devices having antenna coils for data and/or power transfer associated therewith.
Figure 19A:
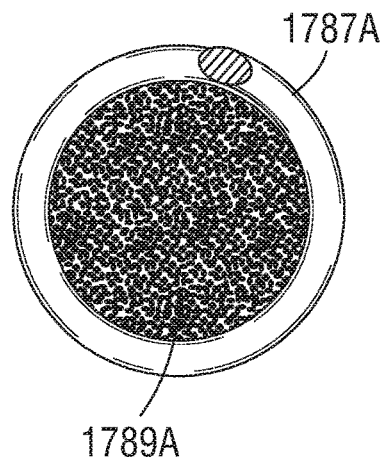
FIGS. 19A-19D provide cross-sectional views of antenna structures of the implant devices of FIGS. 18A-18D, respectively.

FIG. 18A shows an embodiment of an implant device 1710A (e.g., heart valve implant) having a sensor module 1785 coupled to a coil structure 1780A. The coil structure 1780A comprises a wire winding wrapped around a core form or volume (not shown; e.g., magnetic core or air core), wherein the coil structure 1780A is integrated or associated with a circumferential ring or component 1791 of the implant device 1710A to enable near-field communication between the coil 1780A and an external monitor device (not shown). FIG. 19A shows a cross-sectional view of the coil structure 1780A, showing an outer wire 1787A circumferentially wrapped around an interior core 1789A. The interior core features (1789A-1789E) of FIGS. 17A-17E and FIGS. 18A-18D can each comprise a non-magnetic core, such as an air core, or a magnetic core (e.g., ferrite core, such as an iron ferrite core), or any other type of core. With respect to air core embodiments, the windings can be wrapped at least partially around a non-magnetic form, such as a hollow tube or other shape of some material. In certain embodiments, it may be desirable to incorporate a core that is non-magnetic to prevent magnetic interference with the function of the heart or other organs and/or interference with sensor/transmission circuitry or signals. In certain embodiments, the core 1789A is hermetically sealed.

Figure 18B:
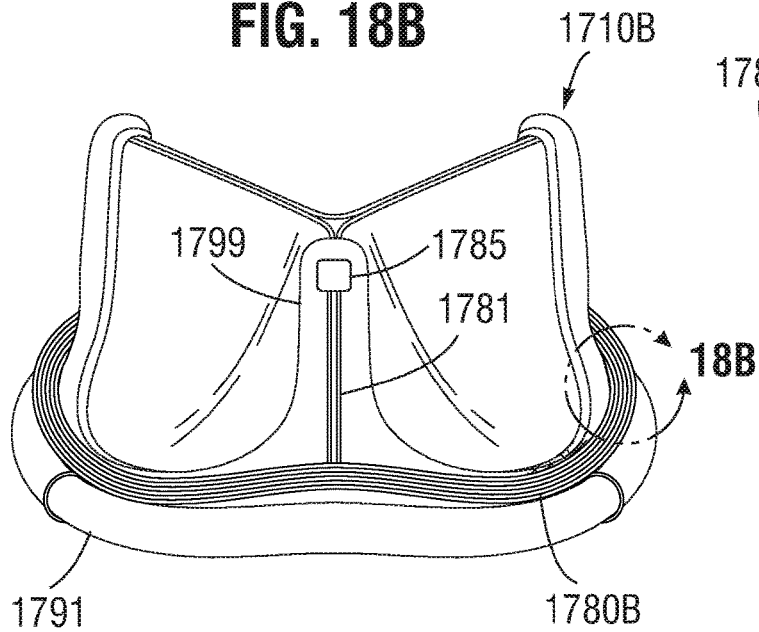
Figure 19B:
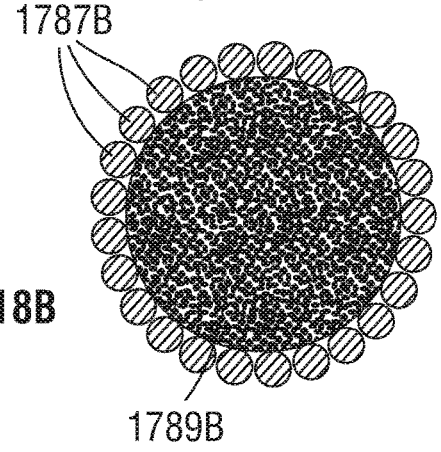

FIG. 18B shows an embodiment of an implant device 1710B (e.g., heart valve implant) having a sensor module 1785 coupled to a coil structure 1780B. The coil structure 1780B comprises a wire winding running along a circumferential path about one or more structural components of the implant device 1710B. the lengths of wire of the coil structure 1780B can surround a core form or volume (not shown; e.g., magnetic core or air core), wherein the coil structure 1780B is integrated or associated with a circumferential ring or component 1791 of the implant device 1710B to enable near-field communication between the coil 1780B and an external monitor device (not shown). FIG. 19B shows a cross-sectional view of the coil structure 1780B, showing outer wires 1787B longitudinally running along a length of an interior core 1789B (e.g., magnetic core ferrite core or air core).

Figure 18C:
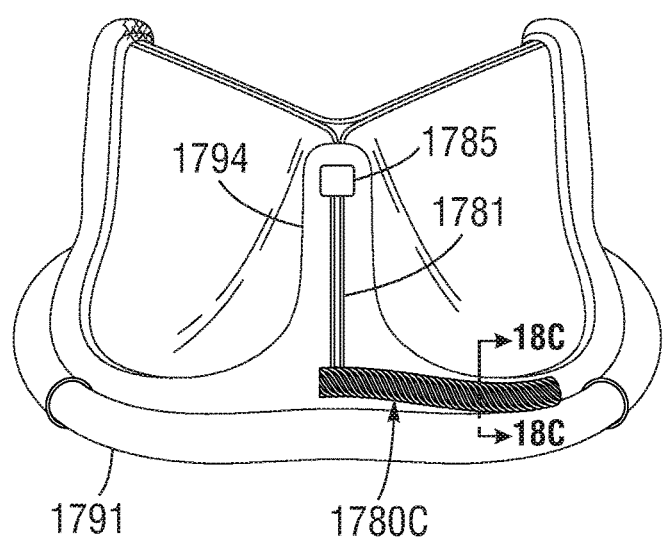
Figure 19C:
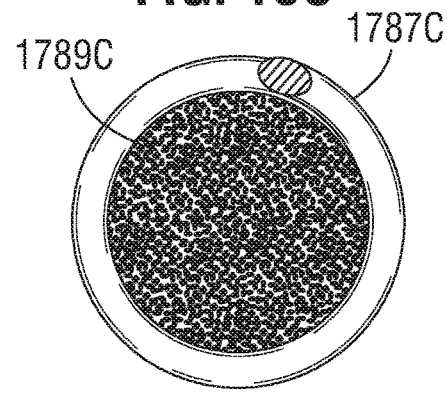

FIG. 18C shows an embodiment of an implant device 1710C (e.g., heart valve implant) having a sensor module 1785 coupled to a coil structure 1780C. The coil structure 1780C comprises a wire winding wrapped around a core form or volume (not shown; e.g., magnetic core or air core), wherein the coil structure 1780C is integrated or associated with a circumferential ring or component 1791 of the implant device 1710C to enable near-field communication between the coil 1780C and an external monitor device (not shown). The coil structure 1780C extends only along a partial portion of the circumference of the base of the implant device 1710C. For example, the partial portion over which the coil structure 1780C extends can correspond to an outward-facing portion of the implant device 1710C when implanted in order to reduce the distance and amount of tissue separating the soil structure 1780C from the exterior of the patient's chest to improve coupling between the coil structure 1780C and an external monitor module. FIG. 19C shows a cross-sectional view of the coil structure 1780C, showing an outer wire 1787C circumferentially wrapped around an interior core form or volume (e.g., magnetic core or air core) 1789C.

Figure 18D:
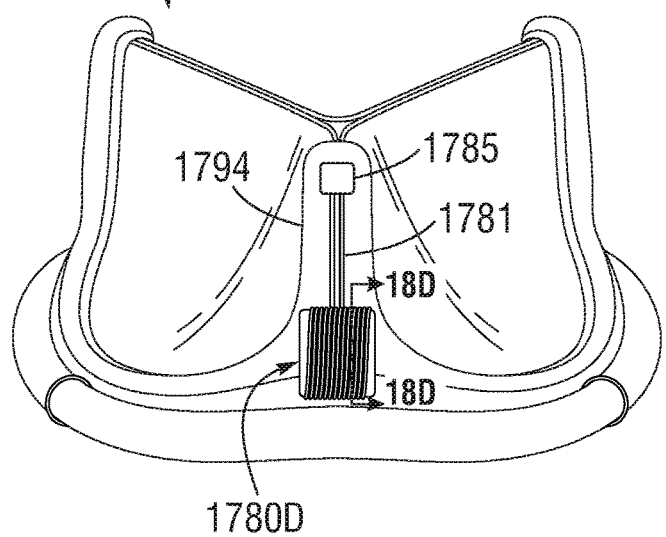
Figure 19D:
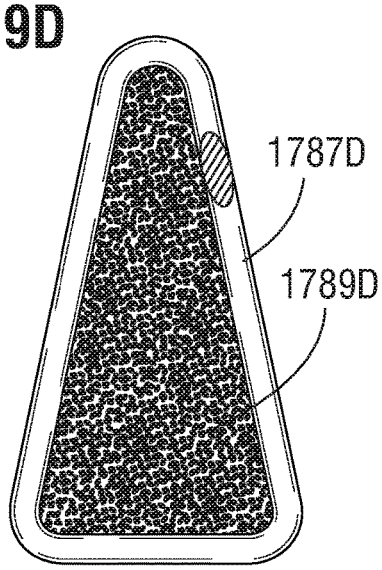

FIG. 18D shows an embodiment of an implant device 1710D (e.g., heart valve implant) having a sensor module 1785 coupled to a coil structure 1780D. The coil structure 1780D comprises a wire winding wrapped around a core form or volume (not shown; e.g., magnetic core or air core), wherein the coil structure 1780D is integrated or associated with a frame or stent structure or component of the implant device 1710D to enable near-field communication between the coil 1780D and an external monitor device (not shown). The coil structure 1780D can comprise a relatively short length of core form or volume (e.g., magnetic core or air core) having wire windings wrapped around an outer surface of the core form or volume 1780D. FIG. 19D shows a cross-sectional view of the coil structure 1780D, showing an outer wire 1787D circumferentially wrapped around an interior core (e.g., magnetic core or air core) 1789D. The core 1789D can have any transverse cross-sectional shape, although a triangle-type shape is shown for illustration purposes.

Figure 18E:
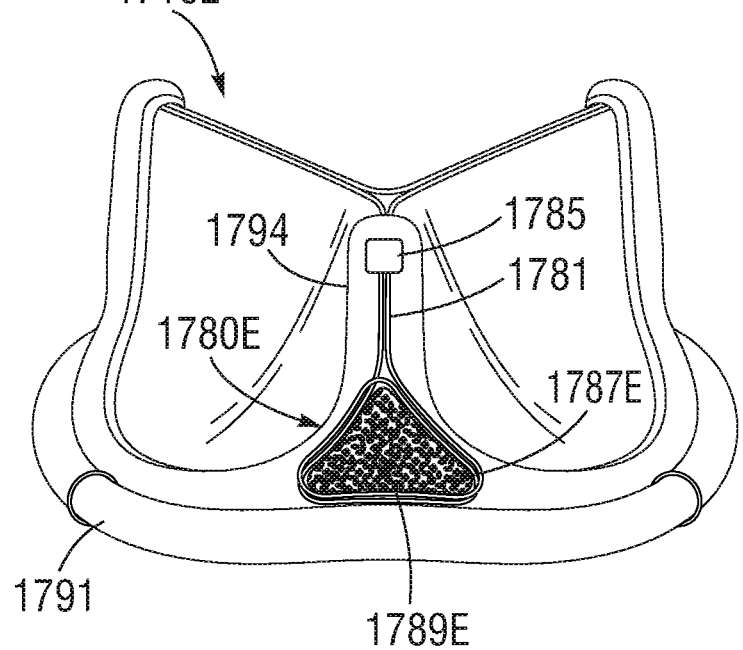

FIG. 18E shows an embodiment of an implant device 1710E (e.g., heart valve implant) having a sensor module 1785 coupled to a coil structure 1780E. The coil structure 1780E comprises a wire winding 1787E wrapped around a core form or volume 1789E, wherein the coil structure 1780E has a radial axis with respect to base ring/structure 1791 of the implant device 1710E. Such a configuration may be desirable because inductive coupling can be achievable with a co-axial coil of an external monitor device (not shown), which can improve coupling between the implant device and the external device. The coil structure 1780 can have any desirable cross-sectional shape, and can advantageously have a shape that conforms at least in part to the shape of one or more physical structures/components of the implant device 1710E, such as the generally-triangular shape shown in FIG. 18E. Compared to certain of the coil structures shown in FIGS. 18A-18D, the coil 1780 can advantageously have a relatively greater diameter, which can improve coupling in certain embodiments.

Figure 18F:
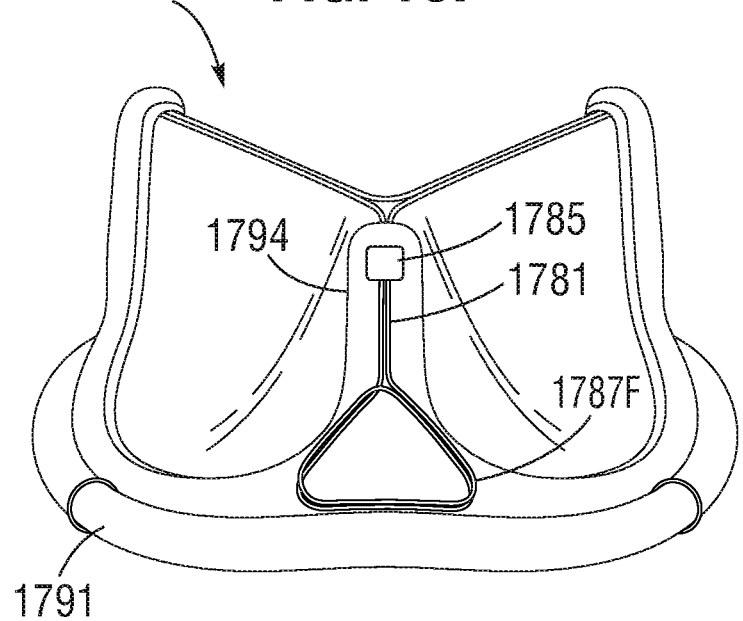

FIG. 18F shows an embodiment of an implant device 1710F (e.g., heart valve implant) having a sensor module 1785 coupled to a coil structure 1780F. The coil structure 1780F comprises a wire winding 1787F similar to that shown in FIG. 18E, except that the embodiment of FIG. 18F does not include a core form (e.g., magnetic or air-filled form disposed within the windings 1787F, such that the wire winding 1787F is simply wound around a volume or air or other substance.

Diagnostic Instrumentation; Commissure Deflection

Certain embodiments disclosed herein provide novel instrumentation for prosthetic devices, such as heart valves, for gathering and/or processing physiological/device parameter data for patient diagnostics. For example, the instrumentation and/or processes disclosed below can be used in connection with a heart valve as shown in certain of the preceding figures and described above. The devices, systems and methods disclosed herein can be used for identifying symptoms or conditions indicating potential heart or implant failure issues in patients that have received a prosthetic heart valve implant, or other implant device. Some implementations provide for the use of a strain gage to measure commissure deflection and valve function in a heart valve device.

A strain gage for measuring commissure deflection can be applied to a wireform or stent component of a prosthetic valve, or can be attached to a plastic insert within a commissure of the valve, or attached to or integrated with any other component or location of an implant device that is suitable for measuring the strain of a component. Although strain gauges are discussed in detail herein, other sensors can be used to measure commissure deflection, such as accelerometers, gyroscopes, optical sensors, or the like. Such sensors can likewise be disposed on commissure posts to measure commissure deflection. The data provided by, or derived from, commissure deflection sensor(s) in an implanted heart valve can be used to alert a patient or health care provider of a change in the patient's heart rate or blood pressure, and can provide an early indication of a change in heart function. As described above, patients who undergo a prosthetic heart valve implant operation can sometimes have post-implant heart failure related morbidity/mortality. Heart valve commissure deflection sensor devices and wireless data transmission functionality as disclose herein can be able to provide early information regarding heart function and thus allow for earlier intervention for patients. Although certain embodiments are disclosed herein in the context of commissure deflection, it should be understood that the principles disclosed can be applicable with respect to strain and/or deflection of one or more other components, such as cusp/leaflet deflection, or the like. Therefore, the embodiments and diagnostic techniques/mechanisms below can be based at least in part on cusp/leaflet deflection, or other measured strain/deflection within an implant device.

FIG. 20 is a side view of a heart valve 1010 according to one or more embodiments. The valve 1010 can include a plurality of leaflets 1093 attached to one or more of a frame member 1092, stent member 1097, and/or sealing ring 1091. The frame member 1092 can include commissure post forms 1094, as well as arcuate cusp forms 495 connecting between the commissure posts.

In certain embodiments, the valve 1010 includes one or more sensors, such as a strain gauge 1088, which can be attached to, or embedded within, a commissure post of the valve 1010. For example, the strain gauge 1088 can be attached to, or etched in, a commissure support portion 1098 of the stent member 1097, which can comprise a plastic (e.g., PET) band. The strain gauge 1088 can comprise an electrical conductor that has electrical conductance properties that depend at least in part on the geometry of the conductor; when the commissure post 1098 deflects in a way as to present tension on the strain gauge 1088 (e.g., inward deflection when the strain gauge is associated with an outer surface of the commissure portion 1098), the electrical conductor of the strain gauge 1088 can become stretched, thereby becoming relatively narrower and/or longer, which can increase the electrical resistance of the conductor end-to-end. Alternatively, when the commissure post 1098 deflects in a way as to result in compression of the strain gauge 1088 (e.g., outward deflection where the strain gauge is associated with an outer surface of the commissure portion 1098), the electrical conductor of the strain gauge 1088 can experience increased thickness, which can decrease the electrical resistance of the conductor end-to-end. The electrical resistance of the strain gauge can therefore be measured, and the amount of deflection or induced stress on the commissure post can be inferred based on such measurement. In certain embodiments, the strain gauge can comprise a conductive channel configured in a zig-zag-type pattern of parallel lines such that a stress in the direction of the orientation of the parallel lines results in a measurable change in resistance over the effective length of the conductive lines.

Although only a single strain gauge is shown or visible in FIG. 20, it should be understood that the valve 1010 can have strain gauge features on each of a plurality of commissure posts. Furthermore, although a strain gauge is illustrated in FIG. 20 and described herein, the principles of measuring commissure post deflection can be utilized with any desirable or practical deflection measurement mechanism or technique. In an embodiment in which strain gauges or other sensors are utilized in connection with more than one commissure post, the readings of the various sensors can be used in combination to make a diagnostic determination. For example, readings from a plurality of sensors can be averaged, or summed together, depending on the particular derivation/application being implemented.

Some amount of power may be necessary for powering the strain gauge and/or other components of the valve diagnostic system. For example, an excitation voltage applied to input leads of the strain gauge network 1088 can be provided from wireless power transfer, local power harvesting, local power storage, or other power generation and/or supply system. In one embodiment, one or more piezoelectric crystals can be used to generate power, which can be stored in a power storage device, such as a capacitor or the like. The voltage reading of the strain gauge can be taken from one or more of the output leads 1081. The valve 1010 can comprise signal processing circuitry (not shown) for performing preprocessing on the strain gauge signal, such as filtering, signal amplification, or the like.

Measuring the deflection of valve commissure(s) can be used to determine valve function, and commissure deflection can further relate to potential changes in heart function. Certain embodiments disclosed herein provide heart valve commissures comprising instrumentation configured to measure deflection of the commissure. Where such instrumentation comprises a strain gauge, the strain gauge can be disposed on or associated with a valve wireform, such as a stent member, as described above; the strain gauge, or other sensor device(s), can measure the strain in the wireform/stent as the valve cycles. In certain embodiments, optical instrumentation/methods can be used to measure the deflection of a heart valve under various pulsatile conditions.

Data retrieved relating to commissure post deflection can provide information indicating the amplitude of the closing pressure across the valve. In certain embodiments, such commissure deflection information, such as can be retrieved using a strain gauge on one or more commissure posts of a valve, can be used to determine heart rate. For example, the period of the commissure deflection signal can indicate a frequency of heart contractions (e.g., beats per minute (bpm)). Commissure deflection information can further be used to determine systolic and/or diastolic duration, wherein systolic duration provides a measurement of the period of time of the cardiac cycle when ventricles are contracted and diastolic duration provides a measurement of the period of time of the cardiac cycle when the heart is filling with blood.

In certain embodiments, commissure deflection information can be used to determine valve closing pressure. For example, the amplitude of the commissure deflection can indicate closing pressure based on the relationship between deflection and pressure. In certain embodiments, commissure deflection information can be used to determine isovolumetric contraction. For example, a strain gauge on a commissure post can be sensitive enough to sense the closing sound of, for example, the mitral valve. The time from mitral valve closure to aortic valve opening can provide the inferior vena cava (IVC) phase, and can be an indicator of blood volume in a patient.

In certain embodiments, commissure deflection information can be used to determine arterial pressure. For example, commissure deflection in a valve can indicate changes in one or more heart chambers, and can be used to derive arterial pressure. In certain embodiments, commissure deflection information can be used to determine a rate of change of pressure during valve closure. For example, the rate of deflection of the commissure(s) can indicate how quickly the valve closes, and therefore how quickly the pressure in the valve changes. Commissure deflection information can further be used to determine pressure differential between the inflow and the outflow of a heart valve, which can be a significant parameter with respect to heart function. In certain embodiments, a pressure sensor can be used in combination with commissure deflection sensor(s) to provide additional pressure change/differential information.

In certain embodiments, commissure deflection information can be used to determine blood flow. For example, turbulence vibrations in valve commissures can indicate flow, wherein changes in the turbulence can provide an indication of changes in flow, or possibly changes like thrombus on a leaflet. In certain embodiments, a prosthetic valve can be fitted with a flow sensor (e.g., ultrasonic Doppler flow sensor), which can be disposed in an upper/top region of the valve, wherein the flow sensor data can be used in combination with commissure deflection information to determine blood flow.

In certain embodiments, a heart valve having one or more commissure deflection sensors can further integrate one or more additional sensor devices, the readings from which can be used to supplement or interpret the data provided by the commissure deflection sensor(s). For example, a sensor associated with a pacemaker lead can be used in certain embodiments to provide additional information that can be used in connection with commissure deflection information. Additional devices/sensors that can be utilized in combination with commissure deflection sensor(s) can include blood pressure cuffs, electrocardiography sensors (ECG), temperature sensors, pulse oximetry sensors, or the like.

The above-referenced information that can be derived from commissure deflection data, as well as changes in such information over time, can be used as indicators of changes in heart function and be used by, for example, a physician in helping to provide early intervention in a patient that may be showing early signs of heart/valve function complications. The above-referenced types of information represent potential diagnostic information that can be gathered from commissure deflection sensor data. However, it should be understood that commissure deflection data can be used to derive other types of information not explicitly referenced herein as well. The information utilization and/or derivations disclosed above based on commissure deflection information can be implemented by one or more components of the system 300 of FIG. 3 and disclosed above. For example, commissure deflection information processing functionality can be implemented in one or more of the implant device 310 (e.g., by the controller 313), local monitor device 350 (e.g., by the controller 351, and/or the remote monitor device/system 360. Furthermore, the commissure deflection information processing functionality can be implemented using hardware, software, or a combination of hardware and software.

FIG. 21 shows a stent member 1997 for an implant device, such as a heart valve implant, wherein the stent member 1997 has an integrated strain gauge 1988 associated therewith. As referenced above, certain embodiments of the present disclosure can include implant devices having structural components with strain gage(s) attached thereto or associated therewith. For example, a strain gauge, as shown in FIG. 20, can be attached to valve component(s) using adhesive or other attachment mechanism. However, such attachment may not provide an ideal method for a clinical application. Furthermore, certain feasibility methods/systems can utilize an external strain gage amplifier to obtain signals from the strain gage, which may likewise not be ideal for clinical usage. Certain embodiments disclosed herein provide implant devices having one or more strain gages incorporated therein. Such devices can be associated with relatively simple manufacturing processes, and can be compatible with certain self-powering device configurations.

In certain embodiments, the strain gauge 1988 can be directly incorporated into the material (e.g., PET, Mylar PET) of the stent member 1997, such as at least partially on a commissure post 1998 of the stent member 1997, by laser etching, and depositing the conductor into the etched channels of the stent member 1997. In certain embodiments, the strain gauge 1988 can be printed on the stent member 1997, such as at least partially on a commissure post 1998 of the stent member 1997, without etching. Such processes can advantageously simplify certain manufacturing steps and/or reduce the likelihood of a strain gauge becoming separated. Incorporation of a strain gauge into the stent member 1997 can also facilitate electronically sealing the strain gauge, and can further provide a relatively inexpensive solution for measuring commissure deflection.

Figure 22:
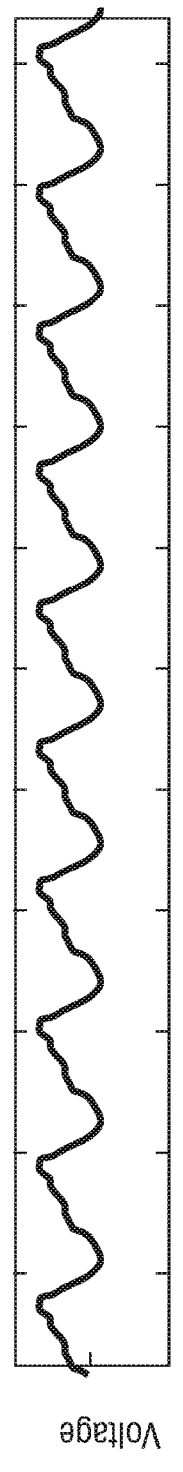
FIGS. 22-24 are graphs illustrating experimental results associated with a strain-gauge-integrated implant device according to an embodiment.
Figure 23:
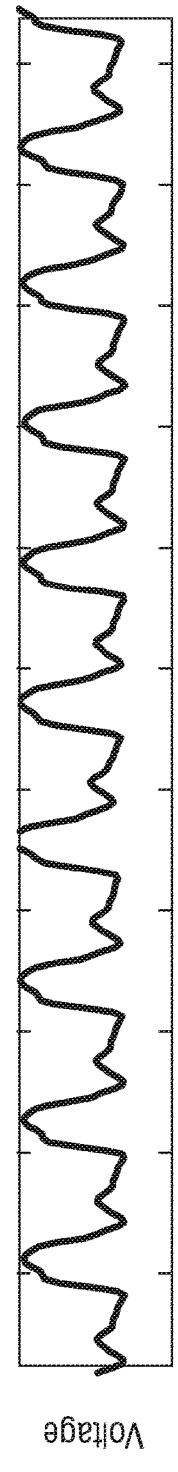
Figure 24:
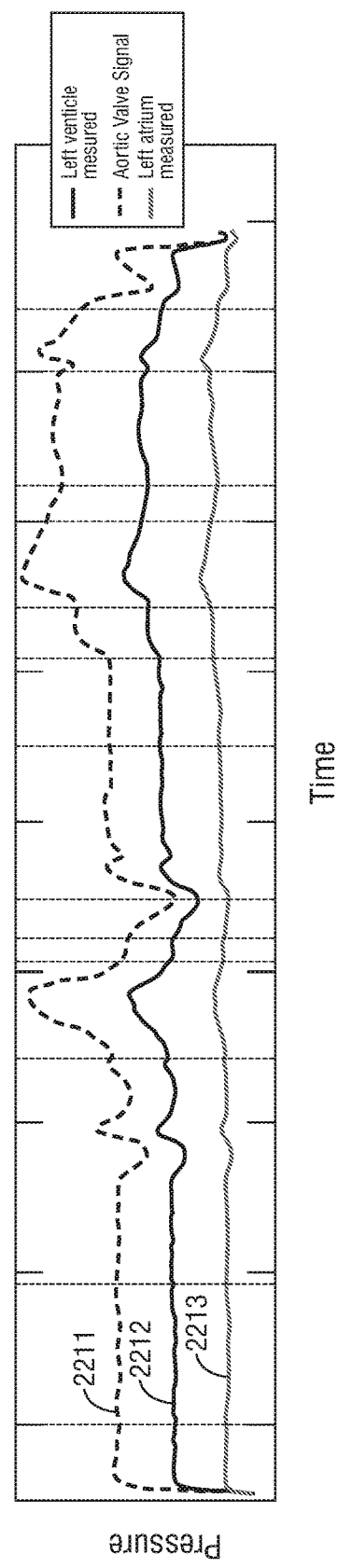

FIGS. 22-24 provide example experimental results achieved using embodiments of implant devices with integrated strain gauges. FIG. 22 shows data readings from an example strain gauge associated with a mitral valve implant device, whereas FIG. 23 shows data readings from an example strain gauge associated with an aortic valve implant device. For the examples of FIGS. 22 and 23, the strain gauges were disposed on commissure posts of the respective implant devices. The graphs of FIGS. 22 and 23 illustrate strength of the respective strain gauge signal over time. As shown in FIGS. 22 and 23, the strain gauge signal from the respective example implants generally tracks the cardiac rhythm, as expected. In certain embodiments, the intracardiac pressure can be derived from the strain gauge signals. For example, the graph of FIG. 24 illustrates the correlation between strain gauge data for the example strain gauge of FIG. 23 (i.e., aortic implant) and pressure data. In the graph of FIG. 24, the waveform 2211 represents the strain gauge signal converted to pressure for the aortic implant strain gauge as represented in FIG. 23. The waveforms 2212, 2213 represent actual pressure values over the same period as measured (e.g., using a pressure catheter/transducer) for the left ventricle and left aorta, respectively. As shown in FIG. 24, the pressure derived from the strain gauge signal generally correlates with the actual pressure values measured.

Pressure data derived from strain gauge signals integrated in implant devices in accordance with one or more embodiments of the present disclosure can be used to detect and/or predict hypotension, arrhythmia, and/or other cardiac events/conditions. Furthermore, in certain embodiments, strain gauge data can be used to determine stroke volume variation, hypertension, mitral pressure, electrical current, contractility (dp/dt), and/or other conditions. In certain embodiments, a strain gauge integrated with an implant device as disclosed herein can provide energy harvesting functionality, such as through the use of one or more piezoelectric crystals. The amount of power generated using strain gauge(s) can allow for data transmission to an external receiver every 15 minutes, or according to another interval.

Figure 25:
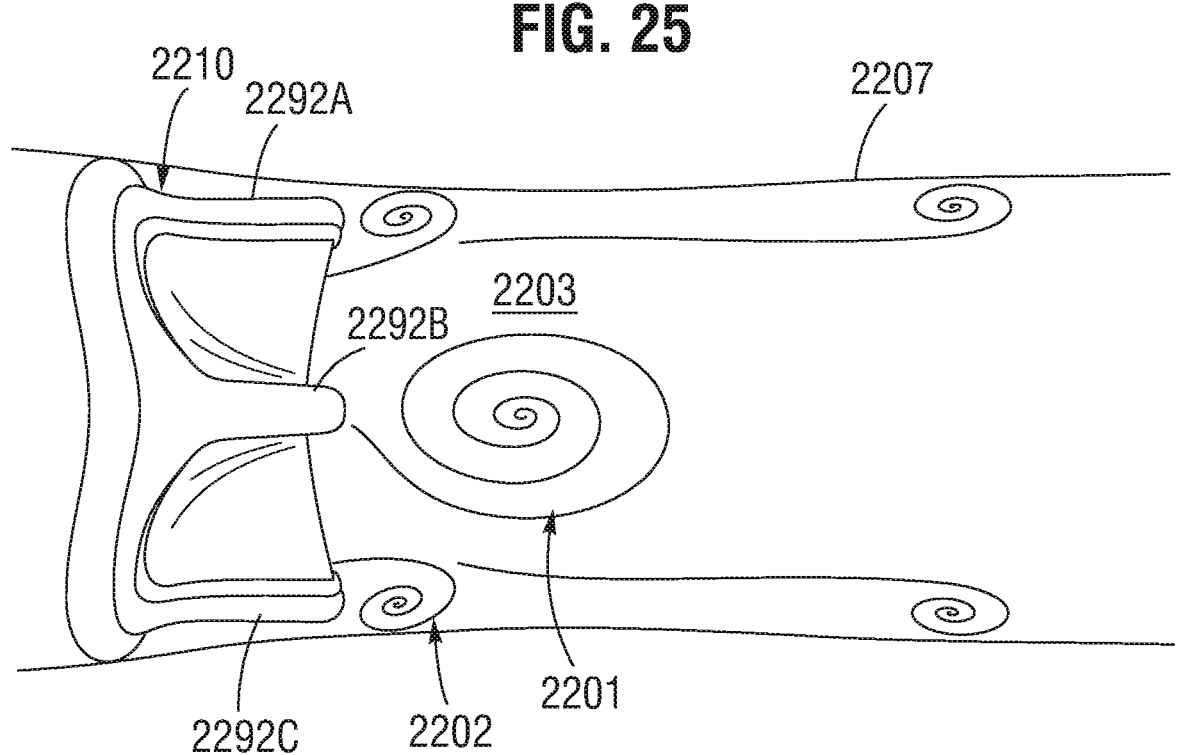
FIG. 25 provides a side view of a valve implant disposed in a fluid channel according to one or more embodiments.

Commissure deflection, which can be detected/monitored using a strain gauge or other mechanism, can be caused at least in part by blood flow-induced vibrations in a blood vessel. FIG. 25 shows a side view of a valve implant 2210 disposed in a fluid channel 2203, wherein fluid flow in the fluid channel experiences vortices caused at least in part by commissure post structures 2292A-C of the implant device 2210. In fluid dynamics, a Kármán vortex street may generally represent a repeating pattern of swirling vortices caused by the unsteady separation of fluid flow around blunt bodies, such as the commissure posts on heart valve stents, among possibly other structures of an implant device. For example, as shown in FIG. 25, a vortex 2201 can form near a commissure post 2292B, and one or more additional vortices (e.g., 2202) can form around one or more additional commissure posts (e.g., 2292C). Such vortices can induce detectable vibrations/deflections in the commissure posts.

Power Harvesting and Pressure Sensing Using Piezoelectric Elements

Figure 26:
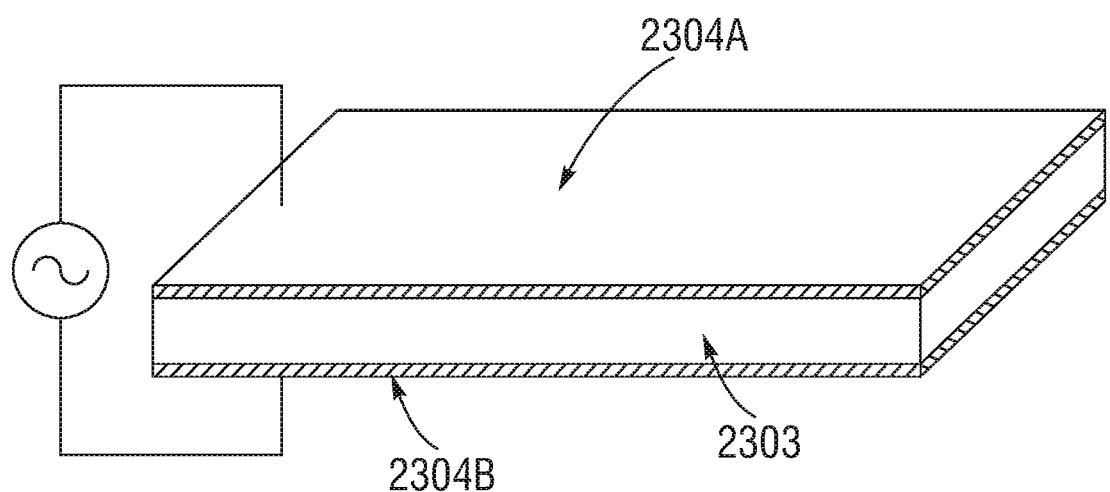
FIG. 26 is a diagram representing a piezoelectric device according to one or more embodiments.

Certain embodiments disclosed herein provide for the utilization of commissure deflection activity for power generation, wherein such power can be used to power one or more components of an associated implant device or other electrical component(s). For example, piezoelectric elements can be associated with the commissure post(s) such that pressure/strain on the commissure post(s) can cause corresponding pressure/strain on the piezoelectric element(s). By straining the piezoelectric elements (e.g., through direct piezoelectric effect), the commissure post vibrations can generate charge on the surface of the piezoelectric polymer. The resulting capacitive buildup in the polymer can provide a voltage source that can be used to, for example, trickle-charge a battery, which can be part of the implant or disposed at a separate location, to power various devices, such as blood pressure sensors, blood glucose meters, pacemakers, and/or other devices. FIG. 26 illustrates a diagram representing a piezoelectric device including parallel plates 2304A, 2304B comprising metaling layers, wherein a piezoelectric polymer 2303 is disposed between the plates. In certain embodiments, piezoelectric crystals can produce power as they are deflected.

Methods for strain gauging and powering a heart valve using piezoelectric film integrated into a heart valve or other implant device to take advantage of fluid and structural vibration energy for harvesting power can advantageously provide a relatively simple and/or convenient means for powering implant devices. Energy harvested from commissure post deflection can be used to power a piezoelectric cell. In certain embodiments, the power generated through commissure post deflection using piezoelectric element(s) may not be sufficient to support continuous powering of electrical functionality for an implant device, but can be used to charge a capacitor to power intermittent transmission of data, or to provide supplemental power for various purposes.

Valve implant devices having integrated sensor functionality in accordance with embodiments disclosed herein can be configured to transmit physiological signals to an external device that performs certain data processing to monitor, for example, relevant physiological predictors of cardiovascular instability. In certain embodiments, the sensor signal(s) can be derived from piezoelectric material and/or other non-piezoelectric sensors; the piezoelectric material can also power the wireless transmission circuitry to transmit the sensor data. In certain embodiments, the valve implant can integrate piezoelectric material on stent post structure(s) (e.g., PET, Mylar PET structures). In certain embodiments, a stent member, rather than comprising a PET structure, can include a piezoelectric assembly structure, which can be configured to bend during normal cardiac operation, thereby creating a voltage differential across the leads of the piezoelectric sensor, which can be harvested as an energy source for the implant device, or one or more associated devices.

Powering implant devices with the body's own energy according to embodiments disclosed herein can provide one or more advantages. For example, self-powering can reduce or eliminate the need for additional batteries or other power sources, which may require replacement, as well as external power sources, which may require cable or other attachments. With integrated power-generation functionality, sensor devices/assemblies can advantageously allow for smaller-scale devices, which can improve implantability prospects. For example, use of a relatively small piezopolymer electricity generator in place of a larger battery power source can reduce device/assembly size, thereby providing more space for diagnostic features and/or wireless communication components, such as Bluetooth and Radio-frequency identification (RFID) controllers, antennas, and the like.

Certain embodiments disclosed herein provide relatively small, flexible, multi-layered piezoelectric-polymer devices integrated in prosthetic heart valves (or annuloplasty rings) to generate reliable, long-term electricity. Such piezoelectric energy generators can harvest energy not only from movement-induced vibrations of support frames, but also flow-induced vibrations, such as Kármán vortices, as explained above.

Figure 27:
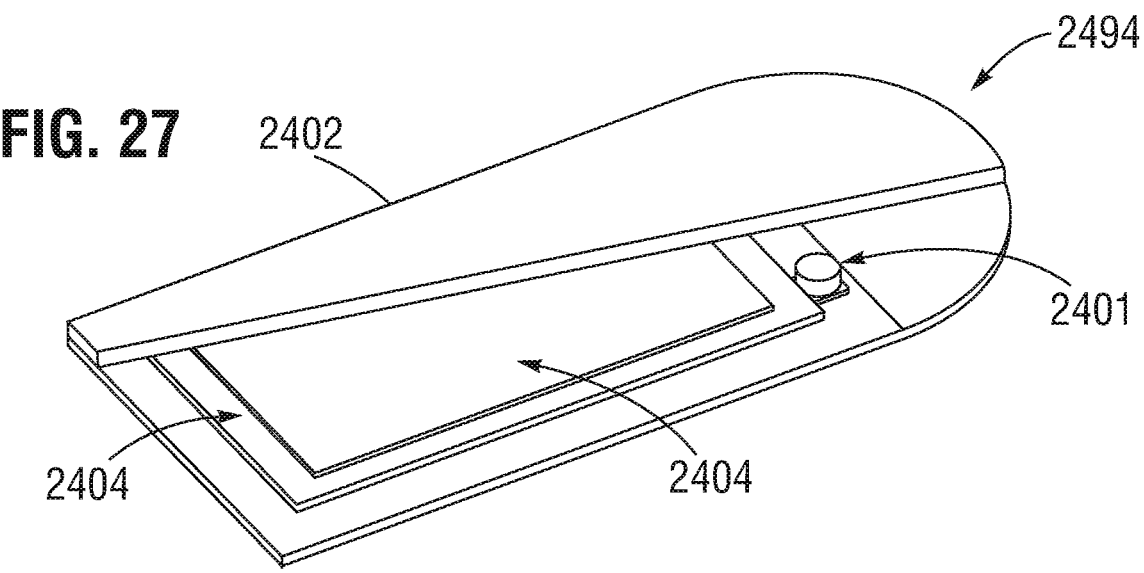
FIG. 27 provides a cut-away view of a multi-layered piezoelectric-polymer generator assembly according to one or more embodiments.

FIG. 27 provides a cut-away view of a multi-layered piezoelectric-polymer generator 2494 according to one or more embodiments. This electricity generator 2494 can be fabricated using a piezoelectric polymer, which may be desirable due to the relatively high piezoelectricity, flexibility, and/or biocompatibility that can be associated with such structures. Unlike piezoelectric ceramics, in which the crystal structure of the material may generally produce electrical energy, piezoelectric polymers can utilize intertwined long-chain molecules to attract and repel each other when an electric field is applied thereto. Furthermore, compared to piezoelectric ceramics, piezoelectric polymers can provide acoustic impedances closer to that of water and/or human tissues, and can have relatively higher voltage constants. For piezoelectric polymers, not only can relatively high sensitivity be an attractive feature for copolymers, but piezoelectric polymers can also crystallize from the melt or from solution in a polar phase. Therefore, it is possible to fabricate such devices in different shapes (e.g., curved surfaces), and pole the copolymer without prior stretching (e.g., reduced fabrication time).

The power generator 2494 can be a portion of a stent post of a heart valve implant device. The power generator 2494 can have a laminated structure wherein a parallel plate structure including a piezoelectric polymer 2404 is disposed between conductive (e.g., metallic) layers, including a top electrode 2404 and a bottom electrode (not shown). The conductive layers (e.g., 2404) can be used as electrodes to define the area of the capacitive structure and conduct the generated electric current. Pressure differential caused by the vortices/vibrations in the fluid flow through the valve can cause oscillatory deformations in the surface of the piezoelectric polymer. The conductive layers (e.g., 2404) can comprise metal having desirable flexibility to allow the stent post to maintain flexibility.

Figure 28:
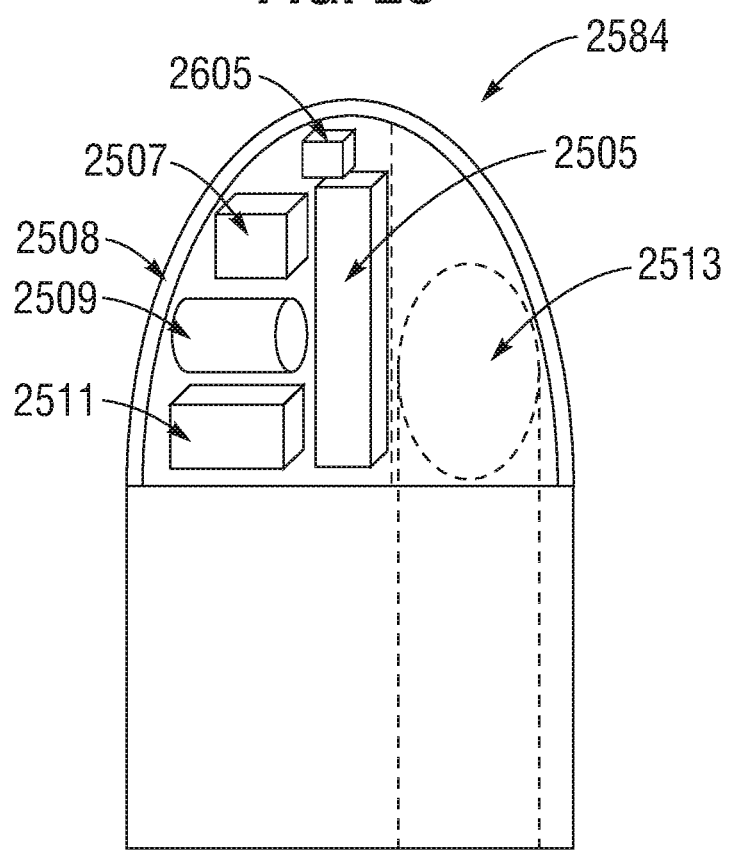
FIG. 28 shows a power generator valve stent post assembly according to one or more embodiments.

While FIG. 27 shows an embodiment of a multi-layered piezoelectric-polymer generator 2494, FIG. 28 shows a possible location of power generator and/or sensor circuitry 2584 on a valve stent post. As deformations in the piezoelectric surface are relied upon to generate capacitive buildup, allocation of the power generator circuitry 2584 in an area providing turbulence or vibration can improve efficiency. As shown in FIG. 25 and described above, vortices can be generated around the commissure posts of heart valve stents. Therefore, the distal end portions of commissure post structures can provide a desirable location for the power generator 2584. Although embodiments are disclosed herein for integrating power generators with commissure post structures, other locations or structures of a heart valve, or other implant device, can provide suitable locations for power generators in accordance with the present disclosure.

The power generator circuitry 2584 can provide power for a wireless monitoring system, as described in detail herein, which can include one or more sensory components 2605 adapted to measure one or more hemodynamic parameters inside a cardiac chamber of a patient. The power generator circuitry 2584 can further comprise one or more of a controller or communication unit 2505 that receives sensor data from the sensory component(s) 2605, data storage devices 2507, capacitors or other discrete passive components 2509, analog-to-digital converters 2511 or other signal processing components, and electrical connections and/or structural features 2513 for coupling to a transmission antenna (not shown) to transmit a signal containing data corresponding to the one or more hemodynamic parameters, or to provide structural support.

Figure 29:
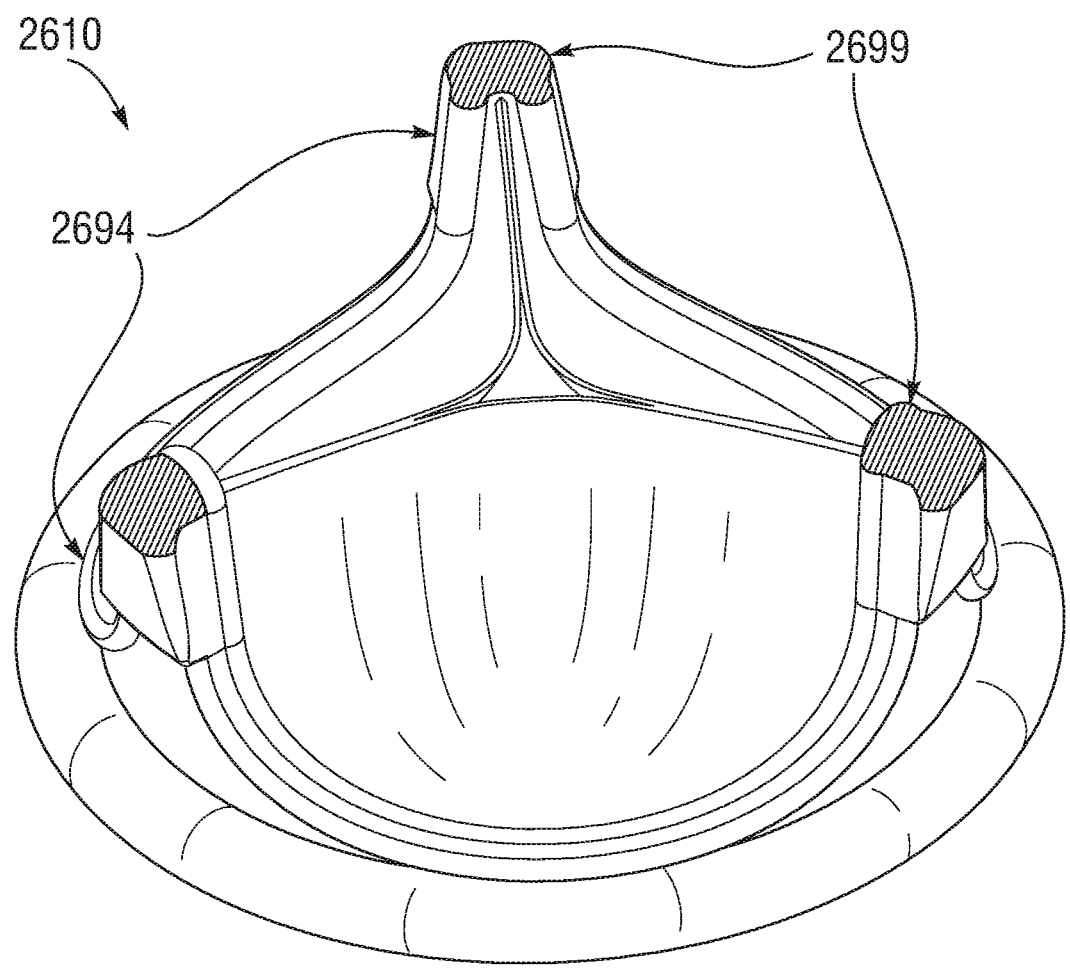
FIG. 29 provides a perspective view of a valve implant device according to one or more embodiments.

FIG. 29 provides a perspective view of a valve implant device 2610 according to one or more embodiments. The implant device 2610 includes commissure posts 2694, wherein power generator systems according to embodiments disclosed herein can be disposed at least partly at or within end portions 2699 of one or more of the commissure posts of the implant device 2610. For example, an energy harvester can be placed underneath a cloth layer of the commissure posts.

Figure 30:
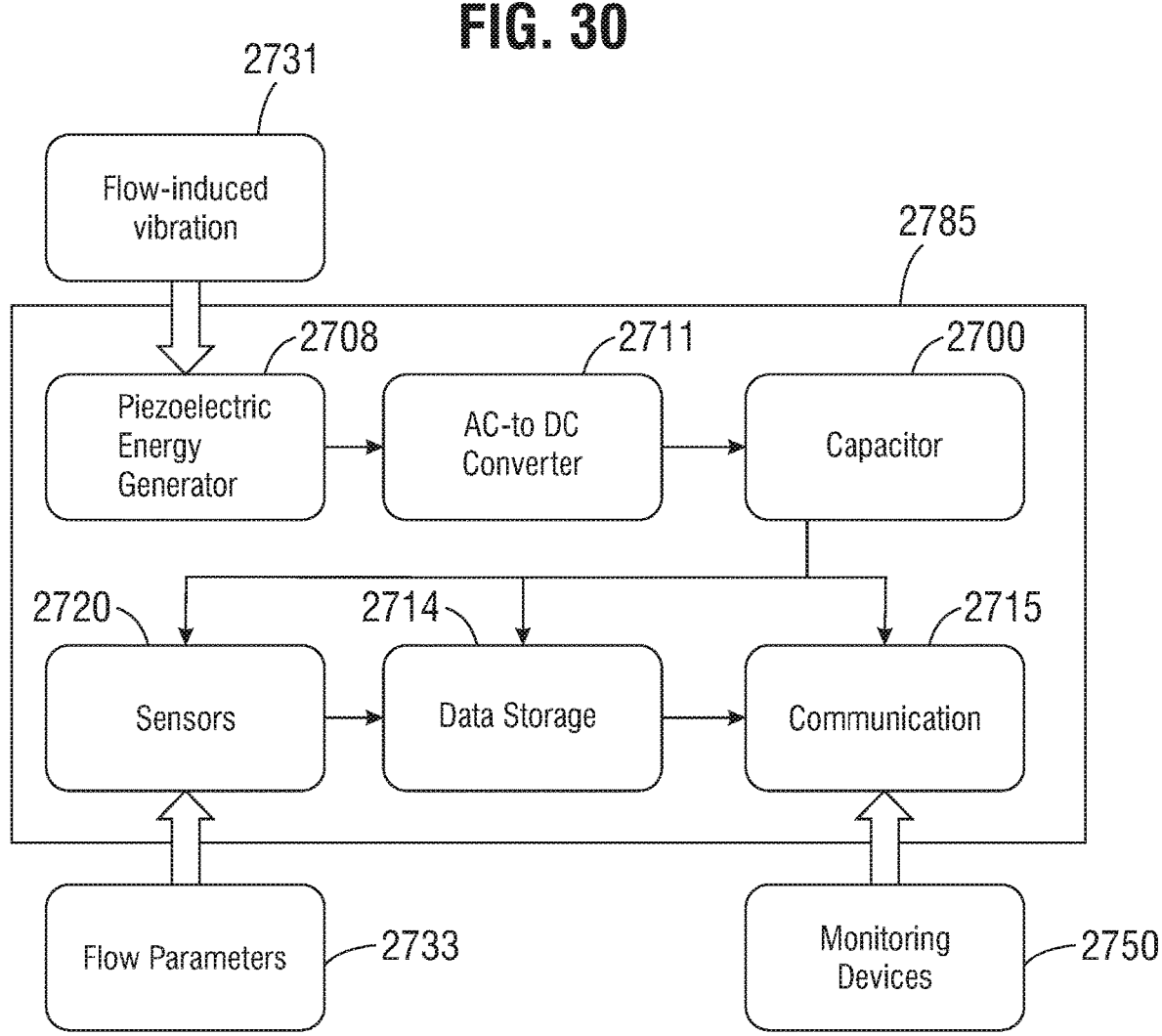
FIG. 30 is a block diagram of a self-powered sensor module according to one or more embodiments.

FIG. 30 is a block diagram of a self-powered sensor module 2785, which can be integrated in an implant device configured to provide wireless monitoring functionality according to one or more embodiments disclosed herein. The sensor module 2785 can provide a blood flow power generator that can be integrated with a prosthetic heart valve. The module 2785 includes an energy generator 2708, such as a piezoelectric energy generator, which can be configured and/or positioned to use vibrations from support frame movement and/or fluid flow to generate relatively small amounts of reliable, long-term electrical power. In certain embodiments, the module 2785 is relatively small and configured to be disposed underneath a cloth and/or other layer of a commissure post structure of a heart valve stent member, wherein neither moving parts nor rotating motion is required to facilitate the energy-harvesting functionality of the device. Therefore, the module 2785 can operate relatively quietly and/or provide relatively little disruption of blood flow dynamics. In addition, where the module 2785 has a low-impact profile, additional risk for local coagulation and/or clotting of the blood (e.g., thrombosis) can be reduced. In certain embodiments, the energy generator 2708 comprises piezo-ceramic materials, which can advantageously be biocompatible. In addition, the module 2785 can also help to avoid damage to heart tissue due to not being directly attached to the heart in certain embodiments.

Figure 31:
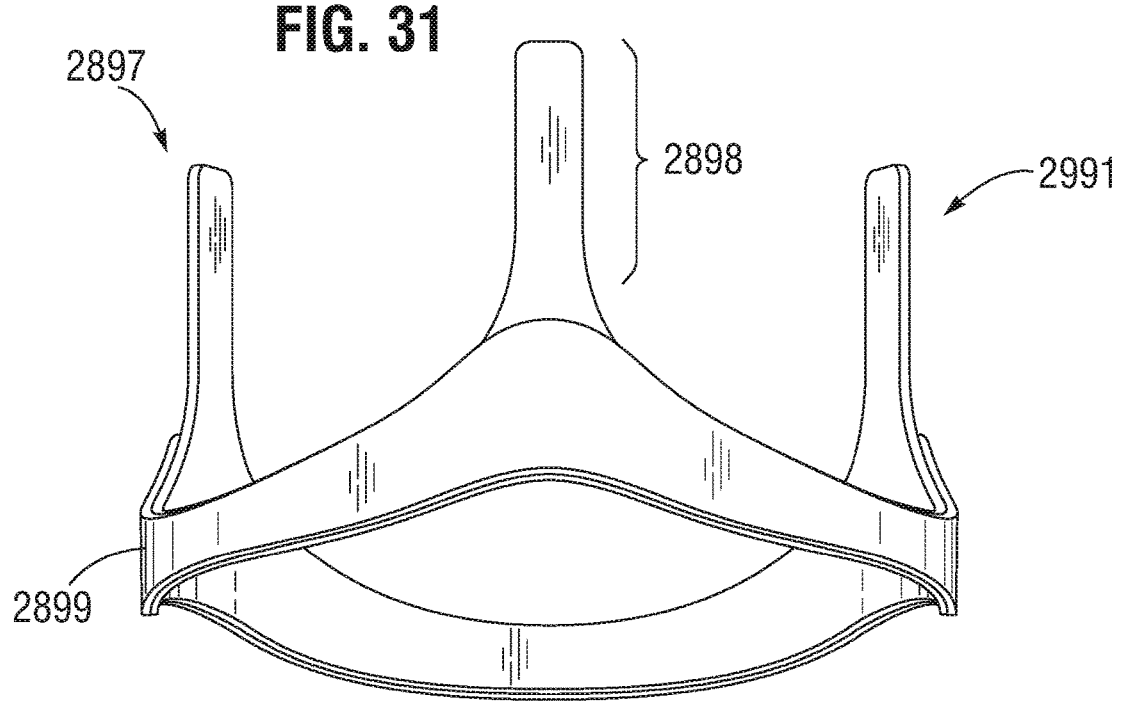
FIG. 31 provides a perspective view of a stent member of a heart valve implant device according to one or more embodiments.

FIG. 31 illustrates a stent member 2897 of a heart valve implant device according to one or more embodiments. The stent member 2897 can comprise a rigid stiffening band 2899, which can be comprised of, for example, metal or other rigid material, as well as a flexible (e.g., plastic/PET) band 2896 that includes a commissure support portion 2898, which can fit at least partially within the upwardly-projecting commissure regions (not shown) of a valve frame member. In certain embodiments, one or more of the commissure support portions 2898 of the flexible band 2896 can be comprised of a laminated piezoelectric structure, such as that shown in FIG. 27 and described above. For example, the piezoelectric structure can occupy some or all of the portion 2898 of the stent member. The piezoelectric structure can be utilized for either or both of generating pressure-related signals that can be interpreted according to embodiments disclosed herein, and power generation for use for data transmission and/or other purpose. For example, piezoelectric sensor readings can be indicative of blood pressure or other physiological characteristics. Furthermore, the various piezoelectric features and elements disclosed herein in connection with certain embodiments can utilize any suitable or desirable type of piezoelectric elements within the scope of the present disclosure.

The piezoelectric structure can be configured generate power that can be used for sensor and/or transmitter operation as disclosed herein. As described in detail above, in order to monitor a patient telemetrically, valve-integrated sensors may need to be powered. Although batteries can be installed in a valve in certain embodiments, they may require recharging and/or take up limited real estate in the valve assembly. In certain embodiments, valves in accordance with the present disclosure use the voltage differential created by the movement of piezoelectric film structures integrated in the flexible commissure support as a signal, and also possibly store this charge to be used as an energy source. By using piezoelectric material, data can be transmitted without the need to actively recharge a battery or emit a power signal to the heart valve.

Figure 32:
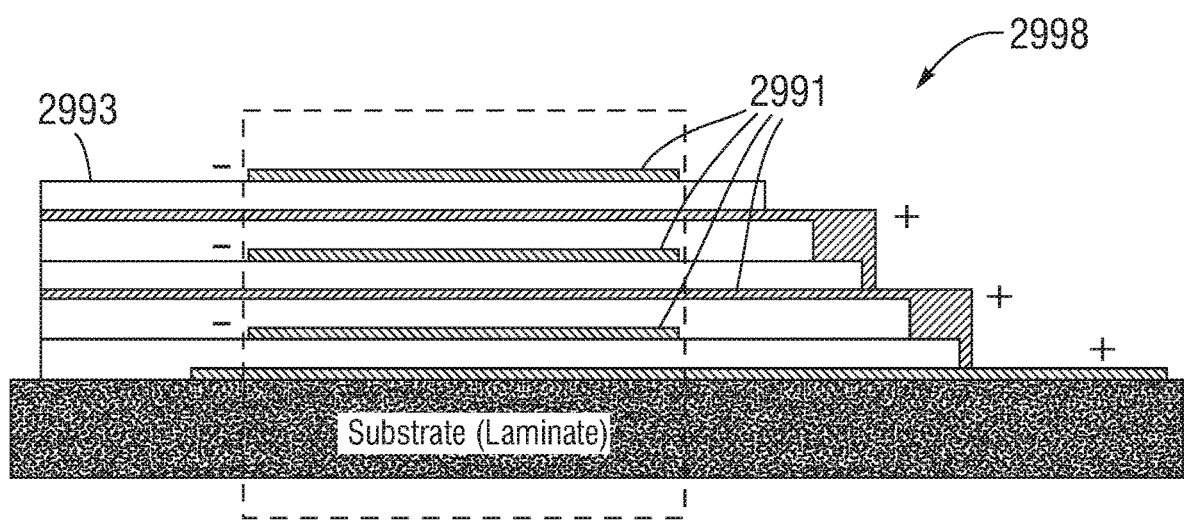
FIG. 32 provides a cross-sectional side view of a piezoelectric-integrated flexible stent band structure according to one or more embodiments.

The voltage/signal generated by the piezoelectric film can be increased by corrugating or stacking the sheets of piezoelectric. FIG. 32 shows a cross-sectional side view of a piezoelectric-integrated flexible stent band structure (e.g., 2898) according to one or more embodiments. For example, the flexible piezoelectric stent band structure 2998 can be part of a commissure support form of a stent member of a valve implant.

The stacked piezoelectric structure 2998 can comprise layers of piezoelectric material 2993 separated by conductive (e.g., metal) plates 2991. The structure 2998 can comprise any suitable piezoelectric material 2993, such as piezoelectric fiber composites, piezoelectric films, or piezoelectric ceramics. In certain embodiments, it may be desirable to use flexible piezoelectric elements, such as, for example, flexible piezoelectric fiber composite elements, which can be configured to generate an electrical charge when they are bent or flexed. The piezoelectric elements 2993 can be disposed in electrical contact with electrodes 2991 that conduct the electrical energy to the implant device for immediate use or for storage for later use.

In certain embodiments, the layers of piezoelectric sheets can be laminated to provide similar thickness and flexibility to a plastic (e.g., PET, Mylar PET) band member of a valve implant, such as that shown in FIG. 11 and described above. By combining the piezoelectric energy generator with the stent band member, the need for a separate plastic band can be eliminated while maintaining the structural integrity of the valve design.

Embodiments of piezoelectric-integrated implants can be well-suited for receiving power transmission through ultrasound transmission, as shown in FIG. 8 and described above. For example, the voltage differential created by the movement of the piezoelectric element and/or associated structure/component can be used as a signal and/or the charge can be used as an energy source. Furthermore, a piezoelectric structure, such as the piezoelectric-integrated flexible stent band 2898 can serve as a receiver for receiving ultrasound energy. Such devices can be particularly suited for ultrasound reception because, compared to radio-frequency (RF) signals, ultrasound signals comprise mechanical waves that can propagate through medium, such as biological tissue, blood, fat, etc., with less loss in some implementations. Therefore, ultrasound wireless power charging can be relatively efficient in energy transmission compared to some RF wireless power charging systems.

Figure 33:
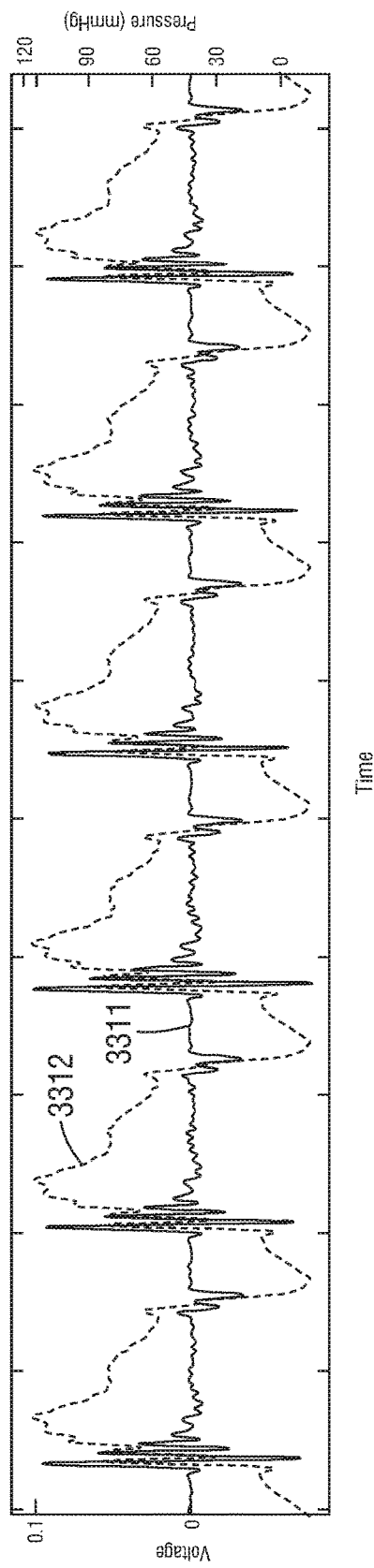
FIGS. 33 and 34 are graphs illustrating experimental results associated with a piezoelectric-integrated implant device according to an embodiment.
Figure 34:
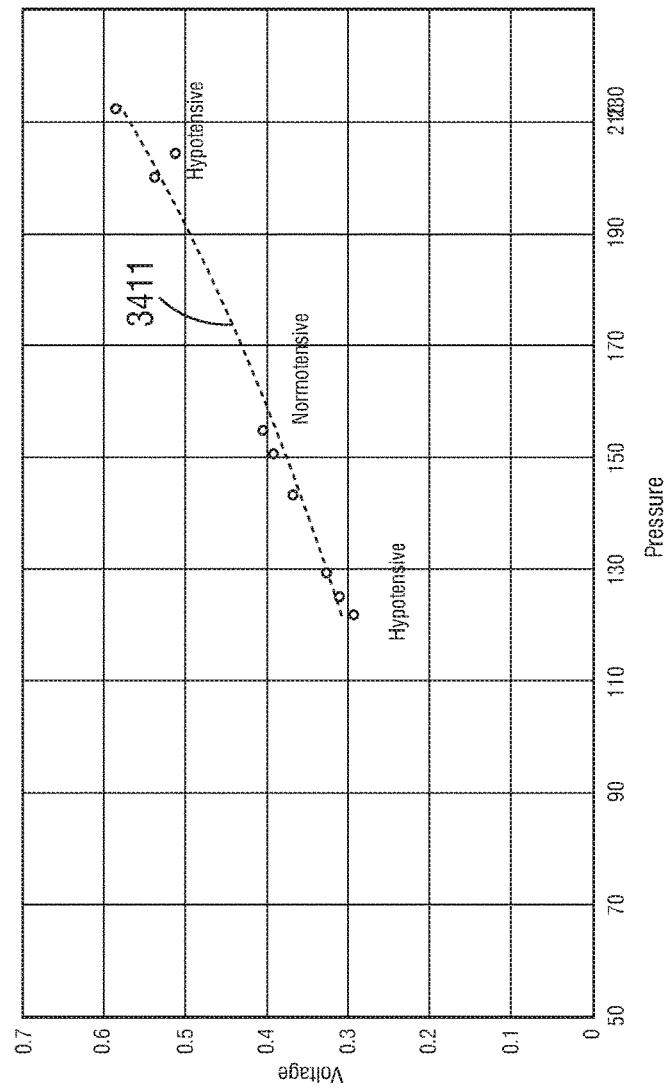

As referenced above, piezoelectric sensors integrated with implant devices in accordance with one or more embodiments disclosed herein can generate signals indicative of one or more physiological conditions, such as blood pressure. FIGS. 33 and 34 provide example experimental results achieved using embodiments of implant devices with integrated piezoelectric elements. FIGS. 33 and 34 show data readings from example piezoelectric elements associated with an aortic valve implant device. The waveform 3311 of the graph of FIG. 33 illustrates the strength of the piezoelectric signal over time. As shown in FIG. 33, the strain gauge signal from the example implant is cyclical in accordance with the cardiac cycle, as expected. In certain embodiments, the intracardiac pressure can be derived from the piezoelectric signal. In the graph of FIG. 33, the waveform 3312 represents the actual pressure as measured (e.g., using a pressure catheter/transducer).

The graph of FIG. 34 shows the peak-to-peak voltage of the piezoelectric signal 3311 relative to the actual measured pressure (peak back pressure in mmHG), and demonstrates the correlation between the piezoelectric signal and the actual pressure. Therefore, as demonstrated by FIG. 34, implant devices with integrated piezoelectric element(s) can be used as pressure sensors in certain configurations. In some implementations, the piezoelectric sensor signal can be converted to a pressure reading for various purposes, such as for determining flow pressures (e.g., hypotension, hypertension, etc.). FIG. 34 shows examples of piezoelectric signal values that can correlate with various pressure conditions (e.g., hypotension, normal, hypertension); the data shows good correlation between the piezoelectric signal and pressure over a range from hypotensive to hypertensive.

Piezoelectric signals can be used to identify hypotension, arrhythmia, stroke volume variation, hypertension, mitral pressure, electrical current, contractility (dp/dt), and/or other conditions. The amount of power generated using piezoelectric element(s) can allow for data transmission to an external receiver every 15 minutes, or according to another interval. The energy generated by the piezoelectric-integrated implant device can be represented by the energy generated by the piezoelectric element(s) (e.g., 1.7 µW*) minus the relevant energy transmission loss.

Implant/Patient Monitoring Processes

Figure 35:
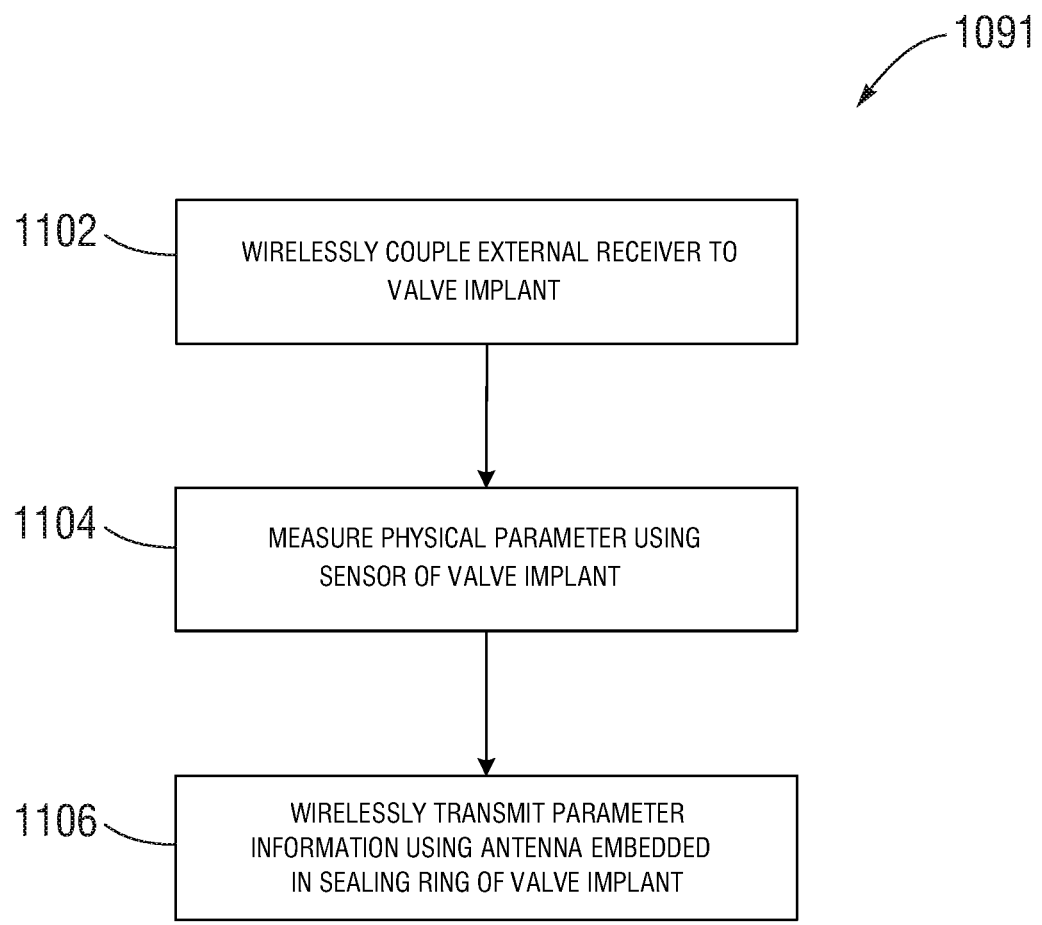
FIG. 35 is a flow diagram illustrating a process for monitoring a postoperative implant device and/or patient associated therewith according to one or more embodiments.

Disclosed herein are systems and devices which can be utilized in the monitoring of patients that have received implant devices, such as cardiac valve implant devices as disclosed herein. FIG. 35 is a flow diagram illustrating a process 1100 for monitoring a postoperative implant device and/or patient associated therewith. The process 1100 can be implemented at least in part by one or more of the entities or components of the system 300 shown in FIG. 3 and described above. In certain embodiments, the process 1100, or portions thereof, can be implemented by a physician or healthcare provider, or other user/entity. The process 1100 involves, at block 1102, wirelessly coupling an external receiver device to an implant device implanted in a patient, such as a heart valve implant device. At block 1104, the process 1100 involves measuring a physical parameter using a sensor of the implant device. The physical parameter can be associated with the implant patient and/or the implant device. At block 1106, the process 1100 involves wirelessly transmitting parameter information based on the measured physical parameter using an antenna or other transmitter assembly or component embedded in a sealing ring or other structure of the implant device.

Figure 36:
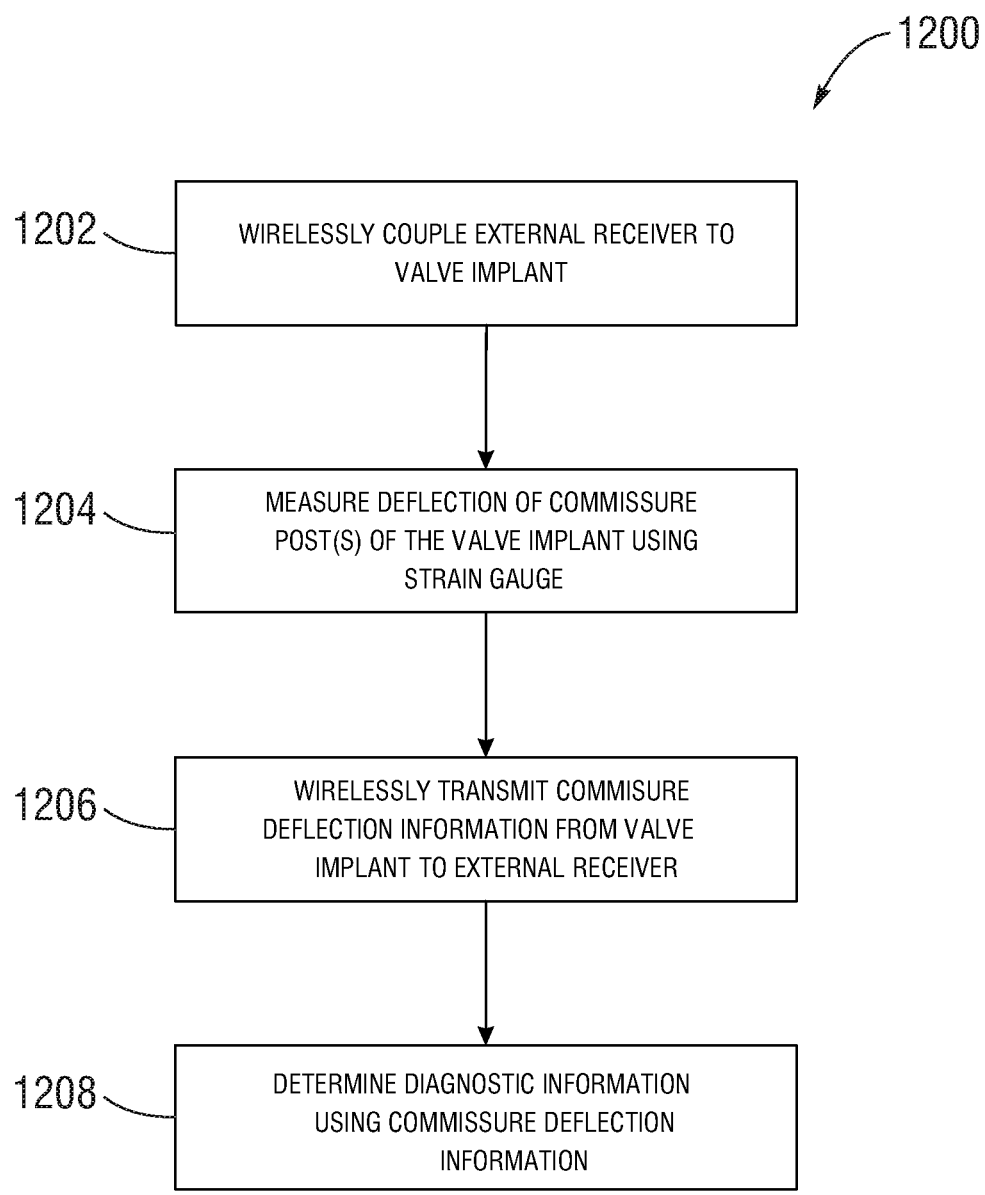
FIG. 36 is a flow diagram illustrating a process for monitoring a postoperative implant device and/or patient associated therewith according to one or more embodiments.

FIG. 36 is a flow diagram illustrating a process 1200 for monitoring a postoperative implant device and/or patient associated therewith. At block 1202, the process 1200 involves wirelessly coupling an external receiver device to a valve implant device implanted in a patient. A block 1204, the process 1200 involves measuring the deflection of one or more commissure posts of the valve implant using a strain gauge device, which can be attached to, or etched into, one or more commissure posts of the valve implant. At block 1206, the process 1200 involves wirelessly transmitting commissure deflection information from the valve implant to the external receiver device. A block 1208, the process 1200 involves determining diagnostic information using the commissure deflection information received wirelessly from the implanted valve device. The diagnostic information can include, for example, heart rate information, systolic duration information, diastolic duration information, valve closing pressure information, isovolumetric contraction information, pressure change information, blood flow information, blood pressure information, or other type of diagnostic information.

Transcatheter Heart Valve

The principles disclosed herein can be applicable to any suitable type of implant device, such as certain pericardial heart valve implants, or the like. For example, in certain embodiments, wireless data and/or power transmission capability can be implemented in connection with a transcatheter heart valve (THV).

FIG. 37 is a perspective view of an exemplary embodiment of a transcatheter heart valve 3010 having a sensor module 3085 for sensing one or more environmental or physiological parameters, as well as an antenna structure 3080 for wireless data and/or power transfer. The sensor 3085 and/or antenna 3080 devices can be designed in accordance with various features/functionality described above.

The THV 3010 can include a support frame 3090, which can comprise a grated framework, such as a stent, configured to secure the THV 3010 within or adjacent to a defective valve annulus of the heart. The support stent structure 3090 can further provide stability and prevent the THV 3010 from migrating after it has been implanted. The support stent structure 3090 can comprise any suitable or desirable material, such as memory metal, metal alloys such as stainless steel or cobalt chromium, and/or polymers. Furthermore, the support stent structure 3090 can have configurations other than that shown in FIG. 37. For example, the support stent structure 3090 can have a different shape, more or fewer vertical support bars, and/or additional structures for added stability. In certain embodiments, the support stent structure 3090 can comprise a strut mesh and/or sleeve structure.

The support stent structure 3090 can be secured to a valve structure, for example, valve leaflet assembly 3093. The valve leaflet assembly 3093 can include a plurality of leaflets that collectively function as a one-way valve by coapting with one another. With respect to, for example, prosthetic aortic valves, a valve leaflet assembly can comprise three leaflets, as shown. However, it will be appreciated that THV implants in accordance with the present invention can have a greater or lesser number of leaflets. The various components of the valve leaflet assembly 3093 can be wholly or partly formed of any suitable biological material or polymer such as, for example, polyethylene terephthalate (PET), ultra-high-molecular-weight polyethylene (UHMWPE), polytetrafluoroethylene (PTFE), or the like.

The valve leaflet assembly 3093 can be attached to any suitable portion(s) of the stent 3090, such as at commissure portions 3094 associated with the commissure between adjacent leaflets. The commissure portions 3094 can include one or more eyelets or engagement features designed to facilitate the suturing or securing of the respective commissure portion to stent structure 3090.

The sensor module 3085 and/or antenna structure 3080 can be physically coupled to the THV 3010 in some way, such as via a tether 3089, or other connection means. The tether 3089 or other connection can serve to maintain the sensor module 3085 and/or antenna structure 3080 within physical proximity to the THV 3080, which can help ensure that sensor data generated by the sensor 3085 is relevant to the operation/function of the THV 3010.

In certain embodiments, the THV 3010 and support structure 3090 can be radially compressed into a compressed state for delivery through a patient's vasculature, as shown in FIG. 38. In addition, the antenna structure can likewise be configured to be radially compressed, as shown, in order to allow for transcatheter deliver. FIG. 38 shows the antenna structure 3080 in a folded configuration. The antenna structure 3080 and/or support structure 3090 can be configured to self-expand to a natural, uncompressed or functional state having a preset diameter once positioned in a desirable location within the patient's vasculature.

Implant with Integrated Electrocardiograph

Monitoring patient cardiac rhythm and/or other parameters can be important for detecting life-threatening cardiac events in patients. Cardiac rhythm can be monitored by detecting electrical impulses in and/or around the heart (e.g., electrocardiography). However, heart monitoring through the use of external leads placed on the chest and limbs, as in accordance with certain techniques, may be undesirably invasive, and therefore may be used primarily acutely, and may not be suitable for continued, post-operative monitoring. Alternative electrocardiography techniques may involve implanting a pacemaker in a patient, which may be undesirably invasive and costly. Embodiments disclosed herein provide for the integration of electrocardiography technology in an implant device, such as a prosthetic heart valve, wherein the implant device is capable of detecting cardiac rhythm by determining voltage vectors associated with electrical impulses in fluid passing through the implant device.

Figure 39:
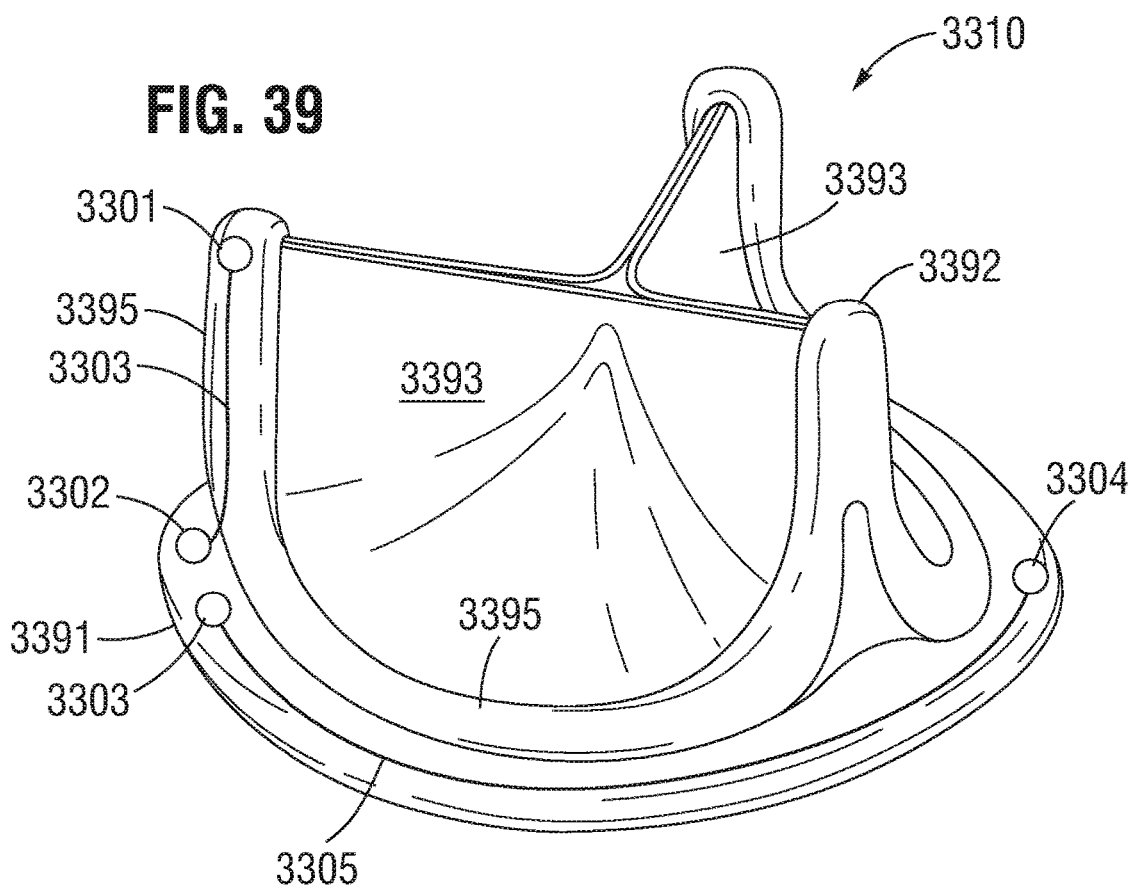
FIG. 39 provides a perspective view of a valve implant device according to one or more embodiments.

In certain embodiments, sensor-integrated implant devices comprise sensor(s) configured to sense electrical impulses associated with the heart. For example, FIG. 39 illustrates an implant device 3310, such as a heart valve or other cardiac implant, which incorporates one or more electrical sensors for monitoring electrical cardiac signals.

During each heartbeat, a healthy heart may display an orderly progression of depolarization of cells in the heart, which may give rise to electrical charges that can be detected to provide data for electrocardiogram (ECG) representation. ECG data can indicate various characteristics relating to the structure of the heart and the function of its electrical conduction system. For example, an ECG can be used to measure the rate and rhythm of heartbeats, the size and position of the heart chambers, the presence of damage to the cells or conduction system of the heart, the effects of cardiac drugs, or other potentially significant characteristics. The terms "electrocardiogram," "electrocardiograph," "electrocardiography," and "ECG" are used herein according to their broad and ordinary meanings, and may be used interchangeably in certain contexts herein to refer to devices, methods, data, and/or systems for detecting, processing and/or analyzing electrical impulses of the heart.

The implant 3310 can be configured to provide intracardiac ECG transmission signals, which can be generated using one or more electrodes for detecting cardiac rhythm within the heart. The implant 3310 includes a plurality of example positions for electrical leads (3301, 3302, 3303, 3304). The terms "electrode" and "lead" are used herein according to their broad and ordinary meaning, and may be used substantially interchangeably in certain contexts herein to refer to an electrical contact and/or reference node. Each of the electrodes (3301, 3302, 3303, 3304) can comprise a conductive pad fixed to one or more structural components of the implant 3310, such as a commissure post 3392, annulus or sealing ring 3391, leaflet 3393, or other component of the implant 3310. Although the implant device 3310 comprises three commissure posts 3392 and three leaflets 3393, valves or implants having other numbers of posts or leaflets can be used.

The electrodes (3301, 3302, 3303, 3304) can be positioned to come in electrical contact with fluid (e.g., blood) flowing in a blood vessel in which the implant 3310 is implanted. In certain embodiments, it may be desirable for one or more of the ECG electrodes to be disposed on a portion of the implant 3310 that is in physical contact with, or in physical proximity to, biological tissue, such as the blood vessel or heart wall. Tissue overgrowth on the electrode(s) can improve electrical signal strength at the electrode(s) in some configurations.

Although a plurality of electrodes (3301, 3302, 3303, 3304) are illustrated, it should be understood that any number of electrodes can be implemented, including a single electrode coupled to a controller in an embodiment. In one embodiment, the implant 3310 comprises two electrodes or leads. In various embodiments, the implant 3310 comprises 4, 6, 8, 10, 12 or more electrodes or leads. Furthermore, it should be understood that each of the illustrated electrical features (3301, 3302, 3303, 3304) can be an electrode, lead, or controller configured to receive and process electrical signals provided by one or more electrodes or leads. For example, in an embodiment, each ECG electrode of the implant 3310 is electrically coupled (e.g., via an electrical wire or path 3303, 3305) to a controller. With reference to FIG. 39, for example, where one of the electrical elements 3301, 3302 is an electrode, the other can represent the ECG controller; where one of the electrical elements 3303, 3304 is an electrode, the other can represent the ECG controller. The ECG controller can comprise amplifier circuitry, such as a differential amplifier (e.g. instrumentation amplifier) for amplifying the voltage difference between the electrodes/leads for processing. In certain embodiments, the ECG controller comprises circuitry for converting an analog voltage difference signal into a digital signal, wherein the implant device 3310 is configured to transmit the digital signal wirelessly, as described in detail above. The ECG controller can be similar to the electronic sensor modules 185, 485 illustrated in FIGS. 4 and 12, respectively, and described above.

The electrode(s)/lead(s) of the implant 3310 can provide the source of measurement of a vector, wherein comparison between two electrodes (e.g., where one electrode represents a common voltage reference, or ground reference) can provide a voltage reading that can be used for ECG generation/analysis. Suitable positions for the electrodes can be on or about the annulus periphery 3391, at desirable point(s) on a frame post structure, or other position(s).

The implant device 3310 can further comprise a transmitter assembly (not shown), such as a wire coil structure and associated circuitry, as described above. With electrodes and a transmitter integrated with the implant 3310 (e.g., valve), changes in voltage across a heart can be obtainable and communicable to an external monitor. Through the use of one or more electrodes/leads, it is possible to detect intra-cardiac rhythm along various lead positions. ECG-integrated valve implant devices in accordance with the present disclosure can be any type of valve, such as aortic, mitral, pulmonic, or tricuspid valves, or can be transcatheter heart valves (THV) or transcatheter mitral valves (TMVR). With respect to valve implants having a stent component (e.g., wireframe or the like), ECG electrode(s) can be disposed on, or otherwise associated with, the stent. However, where the stent comprises metal or other conductive material, multiple electrodes may need to be at least partially electrically isolated from one another in order to provide for desirable differential readings between the electrodes. For example, one electrode can be disposed on the stent, while another electrode can be disposed on another component of the implant device that is at least partially electrically isolated from the stent electrode.

ECG sensors implanted in a patient can advantageously provide closer proximity to the source of electrical impulses in the heart than external sensors disposed on, for example, the skin of a patient. By integrating ECG electrodes with an implanted valve, the ECG functionality can advantageously be implemented with minimal additional physician activity and/or electrical components. In certain embodiments one or more electrodes associated with a valve implant can be coupled to, or work in concert with, one or more electrodes outside of the implant device, which can provide desirable vector(s).

The ECG-integrated implant 3310 can provide certain advantages over pacemaker procedures/functionality. For example, while a passive pacemaker may provide only heart rhythm information based on a single lead, a self-contained ECG implant as described herein can provide ECG vectors and can provide amplitude information in addition to heart rhythm information in certain embodiments. Such information can advantageously indicate additional parameters, which can be used to predict cardiac events (e.g., heart attack), or the like. For example, as blood vessels clog, thereby causing weakening of the heart, the amplitude of the detected vector(s) can demonstrate a downward drift, which can be indicative of an impending cardiac event. The amplitude information can be used by a controller or user to predict a cardiac event, provide a relevant diagnosis, and/or execute a treatment to the patient.

The wires or conduction paths 3303, 3305 can run underneath a cloth covering of the implant 3310, and/or can be integrated with physical structure of the implant 3310, such as wireforms, plastic stents/forms, stiffening bands/structures, or the like.

Figure 40:
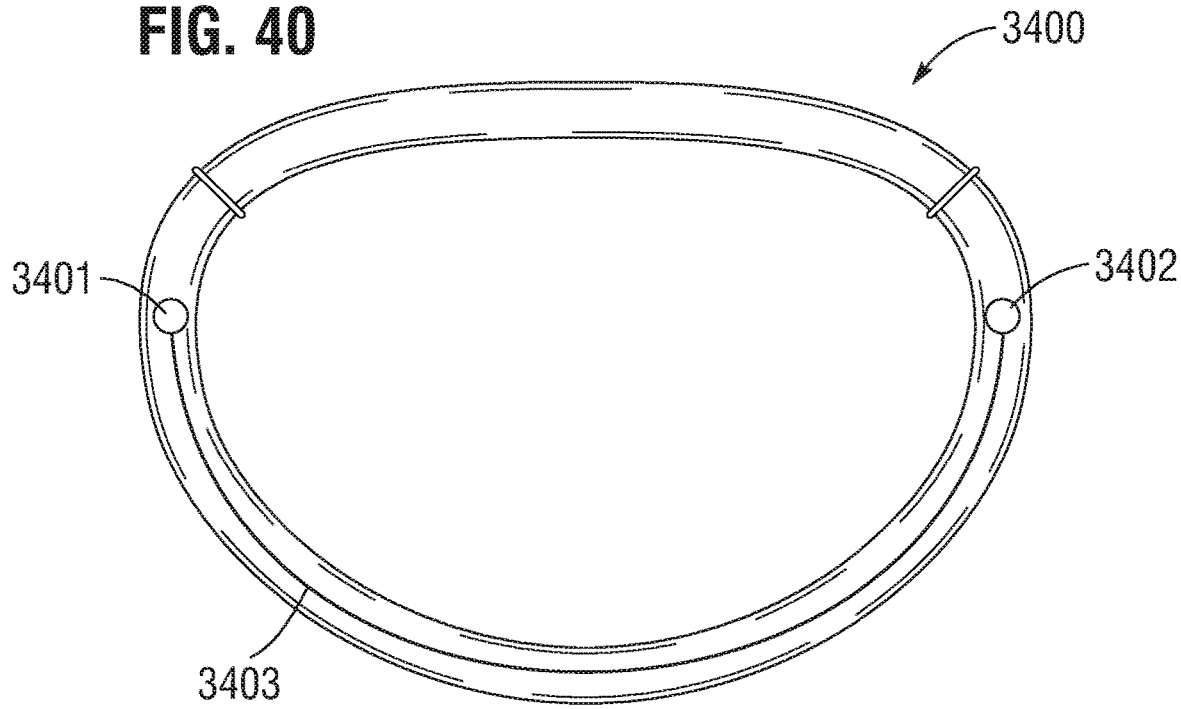
FIG. 40 illustrates an annuloplasty ring according to one or more embodiments.

FIG. 40 shows an embodiment of an electrocardiograph-enabled annuloplasty ring 3400. The annuloplasty ring 3400 can be used for the repair of a native heart valve. For example, the annuloplasty ring 3400 can provide a surgical device that can be used for the repair of leaking valves, such as for example, mitral valves. Due to various factors, the leaflets that normally seal a natural valve to retrograde flow may not coapt properly. Surgical repair of such valves can involve the implantation of an annuloplasty ring to reshape the native valve annulus, wherein the annuloplasty ring pulls the leaflets together to facilitate coaptation and helps to re-establish native valve function.

The annuloplasty ring 3400 can have any or all of the ECG components and/or functionality described above in connection with FIG. 39. ECG electrodes/leads for integration in implant devices, as described herein, can be implemented in annuloplasty rings in any position. The annuloplasty ring 3400 can comprise one or more electrodes or electrical elements 3401, 3402, for detecting electrical vectors associated with the heart of a patient in whom the annuloplasty ring 3400 is implanted. For example, where one of the electrical elements 3401, 3402 is an electrode, the other can represent an ECG controller, which can provide a common voltage reference for providing the electrical vector. The electrical elements 3401, 3402 can be electrically coupled via a wire or other conductive path 3403. Although only two electrical elements or electrodes are illustrated, it should be understood that any number of electrical elements or electrodes can be integrated with the annuloplasty ring 3400. The electrodes/electrical elements 3401, 3402 can be disposed on or proximate to an inner surface of the annuloplasty ring 3400, and/or on the outer surface of the annuloplasty ring 3400.

Figure 41:
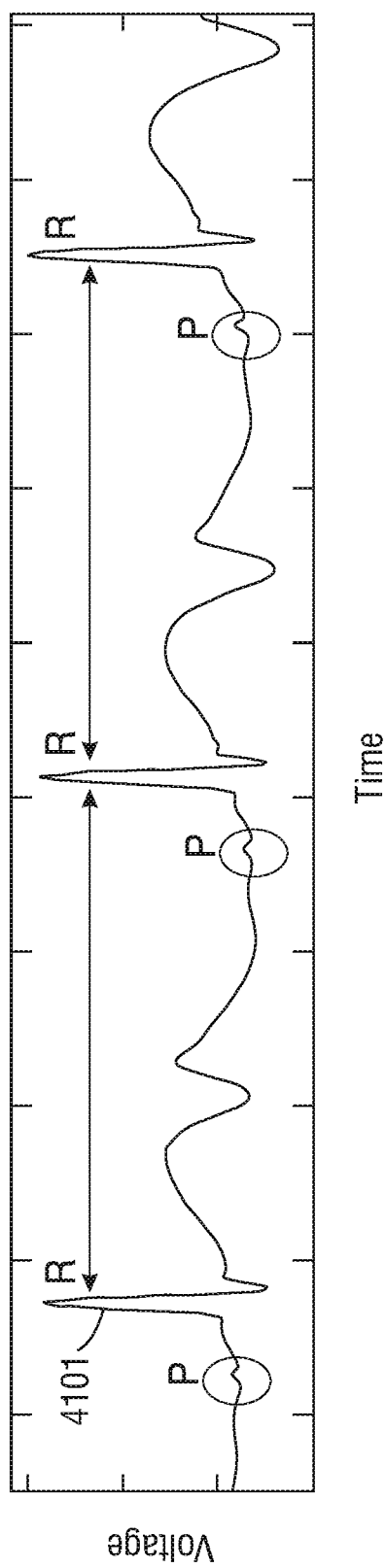
FIGS. 41 and 42 are graphs illustrating experimental results associated with an ECG-integrated implant device according to an embodiment.
Figure 42:
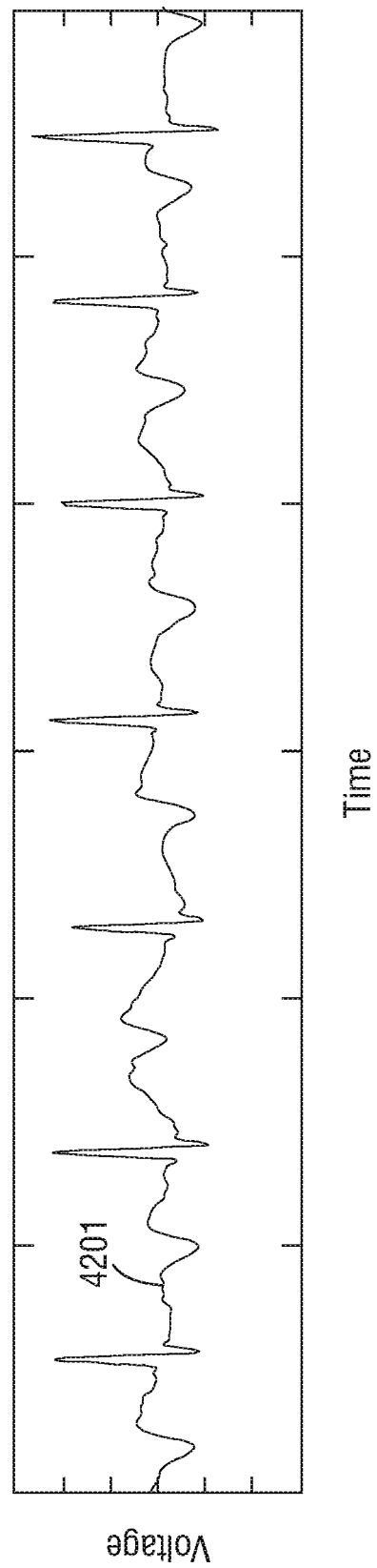

FIGS. 41 and 42 provide example experimental results achieved using embodiments of implant devices with integrated ECG electrodes, as described above. FIGS. 41 and 42 show data readings from an example ECG-integrated mitral valve implant device with electrodes coupled to commissures and cusps of the implant device. The waveform 4101 of the graph of FIG. 41 illustrates the strength of the ECG signal over time. The ECG signal 4101 is based on the collection of electrical signals between different locations in the mitral annulus and left ventricle. The implant device and/or electrodes can be placed in the left side of the heart at a location that maximizes the strength of the ECG signals. The ECG waveform 4101 shows an identifiable repeating P wave (relatively small deflection identified in FIG. 41), which represents atrial depolarization, as well as an R wave, which reflects depolarization of the main mass of the ventricles. The illustrated R-to-R interval can be considered relatively consistent; the waveform 4101 was generated under relatively steady heart rate conditions. The waveform 4101 is representative of a baseline cardiac condition, and is generally similar to the waveform one would expect using traditional ECG devices. The ECG waveform 4101 demonstrates that an ECG signal can be acquired from within the heart using electrodes associated with a valve implant device.

The experimental results represented in FIGS. 41 and 42 further illustrate that ECG-integrated implant devices in accordance with the present disclosure can also be used to detect atrial fibrillation and/or other heart failure conditions. FIG. 42 provides an ECG signal 4201 generated during an atrial fibrillation condition of the heart. As described above, the waveform 4101 of FIG. 41 represents a baseline ECG waveform that establishes the sinus rhythm. The waveform 4201 includes characteristics that allow for the identification of atrial fibrillation. During atrial fibrillation, characterized by an abnormal heart rhythm caused by rapid and irregular beating, the blood pressure is generally not as consistent as during a healthy condition. The waveform 4201 lacks the identifiable P waves of the healthy heart signal, which can be interpreted as an artefact indicating atrial fibrillation. In view of the results illustrated in FIGS. 41 and 42, embodiments of ECG-integrated implant devices as disclosed herein can provide the potential to identify heart rate, irregular rhythm, atrial fibrillation, atrial flutter, multifocal Atrial tachycardia (MAT), and/or other heart conditions. Furthermore, ECG-integrated implant devices in accordance with the present disclosure can provide for energy harvesting, such as with the use of one or more piezoelectric crystals.

Implant with Integrated Flow Sensor

The above disclosure describes various embodiments of prosthetic heart valves that incorporate, for example, micro electromechanical sensors (MEMS) configured to provide sensor signals indicative of various physiological parameters and/or conditions. The sensor information generated by such sensors can be useful in the diagnosis and/or treatment of certain health concerns, such as cardiac health concerns. Blood flow represents a physiological parameter that can be indicative of cardiac health and/or other health conditions. Certain embodiments disclosed herein provide for heart valves and other implant devices that can be integrated and/or associated with one or more sensors configured to provide readings indicative of blood flow, or one or more parameters associated therewith. In certain embodiments, a heart valve or other implant device having one or more flow sensors associated therewith can further comprise sensor signal processing circuitry and/or wireless transmission circuitry for processing and communicating sensor-related information to an external receiver when the implant device is deployed within a patient. According to one or more embodiments disclosed herein, "blood flow" may refer to a measurement or parameter indicative of the movement of blood within a blood vessel, and can be expressed in terms of fluid density and/or fluid velocity. With respect to the diagnostic analysis and treatment of heart conditions, blood flow measurements can be useful for various purposes.

Figure 43:
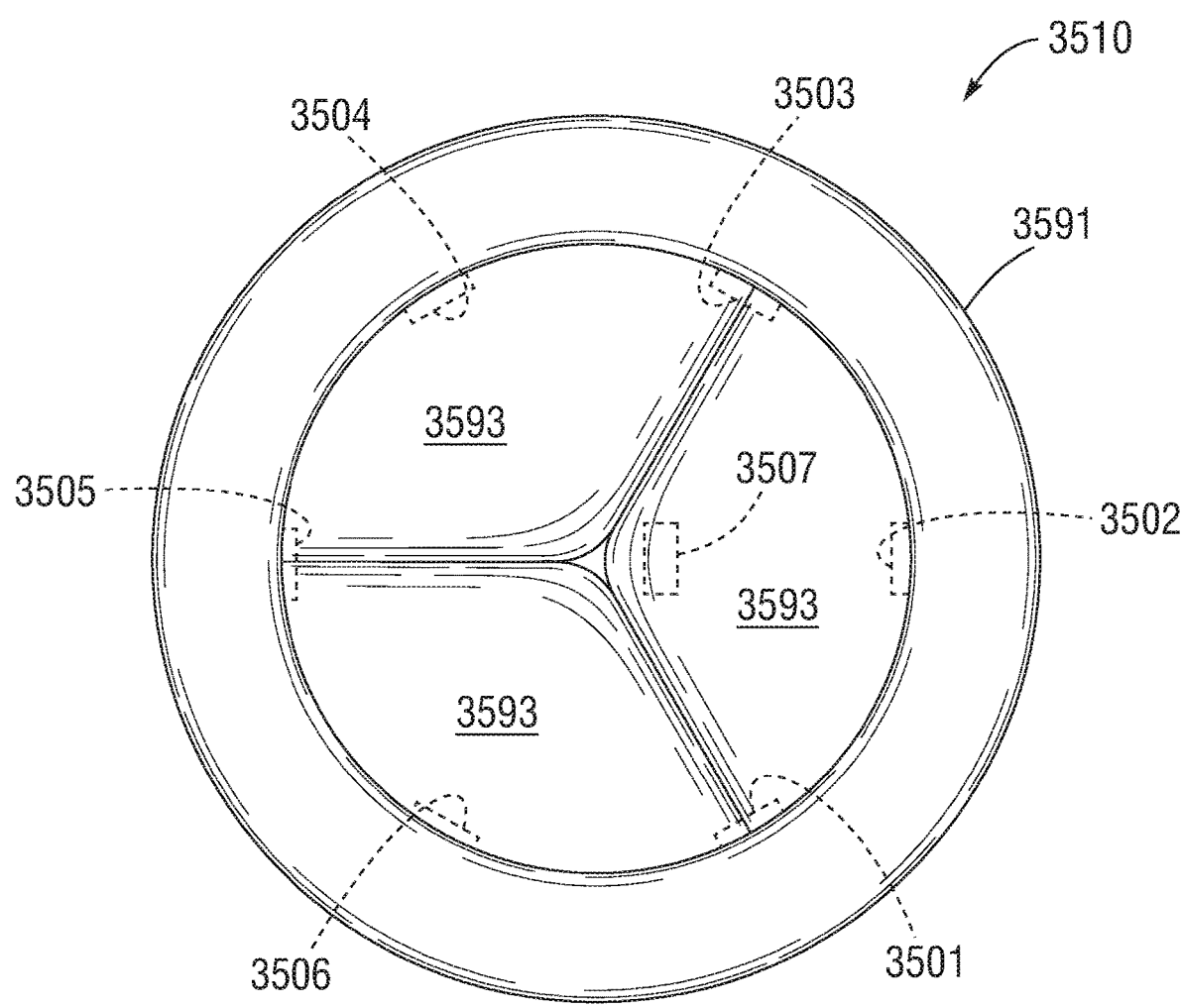
FIG. 43 illustrated a bottom view of an implant device having one or more flow sensors incorporated therewith in accordance with one or more embodiments.

FIG. 43 illustrates a bottom view of an implant device 3510, such as a prosthetic heart valve, having one or more flow sensors incorporated therewith in accordance with one or more embodiments. As described above, when a patient receives a prosthetic heart valve implant, or other implant device, the period of time following the implant operation, such as the first 30-90 days following the implant operation, can be significant with respect to survival of the patient and/or the responsiveness of the patient to the implant device(s). During such period, the patient's cardiac condition can degrade rapidly in certain situations, which can possibly lead to serious health complications and/or death. To the extent that blood flow readings can be relevant to a cardiac-health-related issue of interest, on-going monitoring of blood flow using a sensor-integrated implant device can allow for early detection and/or intervention when complications, or parameters indicative thereof, arise. Continuous or frequent monitoring of cardiac function can provide early warnings indicating that intervention is necessary or desirable.

In certain embodiments, it may be desirable to dispose one or more flow sensors at or near an interior flow channel of a heart valve 3510. For example, FIG. 43 illustrates various positions where flow sensors (3501-3507) can be connected or disposed on the valve implant 3510. Due to the orientation/position of the valve 3510 at least partially within a blood vessel, such as the aorta or other artery, the blood flow through the inner lumen provided by the valve 3510 can advantageously present a measurable blood flow at or near the inner diameter of the sealing ring 2591. The various flow sensor(s) integrated in the valve 3510 can comprise MEMS hot-wire or hot-film sensors. The sensor locations 3501-3506 represent possible location where flow sensor(s) can be placed on the inflow side of the valve 3510 on its inner diameter to allow for measurement of flow through the valve 3510. As shown, one or more flow sensors can be disposed on or within an inner portion of a sealing ring component 3591 of the prosthetic heart valve 3510. For example, where a prosthetic heart valve 3510 comprises a plurality of valve leaflets 3593, one or more flow sensors (e.g., 3501, 3503, 3505) can be disposed at a portion of the sealing ring 3591 at or near a point of convergence, or coaptation, of two leaflets. Additionally, or alternatively, one or more sensors can be disposed at a portion of the sealing ring 3591 at or near an intermediate region of a valve leaflet, as shown at flow sensor locations 3502, 3504, 3506. Additionally or alternatively, one or more flow sensors of a sensor-integrated prosthetic heart valve can be connected to or associated with a valve leaflet, such as sewn to a valve leaflet, as shown with respect to flow sensor 3507. Such flow sensor can advantageously be relatively small and/or lightweight to prevent undesirable alteration of leaflet functionality/performance caused by the sensor 3507.

Although certain positions on an inner portion of the heart valve 3510 are shown as being associated with flow sensors, it should be understood that flow sensors in accordance with the present disclosure can be disposed or associated with any component or portion of the heart valve 3510, and can be attached or connected to the heart valve 3510 in any desirable way, such as through suturing, adhesive connection, or other connection means. In certain embodiments, flow sensor(s) can be disposed in physical proximity to the sinoatrial node, which can provide sufficient temperature differential to indicate flood flow parameters. In certain embodiments, the flow sensor(s) can be disposed on, or otherwise associated with, a sewing ring component of a valve implant. Although dashed boxes are shown in FIG. 43, it should be understood that flow sensors in accordance with the present disclosure can comprise any suitable or desirable shape and/or form factor. Flow sensor(s) integrated with prosthetic heart valves or other implants can be electrically coupled to signal processing and/or transmission circuitry (not shown) in order to provide for monitoring functionality when the implant is deployed within a patient.

Flow sensors for integration with prosthetic heart valves can be any type of flow sensor. Certain flow sensors in accordance with the present disclosure may be referred to herein as anemometers, wherein a flow sensor can comprise any suitable or desirable type of anemometer, or the like. Flow measurements implemented using valve-integrated flow sensors can be related to volume flux or average flow rate of blood.

Example types of flow sensors that can be integrated with a prosthetic heart valve can include optical anemometers, such as sensors utilizing beams of laser light designed to impinge on moving particles of blood flow and be partially scattered with a change in wavelength proportional to the speed of flow of the fluid according to the Doppler effect. The blood particles can scatter the light with a Doppler shift, wherein analysis of this shifted wavelength can be used to determine the speed of the particle, and thus provide an approximation of the blood flow velocity.

Example types of flow sensors that can be integrated with a prosthetic heart valve can further include thermal dilution sensors, which can utilize injection of a quantity of heat at an upstream location, and measurement of a change in temperature downstream at, for example, the sealing ring of the heart valve implant using a thermometer sensor. In one embodiments, heat can be injected into the blood flow at the sealing ring 3591, wherein the change in temperature can be determined a downstream location within the implant device 3510, such as at a distal end of a commissure post or at a valve leaflet edge. Flow can be computed by analysis of the change in temperature over time.

Example types of flow sensors that can be integrated with a prosthetic heart valve can include one or more of hot-film and hot-wire anemometers. Hot-film and hot-wire anemometers can be implemented in any suitable or desirable manner in accordance with the present disclosure. For example, certain embodiments utilize a constant-current applied across a filament that is exposed to the blood flow proximal to the sensor(s). Changes in flow across the filament can affect the rate of heat transfer from it, thereby changing the voltage across the sensor. The change in voltage can therefore be proportional to the change in flow rate of the blood flow across the sensor filament. In certain embodiments, a hot-film or hot-wire anemometer maintains a substantially constant temperature in the filament by varying the current through it to compensate for heat transfer resulting from convection caused by blood flow across the sensor. The change in current to the filament at constant temperature can therefore be proportional to the change in flow rate across the sensor filament. In certain embodiments, hot-wire and/or hot-film anemometers integrated in prosthetic heart sensors can be advantageously configured to provide operational readings in blood having a temperature differential as little as a few degrees Celsius, or less, between the sensor and the ambient blood flow. Where relatively small temperature differentials are utilized, risk of damage to blood cells caused by overheating can be reduced or minimized. In certain embodiments, hot-film and/or hot-wire anemometer sensors in accordance with the present disclosure comprise sensor filaments that comprise biocompatible materials, such as tungsten, or the like.

Hot-film or hot-wire flow sensors integrated in prosthetic heart valves can comprise one or more wires or films formed or disposed on a substrate, such as a polyimide substrate or the like. The substrate and/or other assembly component(s) can advantageously be relatively thin in order to allow for a reduced form factor, such that the sensor(s) do not substantially obstruct or alter the blood flow. The various hot wires/films, conductors, and/or bond pads can comprise any suitable or desirable material, such as nickel, copper, or the like.

In certain embodiments, the flow sensor(s) integrated in the heart valve device 3510 are used to generate flow waveforms, wherein integration of the flow waveforms can be used to calculate cardiac output (CO). Additionally or alternatively, other parameters can be determined, such as heartrate and/or regurgitation. For example, heartrate can be determined by analyzing the frequency of the flow signal, whereas regurgitation can be determined by measuring flow during diastole. Changes or trends in such physiologic parameters can help determine whether the patient's health is in a state of decline and/or whether medical attention is needed. With respect to regurgitation determination, one or more sensors disposed in a position proximate to a region of convergence of the valve leaflets 3593 can be used to advantageously allow for measurement of relatively small amounts of regurgitation flow when the edges of the leaflets do not come into proper coaptation.

The flow sensor(s) (e.g., MEMS flow sensor(s)) can be electrically connected to a circuit board (not shown), which can be integrated into one or more valve components, as described in detail above. The flow sensor(s) and/or connected circuitry can further be coupled to a radio-frequency (RF) antenna (not shown), which can be used to charge the device wirelessly. The sensor-integrated valve 3510 can communicate with a receiver device external to the patient, such as a smart phone or other computing device. For example, the sensor-integrated valve 3510 can be configured to communicate using a known wireless protocol, such as WiFi or Bluetooth, or some other communication protocol. In some embodiments, the implant device 3510 includes one or more power storage devices for providing power to the flow sensor(s).

The flow sensor(s) can be configured to take readings continuously or periodically/sporadically. In certain embodiments, flow sensor readings are taken and recorded over a period of time before being downloaded to an external device. In certain embodiments, flow sensor readings can be taken on-demand as requested by an external host device/system.

As described above, the flow sensor(s) can be configured to measure heat transfer, which can be proportional to velocity. The flow sensor(s) (e.g., 3501-3507) and/or associated circuitry can be calibrated to the expected and/or actual disposition/conditions of the valve 3510 and/or sensor(s). For example, it can be determined that a certain velocity near an inlet of a valve where one or more sensors can be disposed can correspond to a certain volumetric flow rate, wherein cardiac output can be derived from the volumetric flow rate. In certain embodiments, the flow waveform shape can be analyzed at a detail level. For example, the integral of the waveform can be used to derive cardiac output. In certain embodiments, specific features of the shape of the curve can be used to indicate cardiac performance. Signal processing of the flow waveform can be used to predict patient health over a relatively short period of time.

Positioning/placement of flow sensors integrated with prosthetic heart valves can be based at least in part on expected fluid dynamics associated with the heart valve within the target blood vessel. For example, as shown in FIG. 25 and described above in connection therewith, vortices can form in the vicinity of commissure posts of a heart valve. It may be desirable to position flow sensor(s) in a region not substantially influenced by such vortices, such as on the inner inflow diameter of the sealing ring 3591. In certain embodiments, it may be desirable to capture flow readings influenced by vortices formed near commissure posts, and therefore flow sensor(s) can be placed on or near commissure posts, either on the inside or outside portions thereof.

The blood flow from the relevant heart ventricle may not represent a perfect, or uniform, plug flow; blood flow in certain regions of the heart or artery can be more uniform than others, and therefore provide a more reliable flow waveform. Relatively uniform blood flow regions can be at least partially dependent on patient anatomy. Therefore, the position of blood flow sensors can be tailored to the particular physical anatomy of the patient to match the patient's anatomy or to be disposed in a region with relatively uniform flow. Determination of uniform blood flow location can be performed in any suitable manner, such as through the use of echo-based technologies.

Due to energy considerations, in certain embodiments, flow sensors integrated with prosthetic heart valves can be pulsed or only sporadically or periodically activated. Alternatively, flow sensors can operate substantially continuously.

Although certain embodiments of flow-sensor-integrated heart valves are disclosed, wherein flow sensor(s) are physically coupled to the structure of the heart valve, other embodiments are contemplated in which flow sensor(s) associated with a heart valve can be physically separate from the heart valve. For example, in certain embodiments, one or more flow sensors can be disposed downstream from the heart valve, wherein the sensor(s) can be tethered to, or otherwise communicatively and/or physical coupled to the heart valve. In certain embodiments, one or more flow sensors can be integrated in a valve conduit structure that can be implanted in the patient with or near the heart valve 3510. The valve conduit can serve to replace a damaged blood vessel portion. The valve conduit can be a single unit with the heart valve, or can be physically separate. Although flow-sensor-integrated heart valves are discussed in detail herein, it should be understood that flow-sensor-integrated implants in accordance with the present disclosure can comprise other types of implant devices other than heart valves, such as annuloplasty rings, stents, compliance restoration devices, or other types of implants.

Figure 44:
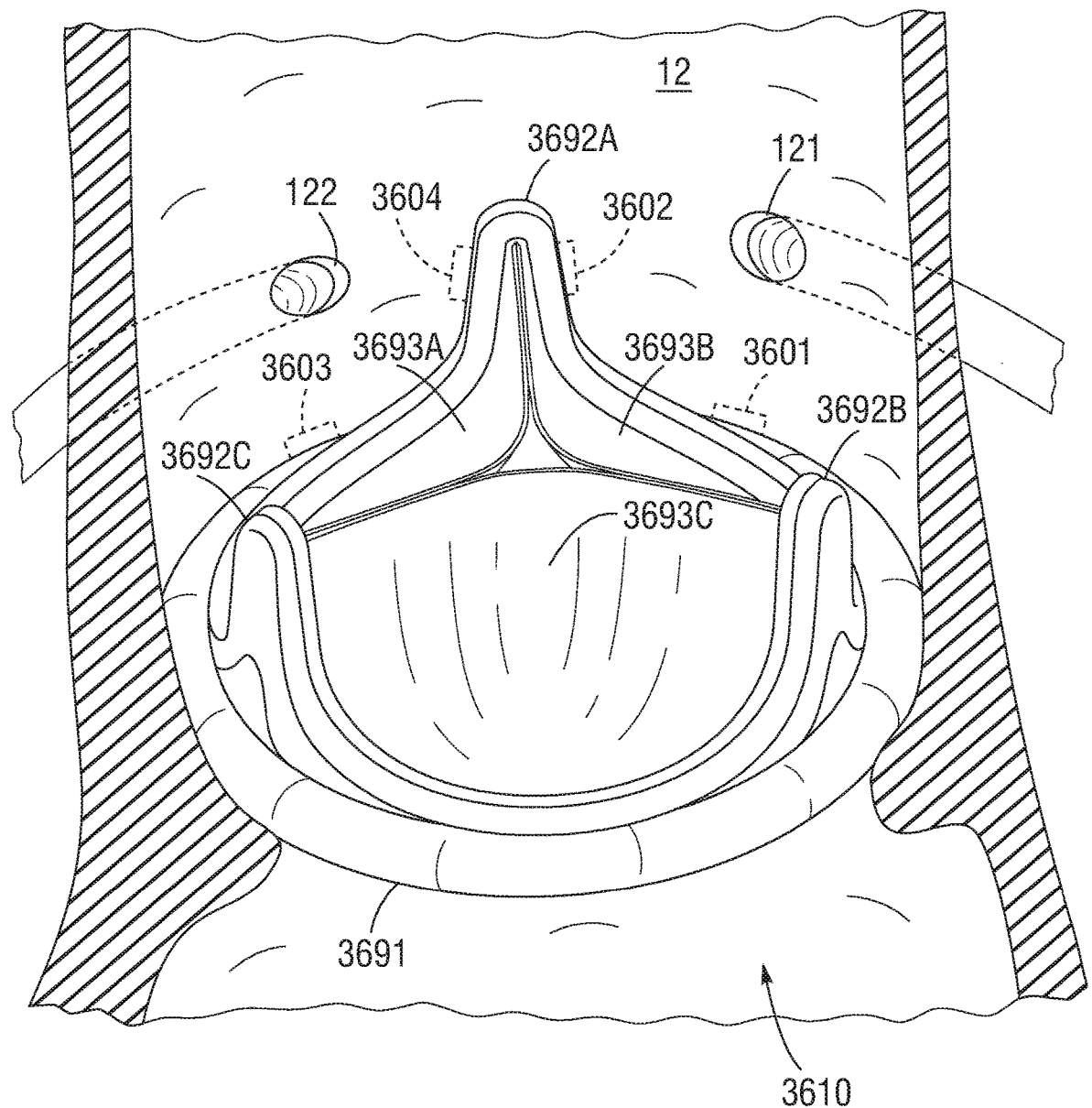
FIG. 44 shows a perspective view of a flow-sensor-integrated heart valve implanted in a blood vessel according to one or more embodiments.

FIG. 44 shows a perspective view of a flow-sensor-integrated heart valve 3610 implanted in a blood vessel 12, such as the ascending aorta of a human patient, according to one or more embodiments. The diagram of FIG. 44 illustrates possible outer locations for flow sensors (3601-3604) in accordance with the present disclosure.

In certain embodiments, it may be desirable to position flow sensor(s) in regions exposed to blood flow that are indicative of secondary blood flows. For example, flow sensors disposed on an outer portion of one or more components of a heart valve, such as on the outflow diameter of a sealing ring 3691, commissure post 3692A, leaflet 3693A, 3693B, or other component can provide an indication of coronary blood flow. For example, a pocket formed between the valve leaflet (e.g., 3693A) and the aorta wall can be exposed to a vortex of blood flow that is funneled to a coronary artery (e.g., right coronary artery 122). Blood flow present in such pocket can therefore provide an indication of coronary blood flow, such as the coronary blood flow in the respective coronary artery proximate to the pocket. In certain embodiments, one or more flow sensors can be disposed on a region of the outside of the heart valve 3610 that is exposed to the blood flow between the heart valve 3610 and a coronary artery. For example, a flow sensor 3603 can be disposed on an outer portion of the sealing ring 3619 below or near the right coronary artery 122. Alternatively or additionally, the flow sensor 3601 can be disposed on an outer portion of the sealing ring 3691 below or near the left coronary artery. Additional or alternative flow sensor locations can include on a side of the commissure post 3692A facing the right coronary artery 122, as shows at location 3604, and/or a side of the commissure post 3692A facing the left coronary artery 121, as shown at location 3602.

In certain embodiments, one or more flow sensors can be disposed in a position to provide sensor readings indicative of regurgitation flow. For example, one or more flow sensors can be disposed in proximity to a coaptation point of the leaflets 3693. Regurgitation information can be of particular interest in the hours or days after the valve implant procedure; once blood pressure recovers after implantation, initial regurgitation may generally subside. In certain embodiments, one or more flow sensors can be disposed on an outflow or inflow side of one or more valve leaflets to provide regurgitation readings. In addition, as the heart valve 3610 can comprise one or more cloth coverings and/or components, one or more sensors can be disposed to detect leakage through certain cloth areas. Such leaking may occur before the valve cloth portions sufficiently clot-off according to the patient's normal clotting function. For example, one or more flow sensors can be place on or within the relevant cloth portion.

In certain embodiments, one or more flow sensors can be disposed in positions designed to detect undesirable suture looping that may occur during implantation of the heart valve 3610. Suture looping may occur due to obstructed operator visibility when suturing the heart valve 3610 to the wall tissue; one or more suture loops may undesirably become tied across two or more valve leaflets, thereby inhibiting proper opening of the valve in one or more regions and causing compromised flow through the valve. Suture looping may further result in compromised valve durability. Mitral valve implants can be particularly susceptible to suture looping due to inverted implantation of such valves according to certain procedures. In certain embodiments, one or more flow sensors can be disposed at or near commissure post and/or leaflet regions near leaflet convergence regions to detect whether the desired flow through such convergence regions is present during systole. Where flow is substantially lower through a convergence point between two leaflets than it is through another convergence point between another set of leaflets, such flow disparity can be indicative of suture looping. That is, detection of asymmetric flow through the valve can be relied upon to make suture looping determinations, or determinations regarding certain other surgical issues.

The various embodiments represented by the diagrams of FIGS. 43 and 44 can provide a flow sensor and data transmitting device which could be integrated into a prosthetic heart valve. The sensor system could wirelessly transmit data to a smartphone or other external device. For example, the sensor system can be configured to transmit alert signals to the appropriate medical personnel if the sensed data indicates an unfavorable trend in the patient's condition.

It should be understood that the various sensors and sensor processes disclosed herein can be combined in single embodiments to provide desired sensor-integrated implant functionality. For example, a heart sensor having one or more flow sensors configured to provide information relating to flow volume can be used in combination with commissure post deflection devices and/or circuitry to provide functionality that can allow for calculations and/or determinations of complexity and/or accuracy that may not be achievable in a system comprising only a single type of sensor or processing capability. Such a combined flow sensor and deflection sensor integrated implant device can allow for the derivation of stroke volume, local flow volume, and/or other cardiac-health-related parameters.

It should be understood that any of the sensors and/or valves disclosed herein can comprise materials and/or coatings designed to at least partially prevent undesired tissue overgrowth.

Additional Embodiments

FIG. 45 illustrates an embodiment of a sensor-integrated valve implant device 4510 according to one or more embodiments. The implant device 4510 comprises a skirt 4518 having one or more sensor (e.g., pressure sensor, flow sensor, etc.) and/or transmission features or components (e.g., coil) integrated therewith. The outer skirt 4518 can have a lower edge portion 4560 and an upper edge portion 4562 defining a plurality of alternating projections 164 and notches 4566. The lower edge portion 4560 of the skirt 4518 can be sutured to the lower edge of the inner skirt 4516 at the inflow end of the valve. Each projection 4564 can be sutured to a rung of the struts of the frame 4512. The corners 4562 of the projections 4564 can be folded over respective struts of the rung and secured with sutures 4568.

The outer skirt 4518 can be secured to the frame 4512 such that when the frame is in its expanded state, there is excess material or slack between the outer skirt's lower and upper edges 4560, 4562 that does not lie flat against the outer surface of the frame 4512. In other words, the outer skirt can be configured with excess material which causes the outer skirt to bulge outwardly as the frame foreshortens (i.e., shortens in length) during radial expansion. Accordingly, when the valve 4510 is deployed within the body, the excess material of the outer skirt 4518 can fill in gaps between the frame 4512 and the surrounding native annulus to assist in forming a fluid-tight seal between the valve and the native annulus. The outer skirt 4518 therefore cooperates with the inner skirt 4516 to avoid perivalvular leakage after implantation of the valve 4510. In certain embodiments, the slack between the lower and upper edges of the outer skirt 4518 allows the frame 4512 to elongate axially during crimping without any resistance from the outer skirt 4518 and the outer skirt does not substantially affect the outer diameter of the prosthetic valve in the crimped condition.

In some implementations, one or more sensors in accordance with the present disclosure, such as one or more strain gauges, piezoelectric sensors, ECG electrodes, capacitive and/or resistive MEMS sensors, flow sensors, or the like, can be attached to, or otherwise integrated with the skirt 4518. The sensor(s) can be attached to the outside of the skirt 4518 or at least partially nested between the outer skirt 4518 and inner skirt 4516. Furthermore, in certain embodiments, a power and/or data transmission coil for communication with an externally located receiver/transmitter can be attached to, or otherwise associated with, the skirt 4518. In certain embodiments, a data and/or power transmission wire can be used to suture the skirt 4518 or other component of the valve 4510.

Depending on the embodiment, certain acts, events, or functions of any of the processes or algorithms described herein can be performed in a different sequence, can be added, merged, or left out altogether. Thus, in certain embodiments, not all described acts or events are necessary for the practice of the processes. Moreover, in certain embodiments, acts or events can be performed concurrently, e.g., through multi-threaded processing, interrupt processing, or via multiple processors or processor cores, rather than sequentially.

Certain methods and/or processes described herein can be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module can be compiled and linked into an executable program, installed in a dynamically linked library, or can be written in an interpreted programming language such as, for example, BASIC, Perl, or Python. It will be appreciated that software modules can be callable from other modules or from themselves, and/or can be invoked in response to detected events or interrupts. Software instructions can be embedded in firmware, such as an erasable programmable read-only memory (EPROM). It will be further appreciated that hardware modules can be comprised of connected logic units, such as gates and flip-flops, and/or can be comprised of programmable units, such as programmable gate arrays, application specific integrated circuits, and/or processors. The modules described herein are preferably implemented as software modules, but can be represented in hardware and/or firmware. Moreover, although in some embodiments a module can be separately compiled, in other embodiments a module can represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with patients, health care practitioners, administrators, other systems, components, programs, and so forth.

Embodiments of the disclosed systems and methods can be used and/or implemented with local and/or remote devices, components, and/or modules. The term "remote" may include devices, components, and/or modules not stored locally, for example, not accessible via a local bus. Thus, a remote device may include a device which is physically located in the same room and connected via a device such as a switch or a local area network. In other situations, a remote device may also be located in a separate geographic area, such as, for example, in a different location, building, city, country, and so forth.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is understood with the context as used in general to convey that an item, term, element, etc. may be either X, Y, or Z. Thus, such conjunctive language is not generally intended to imply that certain embodiments require at least one of X, at least one of Y, and at least one of Z to each be present.

Reference throughout this specification to "certain embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics can be combined in any suitable manner, as would be apparent to one of ordinary skill in the art from this disclosure, in one or more embodiments.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

What is claimed is:

1. A prosthetic valve comprising:
   a plurality of valve leaflets;
   a frame assembly configured to support the plurality of valve leaflets, the frame assembly comprising an outer frame defining arcuate commissure regions and a flexible band comprising commissure support portions configured to fit at least partially within the arcuate commissure regions of the outer frame, the valve leaflets being secured at least in part between the outer frame and the flexible band;
   a strain gauge device including one or more conductors applied directly to an outer surface of one of the commissure support portions of the flexible band, the strain gauge device being configured to generate a sensor signal providing a direct measurement of radial deflection of the one of the commissure support portions; and
   a transmitter assembly configured to receive the sensor signal from the strain gauge device and wirelessly transmit a transmission signal, wherein the transmission signal is based at least in part on the sensor signal.

2. The prosthetic valve of claim 1, wherein the one or more conductors are disposed in one or more etched channels formed in the one of the commissure support portions of the flexible band.

3. The prosthetic valve of claim 1, wherein the one or more conductors are printed on the outer surface of the one of the commissure support portions of the flexible band.

4. The prosthetic valve of claim 1, further comprising one or more piezoelectric crystals attached to the flexible band and configured to generate power for use by the prosthetic valve.

5. The prosthetic valve of claim 1, wherein the transmitter assembly is configured to receive power wirelessly from an external power supply and transmit the transmission signal using the received power.

6. The prosthetic valve of claim 5, wherein the external power supply comprises a wearable strap configured to be worn around an abdomen of a patient in whom the prosthetic valve is implanted.

7. The prosthetic valve of claim 1, further comprising a piezoresistive sensor device.

8. The prosthetic valve of claim 1, wherein the transmitter assembly comprises an antenna coil wrapped around a stiffening band of the frame assembly.

9. A prosthetic valve comprising:
   a plurality of valve leaflets;
   a frame assembly configured to support the plurality of valve leaflets, the frame assembly comprising an outer frame defining arcuate commissure regions and a flexible band comprising commissure support portions configured to fit at least partially within the arcuate commissure regions of the outer frame, the valve leaflets being secured at least in part between the outer frame and the flexible band;
   a power generator implemented within one of the commissure support portions of the flexible band, the power generator comprising a piezoelectric polymer layer disposed between first and second conductive layers that are sealed within the one of the commissure portions of the flexible band; and
   a transmitter assembly configured to wirelessly transmit a transmission signal using power using power generated by the power generator.

10. The prosthetic valve of claim 9, wherein the transmitter assembly includes an electrically conductive coil, wherein the transmitter assembly is further configured to perform said wireless transmission using the coil.

11. The prosthetic valve of claim 9, wherein one or more of the commissure support portions are configured to deflect in response to formation of fluid vortices in a fluid channel in which the prosthetic valve is disposed.

* * * * *